(12) United States Patent
Plant et al.

(10) Patent No.: US 6,632,833 B1
(45) Date of Patent: *Oct. 14, 2003

(54) 2-(2-METHYLPHENYL)-3,4-DIHYDRO-2H-PYRROLE DERIVATIVES

(75) Inventors: Andrew Plant, Leverkusen (DE); Dirk Backhaus, Köln (DE); Christoph Erdelen, Leichlingen (DE); Andreas Turberg, Haan (DE); Norbert Mencke, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/700,288

(22) PCT Filed: May 5, 1999

(86) PCT No.: PCT/EP99/03062

§ 371 (c)(1),
(2), (4) Date: Nov. 13, 2000

(87) PCT Pub. No.: WO99/59967

PCT Pub. Date: Nov. 25, 1999

(30) Foreign Application Priority Data

May 18, 1998 (DE) ......................................... 198 22 245

(51) Int. Cl.$^7$ ........................ A01N 43/36; C07D 207/20
(52) U.S. Cl. ...................... 514/422; 514/429; 548/525; 548/526; 548/527; 548/565
(58) Field of Search ................. 548/565, 525, 548/526, 527; 514/422, 429

(56) References Cited

U.S. PATENT DOCUMENTS 6,274,613 B1 * 8/2001 Plant et al. ................. 514/408
6,399,771 B1 * 6/2002 Plant et al. ................. 540/611

FOREIGN PATENT DOCUMENTS

WO     98-22438 A1 * 5/1998

OTHER PUBLICATIONS

E. Profft et al, Journal Für Prakitsche Chemie, 4, Reihe, vol. 1, (month unavailable), 1954, pp. 57–86, XP002113754, cited in the application, p. 85, line 27—p. 86, line 7.

W. Koller et al, Chemische Berichte, vol. 96, (month unavailable), 1963, pp. 93–113, XP002113755, cited in the application, examples 37, 38.

C.F.H. Allen et al, Journal of the American Chemical Society, vol. 51, No. 7, (month unavailable) 1929, pp. 2151–2157, XP002113756, p. 2152, compound IV.

R. Weil, et al, Bull. Soc. Chim. France, No. 1–2, (month unavailable), 1974, pp. 258–262, XP002113757, cited in application p. 259, table I, compound 6.

H. Quast, et al, Chemische Berichte, vol. 116, (month unavailable), 1983, pp. 3931–3946, XP002113758, cited in the application, p. 3935, compound 9.

Journal für Prakitsche Chemie, 4. Reihe, Band 2, (month unavailable), 1955, pp. 53–83, Von F. Seidel et al, "Über die Bildungsweise der 2–Oxynaphthosäure–(3)".

* cited by examiner

*Primary Examiner*—Laura L. Stockton
(74) *Attorney, Agent, or Firm*—Richard E.L. Henderson; Raymond J. Harmuth

(57) ABSTRACT

The invention relates to novel 2-(2-methylphenyl)-3,4-dihydro-2H-pyrrole derivatives of the formula (I)

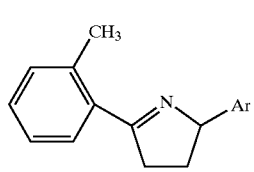

in which
  Ar represents substituted phenyl,
  to a plurality of processes for their preparation and to their use as pesticides.

15 Claims, No Drawings

2-(2-METHYLPHENYL)-3,4-DIHYDRO-2H-PYRROLE DERIVATIVES

This application is a 317 of PCT/EP99/03062 filed May 5, 1999.

The invention relates to novel 2-(2-methylphenyl)-3,4-dihydro-2H-pyrrole derivatives, to a plurality of processes for their preparation and to their use as pesticides.

Hitherto, only few substituted cyclic α,α'-diphenylimines are known: three 2,5-diphenyl-1-pyrrolines which are alkoxy-substituted in the 2-phenyl ring [5-(2,5-dimethoxyphenyl)-2-phenyl-3,4-dihydro-2H-pyrrole and 5-(4-methoxy-phenyl)-2-phenyl-3,4-dihydro-2H-pyrrole from Chem. Ber. 96, 93 (1963) and the corresponding 4-propoxy compound from J. Prakt. Chem., Series 4, 1, 57 (1955)] and the 2,6-diphenyl-3,4,5,6-tetrahydropyridine, which is not substituted any further [cf., for example, Bull. Soc. Chim. Fr. 1974, 258 and Chem. Ber. 116, 3931 (1983)].

Nothing is known concerning their suitability for use as pesticides.

This invention, accordingly, provides novel 2-(2-methylphenyl)-3,4-dihydro-2H-pyrrole derivatives of the formula (I)

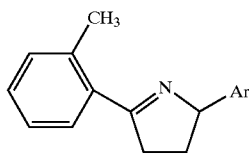

(I)

in which
Ar represents the radical

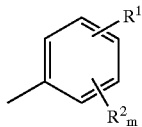

in which
m represents 0, 1, 2, 3 or 4, $R^1$ represents hydrogen, F, Cl, Br, cyano, trialkylsilyl, —CO—$NR^4R^5$, tetrahydropyranyl or represents one of the following groupings
(l) —X—A
(m) —B—Z—D
(n) —Y—E, $R^2$ represents hydrogen, halogen, cyano, nitro, alkyl, alkoxy, halogenoalkyl, halogenoalkoxy, alkoxyalkoxy or —$S(O)_oR^3$, with the proviso that $R^1$ does not represent hydrogen if m=1 and $R^2$=iodine.

o represents 0, 1 or 2, $R^3$ represents alkyl or halogenoalkyl, $R^4$ and $R^5$ independently of one another each represent hydrogen, alkyl, halogenoalkyl or represent phenyl or phenylalkyl, each of which is optionally mono- or polysubstituted by radicals from the list $W^1$, X represents a direct bond, oxygen, sulphur, carbonyl, carbonyloxy, oxycarbonyl, alkylene, alkenylene, alkinylene, alkyleneoxy, oxyalkylene, thioalkylene, alkylenedioxy or dialkylsilylene, A represents phenyl, naphthyl or tetrahydronaphthyl, each of which is optionally mono- or polysubstituted by radicals from the list $W^1$, or represents 5- to 10-membered heterocyclyl containing one or two aromatic rings and having one or more heteroatoms from the group consisting of nitrogen, oxygen and sulphur and being in each case optionally mono- or polysubstituted by radicals from the list $W^2$, B represents p-phenylene which is optionally mono- or disubstituted by radicals from the list $W^1$, Z represents oxygen or sulphur, D represents hydrogen, alkyl, alkenyl, alkinyl, halogenoalkyl, halogenoalkenyl, in each case optionally halogen-, alkyl-, alkenyl-, halogenoalkenyl-, phenyl-, styryl-, halogenophenyl- or halogenostyryl-substituted cycloalkyl or cycloalkylalkyl, represents in each case optionally halogen- or alkyl-substituted cycloalkenyl or cycloalkenylalkyl, represents in each case optionally nitro-, halogen-, alkyl-, alkoxy-, halogenoalkyl- or halogenoalkoxy-substituted phenylalkyl, naphthylalkyl, tetrahydronaphthylalkyl or hetarylalkyl having 5 or 6 ring members and one or two heteroatoms from the group consisting of nitrogen, oxygen and sulphur, represents —CO—$R^6$, —CO—$NR^7R^8$ or represents the grouping
—$(CH_2)_p$—$(CR^9R^{10})_q$—$(CH_2)_r$—G or Z and D together represent optionally nitro-, halogen-, alkyl-, alkoxy-, halogenoalkyl- or halogenoalkoxy-substituted phenoxyalkyl, Y represents a direct bond, oxygen, sulphur, carbonyl, carbonyloxy, oxycarbonyl, alkylene, alkenylene, alkinylene, alkyleneoxy, oxyalkylene, thioalkylene, alkylenedioxy or represents p-phenylene which is optionally mono- or disubstituted by radicals from the list $W^1$, E represents hydrogen, alkyl, alkenyl, alkinyl, halogenoalkyl, halogenoalkenyl, in each case optionally halogen-, alkyl-, alkenyl-, halogenoalkenyl-, phenyl-, styryl-, halogenophenyl- or halogenostyryl-substituted cycloalkyl, represents in each case optionally halogen- or alkyl-substituted cycloalkenyl, represents phenyl which is optionally mono- to tetrasubstituted by radicals from the list $W^1$ or represents 5- or 6- membered hetaryl having one or two heteroatoms from the group consisting of nitrogen, oxygen and sulphur and being in each case optionally mono- to tetrasubstituted by radicals from the list $W^2$ or represents the grouping
—$(CH_2)_p$—$(CR^9R^1)_q$—$(CH_2)_r^{10}$—G, $R^6$ represents alkyl, alkoxy, alkenyl, alkenyloxy, in each case optionally halogen-, alkyl-, alkenyl-, halogenoalkyl- or halogenoalkenyl-substituted cycloalkyl, cycloalkyloxy or cycloalkylalkyloxy or represents in each case optionally nitro-, halogen-, alkyl-, alkoxy-, halogenoalkyl- or halogenoalkoxy-substituted phenyl or naphthyl, $R^7$ represents hydrogen or alkyl, $R^8$ represents alkyl, halogenoalkyl, in each case optionally halogen-, alkyl-, alkenyl-, halogenoalkyl- or halogenoalkenyl-substituted cycloalkyl or cycloalkylalkyl or represents in each case optionally halogen-, alkyl-, alkoxy-, halogenoalkyl- or halogenoalkoxy-substituted phenyl or phenylalkyl, p, q and r independently of one another each represent 0, 1, 2 or 3, their sum being smaller than 6 and greater than 1, $R^9$ and $R^{10}$ independently of one another each represent hydrogen or alkyl, G represents cyano, represents an optionally halogen-, alkyl- or halogenoalkyl- and, at the point of linkage, optionally $R^{11}$-substituted 5- or 6-membered heterocycle having 1 to 3 identical or different heteroatoms from the group consisting of nitrogen, oxygen and sulphur or one of the following groups
(a) —CO—$R^{11}$
(b) —CO—$OR^{12}$
(c) —CO—$NR^{13}R^{14}$
(d) —CS—$NR^{13}R^{14}$ (e) 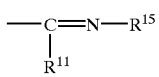

(f) 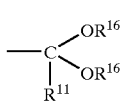

(g) 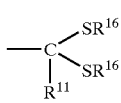

(h) 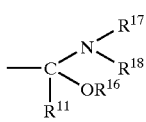

(i) 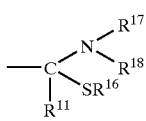

(j) 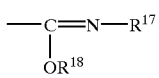

(k) 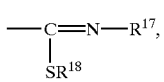

$R^{11}$ represents hydrogen, alkyl, alkenyl, halogenoalkyl, halogenoalkenyl, optionally halogen-, alkyl- or halogenoalkyl-substituted cycloalkyl or represents phenyl which is optionally mono- to pentasubstituted by alkylcarbonylamino, alkylcarbonylalkylamino and/or radicals from the list $W^3$, $R^{12}$ represents hydrogen, alkyl, alkenyl, halogenoalkyl, halogenoalkenyl, in each case optionally halogen-, alkyl- or halogenoalkyl-substituted cycloalkyl or cycloalkylalkyl or represents arylalkyl which is optionally mono- to pentasubstituted by radicals from the list $W^3$, $R^{13}$ and $R^{14}$ independently of one another each represent hydrogen, alkyl, alkenyl, halogenoalkyl, halogenoalkenyl, alkoxy, in each case optionally halogen-, alkyl- or halogenoalkyl-substituted cycloalkyl or cycloalkylalkyl, represents aryl or arylalkyl, each of which is optionally mono- to pentasubstituted by radicals from the list $W^3$, represent —$OR^{12}$ or —$NR^{11}R^{12}$ or together represent an alkylene chain having 2 to 6 members in which optionally one methylene group is replaced by oxygen, $R^{15}$ represents —$OR^{12}$, —$NR^{11}R^{12}$ or —$N(R^{11})$—$COOR^{12}$, $R^{16}$, $R^{17}$ and $R^{18}$ independently of one another each represent alkyl, $W^1$ represents hydrogen, halogen, cyano, formyl, nitro, alkyl, trialkylsilyl, alkoxy, halogenoalkyl, halogenoalkoxy, halogenoalkenyloxy, alkylcarbonyl, alkoxycarbonyl, pentafluorothio or —$S(O)_OR^3$, $W^2$ represents halogen, cyano, formyl, nitro, alkyl, trialkylsilyl, alkoxy, halogenoalkyl, halogenoalkoxy, alkylcarbonyl, alkoxycarbonyl, pentafluorothio, —$S(O)_OR^3$ or —$C(R^{11})$=N—$R^{15}$, $W^3$ represents halogen, cyano, nitro, alkyl, alkoxy, halogenoalkyl, halogenoalkoxy, dialkylamino, —$S(O)_O R^3$, —$COOR^{19}$ or —$CONR^{20}R^{21}$, $R^{19}$ represents hydrogen, alkyl, halogenoalkyl, optionally halogen-, alkyl- or halogenoalkyl-substituted cycloalkyl or represents phenyl which is optionally mono- to pentasubstituted by radicals from the list $W^4$, $R^{20}$ and $R^{21}$ independently of one another each represent hydrogen, alkyl, alkenyl, halogenoalkyl, haligenoalkenyl, alkoxy, in each case optionally halogen-, alkyl- or halogenoalkyl-substituted cycloalkyl or cycloalkylalkyl or represent aryl or arylalkyl, each of which is optionally mono- to pentasubstituted by radicals from the list $W^4$, represent —$OR^{16}$ or —$NR^{17}R^{18}$ or together represent an alkylene chain having 2 to 6 members in which optionally one methylene group is replaced by oxygen, and $W^4$ represents halogen, cyano, nitro, alkyl, alkoxy, halogenoalkyl, halogenoalkoxy, dialkylamino, alkoxycarbonyl, dialkylaminocarbonyl or —$S(O)_OR^3$.

Depending, inter alia, on the nature of the substituents, the compounds of the formula (I) may be present as geometric and/or optical isomers or isomer mixtures, of various compositions, which can be separated, if appropriate, in a customary manner. The present invention provides both the pure isomers and the isomer mixtures, their preparation and use and compositions comprising them. However, hereinbelow, for the sake of simplicity, compounds of the formula (I) are always referred to, although this may mean both the pure compounds and, if appropriate, also mixtures having varying proportions of isomeric compounds.

Furthermore, it has been found that the novel compounds of the formula (I) are obtained by one of the processes described below.

A) Cyclic imines of the formula (I)

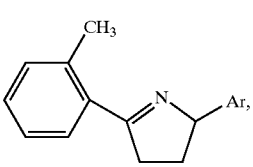

(I)

in which

Ar is as defined above can be prepared by a) reacting aminoketone derivatives of the formula (VIII)

(VIII)

[Structure VIII: 2-methylphenyl ketone with NH-tBOC and Ar substituent]

in which

Ar is as defined above with an acid, followed by cyclocondensation, if appropriate in the presence of an acid binder, or b) reducing the nitro group of nitroketones of the formula (XVIII)

(XVIII)

[Structure XVIII: 2-methylphenyl ketone with NO₂ and Ar]

in which

Ar is as defined above, where

[Structure II in brackets: aminoketone intermediate]

(II)

→

[Structure I: cyclic imine]

(I)

an aminoketone intermediate of the formula (II) is formed which, however, is cyclocondensed in situ to (I), in particular in an acidic medium, or c) hydrolysing imines of the formula (XXVII)

(XXVII)

[Structure XXVII: ketone with N=CPh₂ imine and Ar]

in which

Ar is as defined above with aqueous acids

[Structure II in brackets: aminoketone intermediate]

(II)

→

[Structure I: cyclic imine with 2-methylphenyl and Ar]

(I)

where an aminoketone intermediate of the formula (II) is formed which, however, is cyclocondensed in situ to (I).

B) Cyclic imines of the formula (I) can also be prepared by reacting cyclic O-methylsulphonyl oximes of the formula (III)

(III)

[Structure III: cyclic O-methylsulphonyl oxime with Ar]

in which

Ar is as defined above with aryl Grignard compounds of the formula (IV)

(IV)

[Structure IV: 2-methylphenyl-Mg-Hal]

in which

Hal represents chlorine, bromine or iodine in the presence of a diluent.

C) Cyclic imines of the formula (I-b)

(I-b)

[Structure I-b: cyclic imine with 2-methylphenyl and aryl bearing $R^{1-1}$ and $R_m^{2-1}$ substituents]

in which m is as defined above, $R^{1-1}$ represents A or one of the groupings below

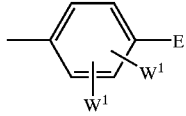
(n-a)

where

A, B, D, E, $W^1$ and Z are each as defined above and $R^{2-1}$ represents hydrogen, fluorine, cyano, nitro, alkyl, alkoxy, halogenoalkyl, halogenoalkoxy, alkoxyalkyl or —$SR^3$ where $R^3$ is as defined above can be prepared by coupling compounds of the formula (V)

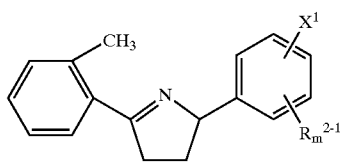
(V)

in which $R^{2-1}$ and m are each as defined above and $X^1$ represents bromine, iodine or —$OSO_2CF_3$ with boronic acids of the formula (VI)

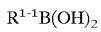
(VI)

in which $R^{1-1}$ is as defined above in the presence of a catalyst and in the presence of an acid binder and in the presence of a solvent.

D) Cyclic imines of the formula (I-c)

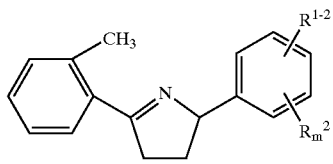
(I-c)

in which $R^2$ and m are each as defined above, $R^{1-2}$ represents one of the groupings below
(m-b) —B—Z—$D^1$
(n-b) —$Y^1$—$E^1$ in which B and Z are each as defined above, $Y^1$ represents oxygen or sulphur and $D^1$ and $E^1$ represent the grouping
—$(CH_2)_p$—$(CR^9R^{10})_q$—$(CH_2)_r$—G in which $R^9$, $R^{10}$, G, p, q and r are each as defined above can be prepared by condensing cyclic imines of the formula (I-d)

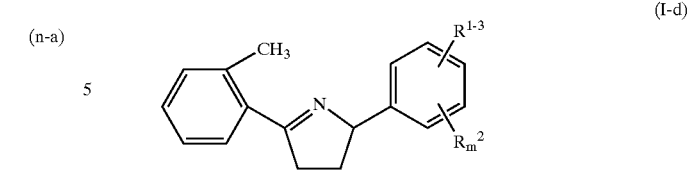
(I-d)

in which $R^2$ and m are each as defined above and $R^{1-3}$ represents one of the groupings below
(m-c) —B—Z—H
(n-c) —$Y^1$—H in which B, $Y^1$ and Z are each as defined above with compounds of the formula (VII)

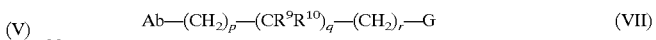

Ab—$(CH_2)_p$—$(CR^9R^{10})_q$—$(CH_2)_r$—G (VII)

in which $R^9$, $R^{10}$, G, p, q and r are each as defined above and

Ab represents a leaving group.

E) Cyclic imines of the formula (I-e)

(I-e)

in which $R^2$ and m are each as defined above and $R^{1-4}$ represents a grouping from the description of the compounds of the formula (I) according to the invention which contains the radical G, where G represents one of the abovementioned groupings (e) to (k), can be prepared by generally customary and known derivatizations of the corresponding keto derivatives, carboxylic acid derivatives or nitriles, i.e. compounds of the formula (I) in which G represents cyano or one of the groupings (a) to (d).

Furthermore, it has been found that the novel compounds of the formula (I) exhibit very good activity as pesticides, in particular against arthropods in agriculture, but also against parasites in the keeping of useful animals and pets, combined with good compatibility with plants.

The formula (I) provides a general definition of the compounds according to the invention. Preferred substituents or ranges of the radicals listed in the formulae mentioned hereinabove and hereinbelow are illustrated below.

Ar preferably represents the radical

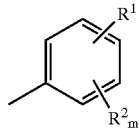

where m preferably represents 0, 1, 2, 3.

$R^1$ preferably represents a substituent in the meta or para position from the group consisting of hydrogen, F, Cl, Br, cyano, tri-($C_1$–$C_6$-alkyl)-silyl, —CO—$NR^4R^5$, tetrahydropyranyl or one of the following groupings
(l) —X—A
(m) —B—Z—D
(n) —Y—E.

$R^2$ preferably represents hydrogen, halogen, cyano, nitro, $C_1$–$C_{16}$-alkyl, $C_1$–$C_{16}$-alkoxy, $C_1$–$C_6$-halogenoalkyl, $C_1$–$C_6$-halogenoalkoxy, $C_1$–$C_8$-alkoxy-$C_1$–$C_8$-alkoxy or —$S(O)_OR^3$.

with the proviso that $R^1$ does not represent hydrogen if m=1 and $R^2$=iodine.

o preferably represents 0, 1 or 2.

$R^3$ preferably represents optionally fluorine- or chlorine-substituted $C_1$–$C_6$-alkyl.

$R^4$ and $R^5$ independently of one another each preferably represent hydrogen, $C_1$–$C_6$-alkyl, $C_1$–$C_6$-halogenoalkyl or represent phenyl or phenyl-$C_1$–$C_4$-alkyl, each of which is optionally mono- to trisubstituted by radicals from the list $W^1$.

X preferably represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylenedioxy or di-$C_1$–$C_4$-alkylsilylene.

A preferably represents phenyl, naphthyl or tetrahydronaphthyl, each of which is optionally mono- to tetrasubstituted by radicals from the list $W^1$, or represents 5- to 10-membered heterocyclyl containing 1 or 2 aromatic rings and having 1 to 4 heteroatoms, which contains 0 to 4 nitrogen atoms, 0 to 2 oxygen atoms and 0 to 2 sulphur atoms (in particular furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl), and is in each case optionally mono- to tetrasubstituted by radicals from the list $W^2$.

B preferably represents p-phenylene which is optionally mono- or disubstituted by radicals from the list $W^1$.

Z preferably represents oxygen or sulphur.

D preferably represents hydrogen, $C_1$–$C_{16}$-alkyl, $C_2$–$C_{16}$-alkenyl, $C_2$–$C_6$-alkinyl, $C_1$–$C_{16}$-halogenoalkyl, $C_2$–$C_{16}$-halogenoalkenyl, in each case optionally halogen-, $C_1$–$C_4$-alkyl-, $C_2$–$C_4$-alkenyl-, $C_2$–$C_4$-halogenoalkenyl-, phenyl-, styryl-, halogenophenyl- or halogenostyryl-substituted $C_3$–$C_8$-cycloalkyl or $C_3$–$C_8$-cycloalkyl-$C_1$–$C_6$-alkyl, represents in each case optionally halogen- or $C_1$–$C_4$-alkyl-substituted $C_5$–$C_8$-cycloalkenyl or $C_5$–$C_8$-cycloalkenyl-$C_1$–$C_4$-alkyl, represents in each case optionally nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, naphthyl-$C_1$–$C_6$-alkyl, tetrahydronaphthyl-$C_1$–$C_6$-alkyl or hetaryl-$C_1$–$C_6$-alkyl having 5 or 6 ring members and 1 or 2 heteroatoms from the group consisting of nitrogen, oxygen and sulphur (in particular furyl methyl, thienylmethyl, pyrrolylmethyl, oxazolylmethyl, isoxazolylmethyl, thiazolylmethyl or pyridylmethyl), represents —CO—$R^6$, —CO—$NR^7R^8$ or represents the grouping
—$(CH_2)_p$—$(CR^9R^{10})_q$—$(CH_2)_r$—G.

Z and D together also preferably represent in each case optionally nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenoxy-$C_1$–$C_4$-alkyl.

Y preferably represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylenedioxy or represents p-phenylene which is optionally mono- or disubstituted by radicals from the list $W^1$.

E preferably represents hydrogen, $C_1$–$C_{16}$-alkyl, $C_2$–$C_{16}$-alkenyl, $C_2$–$C_6$-alkinyl, $C_1$–$C_{16}$-halogenoalkyl, $C_2$–$C_{16}$-halogenoalkenyl, optionally halogen-, $C_1$–$C_4$-alkyl-, $C_2$–$C_4$-alkenyl-, $C_2$–$C_4$-halogenoalkenyl-, phenyl-, styryl-, halogenophenyl- or halogenostyryl-substituted $C_3$–$C_8$-cycloalkyl, represents optionally halogen- or $C_1$–$C_4$-alkyl-substituted $C_5$–$C_8$-cycloalkenyl, represents phenyl which is optionally mono- to tetrasubstituted by radicals from the list $W^1$ or represents 5- or 6-membered hetaryl having 1 or 2 heteroatoms from the group consisting of nitrogen, oxygen and sulphur (in particular furyl, thienyl, pyrrolyl, oxazolyl, isoxazolyl, thiazolyl or pyridyl) which is in each case optionally mono- to tetrasubstituted by radicals from the list $W^2$ or represents the grouping
—$(CH_2)_p$—$(CR^9R^{10})_q$—$(CH_2)_r$—G.

$R^6$ preferably represents $C_1$–$C_{12}$-alkyl, $C_1$–$C_{12}$-alkoxy, $C_2$–$C_{12}$-alkenyl, $C_2$–$C_{12}$-alkenyloxy, in each case optionally halogen-, $C_1$–$C_4$-alkyl-, $C_2$–$C_4$-alkenyl-, $C_1$–$C_4$-halogenoalkyl- or $C_2$–$C_4$-halogenoalkenyl-substituted $C_3$–$C_8$-cycloalkyl, $C_3$–$C_8$-cycloalkyloxy or $C_3$–$C_8$-cycloalkyl-$C_1$–$C_6$-alkyloxy or represents phenyl or naphthyl which is in each case optionally mono- to tetrasubstituted by nitro, halogen, $C_1$–$C_{12}$-alkyl, $C_1$–$C_{12}$-alkoxy, $C_1$–$C_{12}$-halogenoalkyl or $C_1$–$C_{12}$-halogenoalkoxy.

$R^7$ preferably represents hydrogen or $C_1$–$C_{12}$-alkyl.

$R^8$ preferably represents $C_1$–$C_{12}$-alkyl, $C_1$–$C_{12}$-halogenoalkyl, in each case optionally halogen-, $C_1$–$C_4$-alkyl-, $C_2$–$C_4$-alkenyl-, $C_1$–$C_4$-halogenoalkyl- or $C_2$–$C_4$-halogenoalkenyl-substituted $C_3$–$C_8$-cycloalkyl or $C_3$–$C_8$-cycloalkyl-$C_1$–$C_6$-alkyl or represents phenyl or phenyl-$C_1$–$C_6$-alkyl, each of which is optionally mono- to tetrasubstituted by halogen, $C_1$–$C_{12}$-alkyl, $C_1$–$C_{12}$-alkoxy, $C_1$–$C_{12}$-halogenoalkyl or $C_1$–$C_{12}$-halogenoalkoxy.

p, q and r independently of one another each preferably represent 0, 1, 2 or 3, their sum being smaller than 6 and greater than 1.

$R^9$ and $R^{10}$ independently of one another each preferably represent hydrogen or $C_1$–$C_4$-alkyl.

G preferably represents cyano, represents a 5- or 6-membered heterocycle having 1 to 3 identical or different heteroatoms from the group consisting of nitrogen, oxygen and sulphur (in particular 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl) and being optionally mono- to trisubstituted by halogen, $C_1$–$C_4$-alkyl or $C_1$–$C_4$-halogenoalkyl and optionally, at the point of linkage, by the radical $R^{11}$, or represents one of the following groupings:
(a) —CO—$R^{11}$
(b) —CO—$OR^{12}$ (c) —CO—NR$^{13}$R$^{14}$ (d) —CS—NR$^{13}$R$^1$ (e) 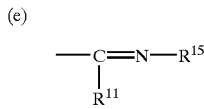

(f) 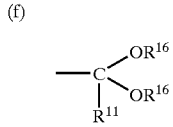

(g) 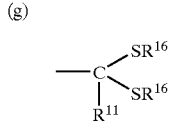

(h) 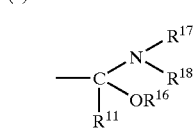

(i) 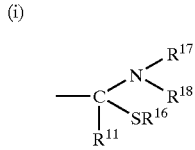

(j) 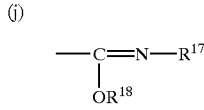

(k) 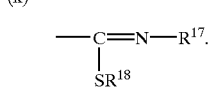

R$^{11}$ preferably represents hydrogen, C$_1$–C$_6$-alkyl, C$_2$–C$_6$-alkenyl, C$_1$–C$_4$-halogenoalkyl, C$_2$–C$_6$-halogenoalkenyl, optionally halogen-, C$_1$–C$_4$-alkyl- or C$_1$–C$_4$-halogenoalkyl-substituted C$_3$–C$_6$-cycloalkyl or represents phenyl which is optionally mono- to pentasubstituted by C$_1$–C$_4$-alkylcarbonylamino, C$_1$–C$_4$-alkylcarbonyl-C$_1$–C$_4$-alkylamino and/or radicals from the list W$^3$.

R$^{12}$ preferably represents hydrogen, C$_1$–C$_4$-alkyl, C$_2$–C$_6$-alkenyl, C$_1$–C$_4$-halogenoalkyl, C$_2$–C$_6$-halogenoalkenyl, in each case optionally halogen-, C$_1$–C$_4$-alkyl- or C$_1$–C$_4$-halogenoalkyl-substituted C$_3$–C$_6$-cycloalkyl or C$_3$–C$_6$-cycloalkyl-C$_1$–C$_4$-alkyl or represents C$_6$–C$_{10}$-aryl-C$_1$–C$_4$-alkyl (in particular phenyl-C$_1$–C$_4$-alkyl or naphthyl-C$_1$–C$_4$-alkyl) which is optionally mono- to tetrasubstituted by radicals from the list W$^3$.

R$^{13}$ and R$^{14}$ independently of one another each preferably represent hydrogen, C$_1$–C$_4$-alkyl, C$_3$–C$_6$-alkenyl, C$_1$–C$_4$-halogenoalkyl, C$_3$–C$_6$-halogenoalkenyl, C$_1$–C$_4$-alkoxy, in each case optionally halogen-, C$_1$–C$_4$-alkyl- or C$_1$–C$_4$-halogenoalkyl-substituted C$_3$–C$_6$-cycloalkyl or C$_3$–C$_6$-cycloalkyl-C$_1$–C$_4$-alkyl, represent phenyl or phenyl-C$_1$–C$_4$-alkyl, each of which is optionally mono- to pentasubstituted by radicals from the list W$^3$, represent —OR$^{12}$ or —NR$^{11}$R$^{12}$ or together represent an alkylene chain having 4 to 6 members in which optionally one methylene group is replaced by oxygen.

R$^{15}$ preferably represents —OR$^{12}$, —NR$^{11}$R$^{12}$ or —N(R$^{11}$)—COOR$^{12}$.

R$^{16}$, R$^{17}$ and R$^{18}$ independently of one another each preferably represent C$_1$–C$_6$-alkyl.

W$^1$ preferably represents hydrogen, halogen, cyano, formyl, nitro, C$_1$–C$_6$-alkyl, tri-C$_1$–C$_4$-alkylsilyl, C$_1$–C$_{16}$-alkoxy, C$_1$–C$_6$-halogenoalkyl, C$_1$–C$_6$-halogenoalkoxy, C$_2$–C$_6$-halogenoalkenyloxy, C$_1$–C$_6$-alkylcarbonyl, C$_1$–C$_{16}$-alkoxycarbonyl, pentafluorothio or —S(O)$_O$R$^3$.

W$^2$ preferably represents halogen, cyano, formyl, nitro, C$_1$–C$_6$-alkyl, tri-C$_1$–C$_4$-alkylsilyl, C$_1$–C$_{16}$-alkoxy, C$_1$–C$_6$-halogenoalkyl, C$_1$–C$_6$-halogenoalkoxy, C$_1$–C$_6$-alkylcarbonyl, C$_1$–C$_{16}$-alkoxycarbonyl, pentafluorothio, —S(O)$_O$R$^3$ or —C(R$^{11}$)=N—R$^{15}$.

W$^3$ preferably represents halogen, cyano, nitro, C$_1$–C$_4$-alkyl, C$_1$–C$_4$-alkoxy, C$_1$–C$_4$-halogenoalkyl, C$_1$–C$_4$-halogenoalkoxy, di-C$_1$–C$_4$-alkylamino, —S(O)$_O$R$^3$, —COOR$^{19}$ or —CONR$^{20}$R$^{21}$.

R$^{19}$ preferably represents hydrogen, C$_1$–C$_4$-alkyl, C$_1$–C$_4$-halogenoalkyl, optionally halogen-, C$_1$–C$_4$-alkyl- or C$_1$–C$_4$-halogenoalkyl-substituted C$_3$–C$_7$-cycloalkyl or represents phenyl which is optionally mono- to pentasubstituted by radicals from the list W$^4$.

R$^{20}$ and R$^{21}$ independently of one another each preferably represent hydrogen, C$_1$–C$_4$-alkyl, C$_3$–C$_6$-alkenyl, C$_1$–C$_4$-halogenoalkyl, C$_3$–C$_6$-halogenoalkenyl, C$_1$–C$_4$-alkoxy, in each case optionally halogen-, C$_1$–C$_4$-alkyl- or C$_1$–C$_4$-halogenoalkyl-substituted C$_3$–C$_6$-cycloalkyl or C$_3$–C$_6$-cycloalkyl-C$_1$–C$_4$-alkyl or represent phenyl or phenyl-C$_1$–C$_4$-alkyl, each of which is optionally mono- to pentasubstituted by radicals from the list W$^4$, represent —OR$^{16}$ or —NR$^{17}$R$^{18}$ or together represent an alkylene chain having 4 to 6 members in which optionally one methylene group is replaced by oxygen.

W$^4$ preferably represents halogen, cyano, nitro, C$_1$–C$_6$-alkyl, C$_1$–C$_6$-alkoxy, C$_1$–C$_6$-halogenoalkyl, C$_1$–C$_6$-halogenoalkoxy, di-C$_1$–C$_4$-alkylamino, C$_1$–C$_6$-alkoxycarbonyl, di-C$_1$–C$_6$-alkylaminocarbonyl or —S(O)$_O$R$^3$.

Ar particularly preferably represents the radical

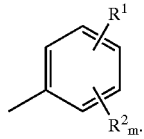

m particularly preferably represents 0, 1 or 2.

R$^1$ particularly preferably represents a substituent in the meta or para position from the group consisting of hydrogen, fluorine, chlorine, bromine, cyano, tri-(C$_1$–C$_4$-alkyl)-silyl, —CO—NR$^4$R$^5$, tetrahydropyranyl or one of the following groupings (l) —X—A (m) —B—Z—D (n) —Y—E.

R$^2$ particularly preferably represents hydrogen, fluorine, chlorine, bromine, iodine, cyano, nitro, C$_1$–C$_{16}$-alkyl, C$_1$–C$_{16}$-alkoxy, in each case fluorine- or chlorine-substituted C$_1$–C$_6$-alkyl or C$_1$–C$_6$-alkoxy, represents C$_1$–C$_8$-alkoxy-C$_1$–C$_8$-alkoxy or —S(O)$_O$R$^3$.

with the proviso that R$^1$ does not represent hydrogen if m=1 and R$^2$=iodine.

o particularly preferably represents 0, 1 or 2.

$R^3$ particularly preferably represents $C_1$–$C_4$-alkyl or in each case fluorine- or chlorine-substituted methyl or ethyl.

$R^4$ and $R^5$ independently of one another each particularly preferably represent hydrogen, $C_1$–$C_6$-alkyl, fluorine- or chlorine-substituted $C_1$–$C_6$-alkyl or represent phenyl or benzyl, each of which is optionally mono- or disubstituted by radicals from the list $W^1$.

X particularly preferably represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_{1-4}$-alkylenoxy, $C_1$–$C_4$-oxyalkylene, $C_1$–$C_4$-thioalkylene, $C_1$–$C_4$-alkylenedioxy or di-$C_1$–$C_4$-alkylsilylene.

A particularly preferably represents phenyl, naphthyl or tetrahydronaphthyl, each of which is optionally mono- to trisubstituted by radicals from the list $W^1$, or represents 5- to 10-membered heterocyclyl containing one or two aromatic rings and having 1 to 4 heteroatoms which contains 0 to 4 nitrogen atoms, 0 to 2 oxygen atoms and 0 to 2 sulphur atoms (in particular furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl) and is in each case optionally mono- to trisubstituted by radicals from the list $W^2$.

B particularly preferably represents p-phenylene which is optionally mono- or disubstituted by radicals from the list $W^1$.

Z particularly preferably represents oxygen or sulphur.

D particularly preferably represents hydrogen, $C_1$–$C_{16}$-alkyl, $C_2$–$C_{16}$-alkenyl, $C_2$–$C_6$-alkinyl, in each case fluorine- or chlorine-substituted $C_1$–$C_4$-alkyl or $C_2$–$C_4$-alkenyl, represents $C_3$–$C_6$-cycloalkyl or $C_3$–$C_6$-cycloalkyl-$C_1$–$C_4$-alkyl, each of which is optionally substituted by fluorine, chlorine, bromine, $C_1$–$C_4$-alkyl, $C_2$–$C_4$-alkenyl, by fluorine- or chlorine-substituted $C_2$–$C_4$-alkenyl, by phenyl, styryl, in each case fluorine-, chlorine- or bromine-substituted phenyl or styryl, represents in each case optionally fluorine-, chlorine-, bromine- or $C_1$–$C_4$-alkyl-substituted $C_5$–$C_6$-cycloalkenyl or $C_5$–$C_6$-cycloalkenyl-$C_1$–$C_4$-alkyl, represents phenyl-$C_1$–$C_4$-alkyl, napthyl-$C_1$–$C_4$-alkyl, tetrahydronaphthyl-$C_1$–$C_6$-alkyl or hetaryl-$C_1$–$C_4$-alkyl having 5 or 6 ring members and one or two heteroatoms from the group consisting of nitrogen, oxygen and sulphur (in particular furylmethyl, thienylmethyl, pyrrolylmethyl, oxazolylmethyl, isoxazolylmethyl, thioazolylmethyl or pyridylmethyl), each of which is optionally substituted by nitro, fluorine, chlorine, bromine, $C_1$–$C_6$-alkyl, $C_1$–$C_6$-alkoxy, in each case fluorine- or chlorine-substituted $C_1$–$C_4$-alkyl or $C_1$–$C_4$-alkoxy, represents —CO—$R^6$, —CO—$NR^7R^8$ or the grouping —$(CH_2)_p$—$(CR^9R^{10})_q$—$(CH_2)_r$—G.

Z and D together also particularly preferably represent substituted phenoxy-$C_1$–$C_3$-alkyl which is optionally substituted by niitro, fluorine, chlorine, bromine, $C_1$–$C_4$-alkyl, $C_1$–$C_4$-alkoxy, in each case fluorine- or chlorine-substituted $C_1$–$C_4$-alkyl or $C_1$–$C_4$-alkoxy.

Y particularly preferably represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylenedioxy or represents p-phenylene which is optionally mono- or disubstituted by radicals from the list $W^1$.

E particularly preferably represents hydrogen, $C_1$–$C_{16}$-alkyl, $C_2$–$C_{16}$-alkenyl, $C_2$–$C_6$-alkinyl, in each case fluorine- or chlorine-substituted $C_1$–$C_4$-alkyl or $C_2$–$C_4$-alkenyl, represents $C_3$–$C_6$-cycloalkyl which is optionally substituted by fluorine, chlorine, bromine, $C_1$–$C_4$-alkyl, $C_2$–$C_4$-alkenyl, by fluorine- or chlorine-substituted $C_2$–$C_4$-alkenyl, by phenyl, styryl or in each case fluorine-, chlorine- or bromine-substituted phenyl or styryl, represents optionally fluorine-, chlorine-, bromine- or $C_1$–$C_4$-alkyl-substituted $C_5$–$C_6$-cycloalkenyl, represents phenyl which is optionally mono- to trisubstituted by radicals from the list $W^1$ or represents 5- or 6-membered hetaryl having 1 or 2 heteroatoms from the group consisting of nitrogen, oxygen and sulphur (in particular furyl, thienyl, pyrrolyl, oxazolyl, isoxazolyl, thiazolyl or pyridyl), each of which is optionally mono- or disubstituted by radicals from the list $W^2$, or represents the grouping —$(CH_2)_p$—$(CR^9R^{10})_q$—$(CH_2)_r$—G.

$R^6$ particularly preferably represents $C_1$–$C_6$-alkyl, $C_1$–$C_6$-alkoxy, $C_2$–$C_6$-alkenyl, $C_2$–$C_6$-alkenyloxy, represents $C_3$–$C_6$-cycloalkyl, $C_3$–C6-cycloalkyloxy or $C_3$–$C_6$-cycloalkyl-$C_1$–$C_2$-alkyloxy, each of which is optionally substituted by fluorine, chlorine, $C_1$–$C_3$-alkyl or in each case fluorine- or chlorine-substituted $C_1$–$C_2$-alkyl or $C_2$–$C_3$-alkenyl, or represents phenyl which is optionally mono- or disubstituted by fluorine, chlorine, bromine, iodine, $C_1$–$C_4$-alkyl, $C_1$–$C_4$-alkoxy or by in each case fluorine- or chlorine-substituted $C_1$–$C_3$-alkyl or $C_1$–$C_4$-alkoxy.

$R^7$ particularly preferably represents hydrogen or $C_1$–$C_4$-alkyl.

$R^8$ particularly preferably represents $C_1$–$C_4$-alkyl or represents phenyl or benzyl, each of which is optionally mono- or disubstituted by fluorine, chlorine, bromine, $C_1$–$C_4$-alkyl or by in each case fluorine- or chlorine-substituted $C_1$–$C_4$-alkyl or $C_1$–$C_4$-alkoxy.

p, q and r independently of one another each particularly preferably represent 0, 1, 2 or 3, their sum being smaller than 6 and greater than 1.

$R^9$ and $R^{10}$ independently of one another each particularly preferably represent hydrogen or $C_1$–$C_4$-alkyl.

G particularly preferably represents cyano, represents a 5- or 6-membered heterocycle having 1 to 3 identical or different heteroatoms from the group consisting of nitrogen, oxygen and sulphur (in particular 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl) and being optionally mono- to trisubstituted by fluorine, chlorine, bromine, $C_1$–$C_4$-alkyl or by fluorine- or chlorine-substituted $C_1$–$C_4$-alkyl and optionally, at the point of linkage, by the radical $R^{11}$, or represents one of the following groupings:

(a) —CO—$R^{11}$
(b) —CO—$OR^{13}R^{12}$
(c) —CO—$NR^{13}R^{14}$
(d) —CS—$NR^{13}R^{14}$ (e) 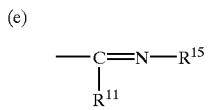

(f) 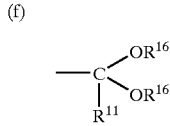

(g) 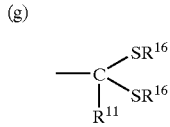

(h) 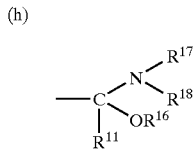

(i) 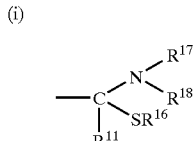

(j) 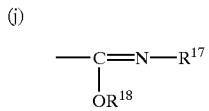

(k) 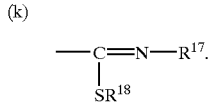

$R^1$ particularly preferably represents hydrogen, $C_1$–$C_6$-alkyl, $C_2$–$C_6$-alkenyl, in each case fluorine- or chlorine-substituted $C_1$–$C_4$-alkyl or $C_2$–$C_6$-alkenyl, represents $C_3$–$C_6$-cycloalkyl which is optionally substituted by fluorine, chlorine, $C_1$–$C_4$-alkyl or by fluorine- or chlorine-substituted $C_1$–$C_4$-alkyl, or represents phenyl which is optionally mono- to trisubstituted by $C_1$–$C_4$-alkylcarbonylamino, $C_1$–$C_4$-alkylcarbonyl-$C_1$–$C_4$-alkylamino and/or radicals from the list $W^3$.

$R^{12}$ particularly preferably represents hydrogen, $C_1$–$C_4$-alkyl, $C_3$–$C_6$-alkenyl, in each case fluorine- or chlorine-substituted $C_1$–$C_4$-alkyl or $C_3$–$C_6$-alkenyl, represents $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl or by fluorine- or chlorine-substituted $C_1$–$C_4$-alkyl, or represents phenyl-$C_1$–$C_4$-alkyl or naphthyl-$C_1$–$C_4$-alkyl, each of which is optionally mono- to trisubstituted by radicals from the list $W^3$.

$R^{13}$ and $R^{14}$ independently of one another each particularly preferably represent hydrogen, $C_1$–$C_4$-alkyl, $C_3$–$C_6$-alkenyl, in each case fluorine- or chlorine-substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl or by fluorine- or chlorine-substituted $C_1$–$C_4$-alkyl, represent phenyl or phenyl-$C_1$–$C_4$-alkyl, each of which is optionally mono- to trisubstituted by radicals from the list $W^3$, represent —$OR^{12}$ or —$NR^{11}R^{12}$ or together represent —$(CH_2)_5$—, —$(CH_2)_6$— or —$(CH_2)_2$—O—$(CH_2)_2$—.

$R^{15}$ particularly preferably represents —$OR^{12}$, —$NR^{11}R^{12}$ or —$N(R^{11})$—$COOR^{12}$.

$R^{16}$, $R^{17}$ and $R^{18}$ independently of one another each particularly preferably represent $C_1$–$C_4$-alkyl.

$W^1$ particularly preferably represents hydrogen, fluorine, chlorine, bromine, iodine, cyano, formyl, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl or —$S(O)_OR^3$.

$W^2$ particularly preferably represents fluorine, chlorine, bromine, cyano, formyl, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl, —$S(O)_OR^3$ or —$C(R^{11})$=N—$R^{15}$.

$W^3$ particularly preferably represents fluorine, chlorine, bromine, cyano, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, represents di-$C_1$–$C_4$-alkylamino, —$S(O)_OR^3$, —$COOR^{19}$ or —$CONR^{20}R^{21}$.

$R^{19}$ particularly preferably represents hydrogen, $C_1$–$C_4$-alkyl, fluorine- or chlorine-substituted $C_1$–$C_4$-alkyl, represents $C_3$–$C_6$-cycloalkyl which is optionally substituted by fluorine, chlorine, $C_1$–$C_4$-alkyl or by fluorine- or chlorine-substituted $C_1$–$C_4$-alkyl, or represents phenyl, which is optionally mono- to trisubstituted by radicals from the list $W^4$.

$R^{20}$ and $R^{21}$ independently of one another each particularly preferably represent hydrogen, $C_1$–$C_4$-alkyl, $C_3$–$C_6$-alkenyl, in each case fluorine- or chlorine-substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl or by fluorine- or chlorine-substituted-$C_1$–$C_4$-alkyl, or represent phenyl or phenyl-$C_1$–$C_4$-alkyl, each of which is optionally mono- to trisubstituted by radicals from the list $W^4$, represent —$OR^{16}$ or —$NR^{17}R^{18}$ or together represent —$(CH_2)_5$—, —$(CH_2)_6$— or —$(CH_2)_2$—O—$(CH_2)_2$—.

$W^4$ particularly preferably represents fluorine, chlorine, bromine, cyano, nitro, $C_1$–$C_4$-alkyl, $C_1$–$C_4$-alkoxy, in each case fluorine- or chlorine-substituted $C_1$–$C_4$-alkyl or $C_1$–$C_4$-alkoxy, di-$C_1$–$C_4$-alkylamino, $C_1$–$C_4$-alkoxycarbonyl, di-$C_1$–$C_6$-alkylaminocarbonyl or —$S(O)_OR^3$.

Ar very particularly preferably represents the radical

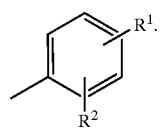

$R^1$ very particularly preferably represents a substituent in the meta or para position from the group consisting of hydrogen, fluorine, chlorine, bromine, cyano, —CO—$NR^4R^5$, tetrahydropyranyl or one of the groupings below

—X—A (1)

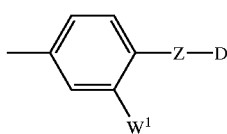 (m-a)

—Y—E (n)

R² very particularly preferably represents hydrogen, fluorine, chlorine, bromine, iodine, methyl, ethyl, methoxy, ethoxy, methylthio, ethylthio, trifluoromethyl, difluoromethoxy, trifluoromethoxy or trifluormethylthio with the proviso that $R^1$ does not represent hydrogen if m=1 and $R^2$=iodine.

o very particularly preferably represents 0 or 2.

R³ very particularly preferably represents methyl, ethyl, n-propyl, isopropyl, difluoromethyl or trifluoromethyl.

R⁴ and R⁵ independently of one another each very particularly preferably represent hydrogen, methyl, ethyl, n-propyl, isopropyl, n-butyl, isobutyl, sec-butyl, tert-butyl or represent phenyl or benzyl, each of which is optionally monosubstituted by a radical from the list $W^1$.

X very particularly preferably represents a direct bond, oxygen, sulphur, carbonyl, —CH₂—, —(CH₂)₂—, —CH=CH—(E or Z), —C—C·, —CH₂O—, —(CH₂)₂O—, —CH(CH₃)O—, —OCH₂—, —O(CH₂)₂—, —SCH₂—, —S(CH₂)₂—, —SCH(CH₃)—, $C_1$-$C_4$-alkylenedioxy, in particular —OCH₂O—, —O(CH₂)₂O— or —OCH(CH₃)O—.

A very particularly preferably represents phenyl which is optionally mono- or disubstituted by radicals from the list $W^1$ or represents furyl, benzofuryl, thienyl, benzothienyl, oxazolyl, benzoxazolyl, thiazolyl. benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl, each of which is optionally mono- or disubstituted by radicals from the list $W^2$.

Z very particularly preferably represents oxygen or sulphur.

D very particularly preferably represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butinyl, pentinyl, —CF₃, —CHF₂, —CClF₂, —CF₂CHFCl, —CF₂CH₂F, —CF₂CHF₂, —CF₂CCl₃, —CH₂CF₃, —CF₂CHFCF₃, —CH₂CF₂CHF₂, —CH₂CF₂CF₃, represents cyclopropyl, cyclobutyl, cyclopentyl, cyclohexyl, cyclopropylmethyl, cyclobutylmethyl, cyclopentylmethyl or cyclohexylmethyl, each of which is optionally mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH=CCl₂, phenyl, styryl, in each case fluorine-, chlorine- or bromine-substituted phenyl or 4-chlorostyryl, represents cyclopentenyl, cyclohexenyl, cyclohexenylmethyl or cyclopentenylmethyl, each of which is optionally substituted by fluorine, chlorine, methyl, ethyl, n-propyl, isopropyl, n-butyl, isobutyl, sec-butyl or tert-butyl, represents benzyl, phenethyl, naphthylmethyl, tetrahydronaphthylmethyl, furylmethyl, thienylmethyl, pyrrolylmethyl, oxazolylmethyl, isoxazolylmethyl, thiazolylmethyl or pyridylmethyl, each of which is optionally mono- or disubstituted by nitro, fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, trifluoromethyl, trifluoromethoxy, difluoromethoxy or chlorodifluoromethoxy, represents —CO—R⁶, —CO—NR⁷R⁸ or the grouping —(CH₂)$_p$—(CR⁹R¹⁰)$_q$—(CH₂)$_r$—G.

Z and D together also very particularly preferably represent phenoxymethyl which is optionally mono- or disubstituted by nitro, fluorine, chlorine, bromine, methyl, ethyl, n-propyl, i-propyl, methoxy, ethoxy, n-propoxy, i-propoxy, trifluoromethyl, trifluoromethoxy, difluoromethoxy or chlorodifluoromethoxy.

Y very particularly preferably represents a direct bond, oxygen, sulphur, carbonyl, —CH₂—, —(CH₂)₂—, —CH=CH— (E or Z), —C≡C—, —CH₂O—, —(CH₂)₂O—, —CH(CH₃)O—, —OCH₂—, —O(CH₂)₂—, —SCH₂—, —S(CH₂)₂—, —SCH(CH₃)—, $C_1$-$C_4$-alkylenedioxy, in particular —OCH₂O— or —O(CH₂)₂O— or represents p-phenylene which is optionally monosubstituted by a radical from the list $W^1$.

E very particularly preferably represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butinyl, pentinyl, —CF₃, —CHF₂, —CClF₂, —CF₂CHFCl, —CF₂CH₂F, —CF₂CHF₂, —CF₂CCl₃, —CH₂CF₃, —CF₂CHFCF₃, —CH₂CF₂CHF₂, —CH₂CF₂CF₃, represents cyclopropyl, cyclobutyl, cyclopentyl or cyclohexyl, each of which is optionally mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH=CCl₂, phenyl, styryl, in each case fluorine-, chlorine- or bromine-substituted phenyl or by 4-chlorostyryl, represents cyclopentenyl or cyclohexenyl, each of which is optionally substituted by fluorine, chlorine, methyl, ethyl, n-propyl, isopropyl, n-butyl, isobutyl, sec-butyl or tert-butyl, represents phenyl which is optionally mono- or disubstituted by radicals from the list $W^1$, represents furyl, thienyl, pyrrolyl, oxazolyl, isoxazolyl, thiazolyl or pyridyl, each of which is optionally mono- or disubstituted by radicals from the list $W^2$, or represents the grouping
—(CH₂)$_p$—(CR⁹R¹⁰)$_q$—(CH₂)$_r$—G.

R⁶ very particularly preferably represents methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, cyclopropyl, cyclohexyl, cyclohexyloxy, cyclohexylmethyloxy, phenyl, 2-chlorophenyl, 3-chlorophenyl, 2,6-difluorophenyl, 2,4-dichlorophenyl, 3,4-dichlorophenyl, 2-trifluoromethoxyphenyl or 4-trifluoromethoxyphenyl.

$R^7$ very particularly preferably represents hydrogen.

$R^8$ very particularly preferably represents methyl, ethyl or phenyl which is optionally monosubstituted by chlorine.

p, q and r independently of one another each very particularly preferably represent 0, 1, 2 or 3, their sum being smaller than 4 and greater than 1.

$R^9$ and $R^{10}$ independently of one another each very particularly preferably represent hydrogen, methyl, ethyl, n-propyl, isopropyl, n-butyl, isobutyl, sec-butyl, tert-butyl.

G very particularly preferably represents cyano, represents 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl, each of which is optionally mono- to trisubstituted by fluorine, chlorine, bromine, methyl, ethyl, n-propyl, isopropyl or trifluoromethyl and optionally, at the point of linkage, by the radical $R^{11}$, or represents one of the groupings below:

(a) —CO—$R^{11}$
(b) —CO—$OR^{12}$
(c) —CO—$NR^{13}R^{14}$
(d) —CS—$NR^{13}R^{14}$ (e)
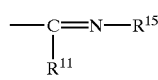

(f)
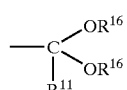

(g)
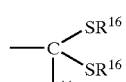

(h)
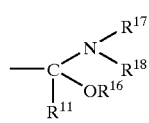

(i)
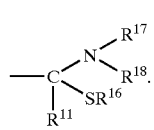

$R^{11}$ very particularly preferably represents hydrogen, methyl, ethyl, n-propyl, isopropyl, n-butyl, isobutyl, sec-butyl, tert-butyl, the isomeric pentyls, the isomeric hexyls, —$CF_3$, —$CHF_2$, —$CClF_2$, —$CF_2CHFCl$, —$CF_2Cl_2F$, —$CF_2CHF_2$, —$CF_2CCl_3$, —$CH_2CF_3$, $C_3$–$C_6$-alkenyl, $C_3$–$C_6$-alkenyl which is mono- to trisubstituted by fluorine or chlorine, represents cyclopropyl, cyclopentyl or cyclohexyl, each of which is optionally mono- or disubstituted by fluorine, chlorine, methyl, ethyl, n-propyl, isopropyl, —$CF_3$, —$CHF_2$, —$CClF_2$, —$CF_2CHFCl$, —$CF_2CH_2F$, —$CF_2CHF_2$, —$CF_2CCl_3$ or —$CH_2CF_3$, or represents phenyl which is optionally mono- or disubstituted by methylcarbonylamino, ethylcarbonylamino, methylcarbonyl-methylamino and/or radicals from the list $W^3$.

$R^{12}$ very particularly preferably represents hydrogen, methyl, ethyl, n-propyl, isopropyl, n-butyl, isobutyl, sec-butyl, tert-butyl, —$CH_2CF_3$, allyl, represents cyclopropyl, cyclopentyl, cyclohexyl, cyclopropylmethyl, cyclopentylmethyl, cyclohexylmethyl, cyclopropylethyl, cyclopentylethyl or cyclohexylethyl, each of which is optionally mono- or disubstituted by fluorine, chlorine, methyl, ethyl, n-propyl, isopropyl, —$CF_3$, —$CHF_2$, —$CClF_2$, —$CF_2CHFCl$, —$CF_2CH_2F$, —$CF_2CHF_2$, —$CF_2CCl_3$ or —$CH_2CF_3$, or represents benzyl or phenethyl, each of which is optionally mono- or disubstituted by radicals from the list $W^3$.

$R^{13}$ and $R^{14}$ independently of one another each very particularly preferably represent hydrogen, methyl, ethyl, n-propyl, isopropyl, n-butyl, isobutyl, sec-butyl, tert-butyl, —$CH_2CF_3$, methoxy, ethoxy, allyl, represent cyclopropyl, cyclopentyl, cyclohexyl, cyclopropylmethyl, cyclopentylmethyl or cyclohexylmethyl, each of which is optionally mono- or disubstituted by fluorine, chlorine, methyl, ethyl, n-propyl, isopropyl or trifluoromethyl, represent phenyl, benzyl or phenethyl, each of which is optionally mono- or disubstituted by radicals from the list $W^3$, represent —$OR^{12}$ or —$NR^{11}R^{12}$.

$R^{15}$ very particularly preferably represents —$OR^{12}$, —$NR^{11}R^{12}$ or —$N(R^{11})$—$COOR^{12}$.

$R^{16}$, $R^{17}$ and $R^{18}$ independently of one another each very particularly preferably represent methyl, ethyl, n-propyl or isopropyl.

$W^1$ very particularly preferably represents hydrogen, fluorine, chlorine, bromine, cyano, formyl, nitro, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, —$CF_3$, —$CHF_2$, —$CClF_2$, —$CF_2CHFCl$, —$CF_2CH_2F$, —$CF_2CHF_2$, —$CF_2CCl_3$, —$CH_2CF_3$, —$CF_2CHFCF_3$, —$CH_2CF_2CHF_2$, —$CH_2CF_2CF_3$, tritluoromethoxy, difluoromethoxy, chlorodifluoromethoxy, acetyl, propionyl, butyryl, isobutyryl, meth-oxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl or —$S(O)OR^3$.

$W^2$ very particularly preferably represents fluorine, chlorine, bromine, cyano, methyl, ethyl, n-propyl, isopropyl, trifluoromethyl, trifluoromethoxy, difluoromethoxy, chlorodifluoromethoxy, acetyl, trifluoromethylthio, —CH=N—$OCH_3$, —CH=N—$OC_2H_5$, —CH=N—$OC_3H_7$, —$C(CH_3)$=N—$OCH_3$, —$C(CH_3)$=N—$OC_2H_5$, —$C(CH_3)$=N—$OC_3H_7$, —$C(C_2H_5)$=N—$OCH_3$, —$C(C_2H_5)$=N—$OC_2$—C$(C_2H_5)$=N—$OC_3H_7$ $W^3$ very particularly preferably represents fluorine, chlorine, cyano, nitro, methyl, ethyl, methoxy, ethoxy, methylthio, trifluoromethyl, trifluoromethoxy, trifluoromethylthio, dimethylamino, diethylamino, —$COOR^{19}$ or —$CONR^{20}R^{21}$.

$R^{19}$ very particularly preferably represents hydrogen, methyl, ethyl, n-propyl, isopropyl, tert-butyl, —$CH_2CF_3$, represents cyclopropyl, cyclopentyl or cyclohexyl, each of which is optionally mono- or disubstituted by fluorine, chlorine, methyl, ethyl, n-propyl, isopropyl or —$CF_3$, or represents phenyl which is optionally mono- or disubstituted by radicals from the list $W^4$.

$R^{20}$ and $R^{21}$ independently of one another each very particularly preferably represent hydrogen, methyl, ethyl, n-propyl, isopropyl, n-butyl, isobutyl, sec-butyl, tert-butyl, —CH$_2$CF$_3$, methoxy, ethoxy, allyl, represent cyclopropyl, cyclopentyl, cyclohexyl, cyclopropylmethyl, cyclopentylmethyl or cyclohexylmethyl, each of which is optionally mono- or disubstituted by fluorine or chlorine, represent phenyl, benzyl or phenethyl, each of which is optionally mono- or disubstituted by the radicals from the list W$^4$, represent —OR$^{16}$or —NR$^{17}$R$^{18}$ W$^4$ very particularly preferably represents fluorine, chlorine, bromine, cyano, nitro, methyl, ethyl, tert-butyl, methoxy, ethoxy, methylthio, trifluoromethyl, trifluoromethoxy or trifluoromethylthio.

Preference is furthermore given to compounds of the formula (I-a)

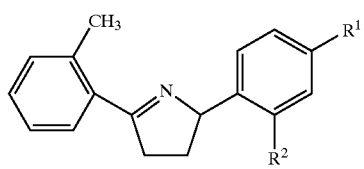

(I-a)

in which $R^2$ has the general, preferred, particularly preferred or very particularly preferred meanings mentioned above, $R^1$ represents hydrogen or phenyl which is mono- or disubstituted by radicals from the list W$^1$ or represents one of the groupings below (m-b) —B—O—D (l) —Y—E, B represents p-phenylene which is optionally monosubstituted by a radical from the list W$^1$, Y represents a direct bond or represents p-phenylene which is optionally mono- or disubstituted by radicals from the list W$^1$ and D and E each have the very particularly preferred meanings mentioned above, where G represents cyano or one of the groupings below (a) —CO—R$^{11}$

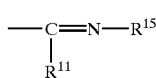

(e)

in which $R^{11}$ and $R^{15}$ each have the general, preferred, particularly preferred or very particularly preferred meanings mentioned above and W$^1$ has the general, preferred, particularly preferred or very particularly preferred meaning mentioned above.

Preference is furthermore given to compounds of the formula (I-f)

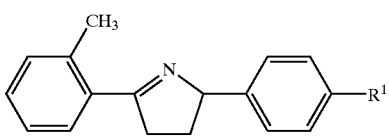

(I-f)

in which

R represents hydrogen or
a) phenyl which is mono- or disubstituted by radicals from the list W$^2$ or b) hetaryl (in particular furyl, thienyl, pyrrolyl, oxazolyl, isoxazolyl, thiazolyl or pyridyl, specifically thienyl) which is mono- or disubstituted by radicals from the list W$^2$.

Preference is furthermore given to compounds of the formula (I-g)

(I-g)

in which

Z represents hydrogen, fluorine, bromine, cyano, methyl, ethyl, n-propyl, isopropyl, trifluoromethyl, trifluoromethoxy, difluoromethoxy, chlorodifluoromethoxy, acetyl, trifluoromethylthio, —CH=N—OCH$_3$, —CH=N—OC$_2$H$_5$, —CH=N—OC$_3$H$_7$, —C(CH$_3$)=N—OCH$_3$, —C(CH$_3$)=NOC$_2$H$_5$, —C(CH$_3$)=N—OCt$_3$H$_7$, —C(C$_2$H$_5$)=N—OC$_2$H$_5$ or —C(C$_2$H$_5$)=N—OC$_3$H$_7$.

Preference is furthermore given to the compounds of the formula (I-f) listed in Table 1

TABLE 1

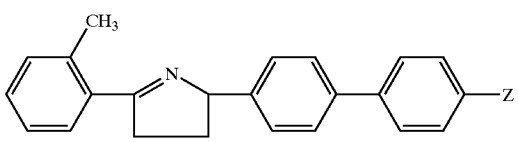

(1-f)

| Example No. | R$^1$ |
|---|---|
| I-1 | (CH$_2$)$_3$CH$_3$ |
| I-2 | ![structure: -C6H4-CH(CH3)2] |
| I-3 | ![structure: 3,5-dichlorophenyl] |
| I-4 | ![structure: 4-fluorophenyl] |

TABLE 1-continued
(1-f)
| Example No. | R¹ |
|---|---|
| I-5 | 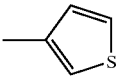 |
| I-6 | 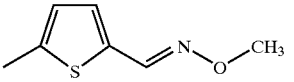 |
| I-7 | 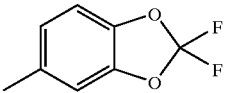 |
| I-8 | 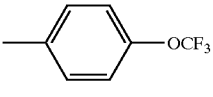 |
| I-9 | 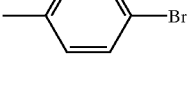 |
| I-10 | 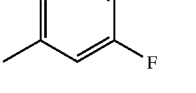 |
| I-11 | 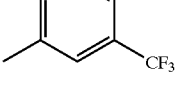 |
| I-12 | 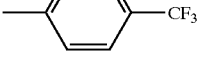 |
| I-13 | 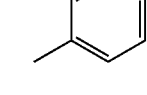 |
| I-14 | 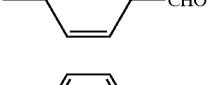 |
| I-15 | 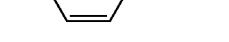 |
| I-16 | 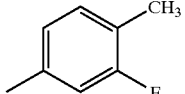 |
| I-17 | 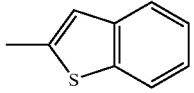 |
| I-18 | 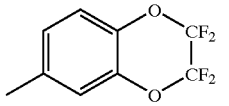 |
| I-19 | 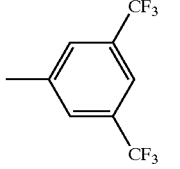 |
| I-20 | 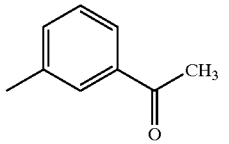 |
| I-21 | 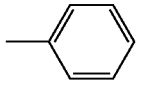 |
| I-22 | —H |
| I-23 | 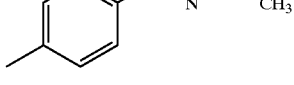 |
| I-24 | 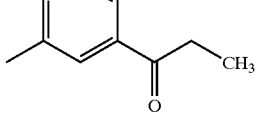 |
| I-25 | 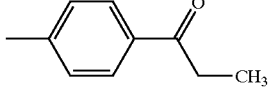 |
| I-26 | 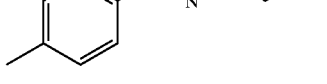 |
| I-27 | (shown) |

TABLE 1-continued

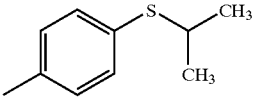

(1-f)

| Example No. | R¹ |
|---|---|
| I-28 | 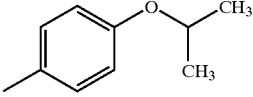 |
| I-29 | 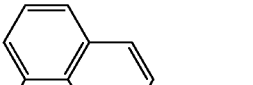 |
| I-30 | 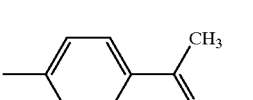 |
| I-31 |  |
| I-32 | 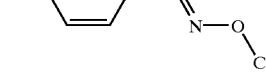 |
| I-33 | 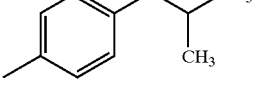 |
| I-34 | 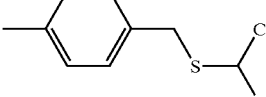 |
| I-35 | 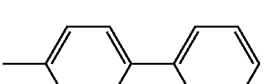 |
| I-36 | 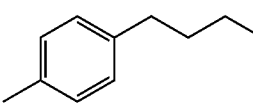 |
| I-37 | 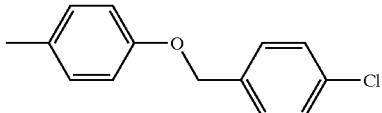 |

TABLE 1-continued

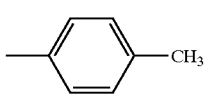

(1-f)

| Example No. | R¹ |
|---|---|
| I-38 | 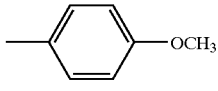 |
| I-39 | 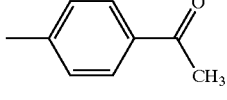 |
| I-40 | 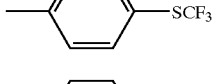 |
| I-41 | 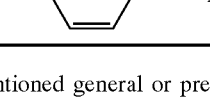 |
| I-42 | —⟨⟩—SCF₃ |
| I-43 | —⟨⟩—OCF₂CF₂H |

The abovementioned general or preferred radical definitions or illustrations can be combined with one another at will, i.e. including combinations between the respective ranges and preferred ranges. They apply both to the end products and also, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Saturated or unsaturated hydrocarbon radicals such as alkyl or alkenyl can in each case be straight-chain or branched as far as this is possible, even in combination with heteroatoms, such as, for example, in alkoxy.

Optionally substituted radicals can be mono- or polysubstituted and, in the case of polysubstitution, the substituents can be identical or different. A plurality of radicals having the same indices, such as, for example, m radicals R² for m>1, can be identical or different.

Using, for example, BOC-[1-(4-ethyl-2-methyl-phenyl)-3-(2-methylphenyl-carboxyl)-1-propyl]-amine as starting material, the course of the reaction of the process (A) a)

according to the invention can be represented by the following equation:

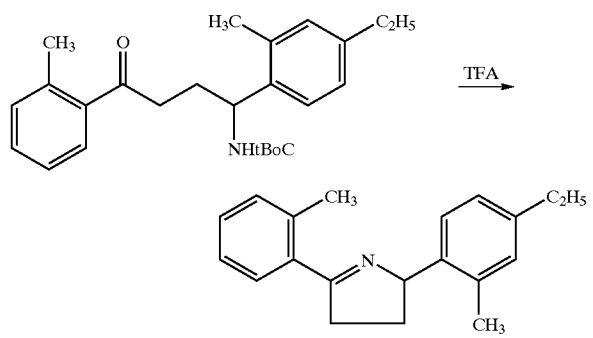

Using, for example, 1-(4-ethyl-2-methyl-phenyl)-1-nitro-3-(2-methylphenyl-carboxyl)-propane as starting material, the course of the reaction of the process (A) b) according to the invention can be represented by the following equation:

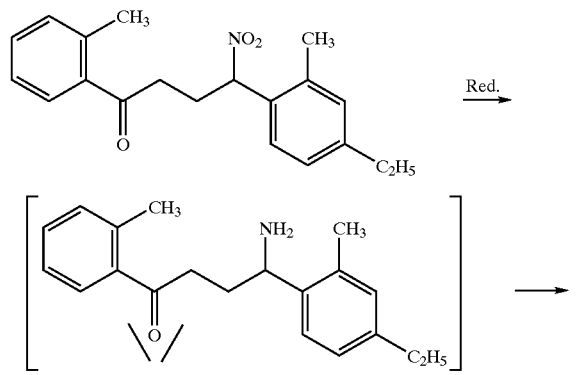

Using, for example, 1-(4-ethyl-2-methyl-phenyl)-1-(diphenylmethyleneimino)-3-(2-methylphenylcarboxyl)-propane as starting material, the course of the reaction of the process (A) c) according to the invention can be represented by the following equation:

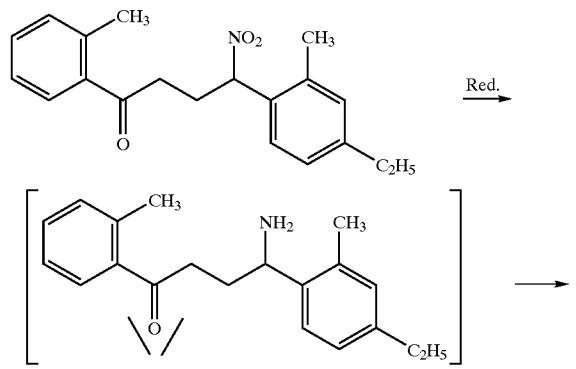

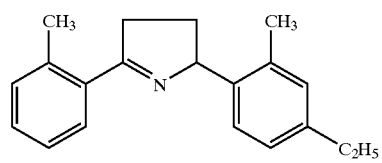

Using, for example, 2-(4-methoxyphenyl)-cyclobutane-O-methanesulfonyloxime and 2-tolylmagnesium bromide as starting materials, the course of the reaction of the process (B) according to the invention can be represented by the following equation:

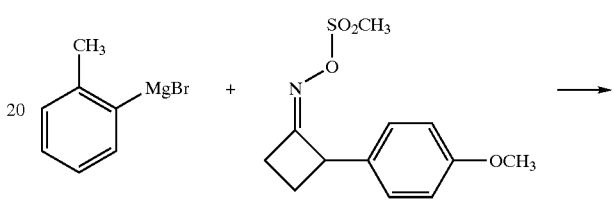

Using, for example, 2-(2-methylphenyl)-5-(4-iodophenyl)-3,4-dihydro-2H-pyrrole and 4-methoxyphenyl boronic acid as starting materials, the course of the reaction of the process (C) according to the invention can be represented by the following equation:

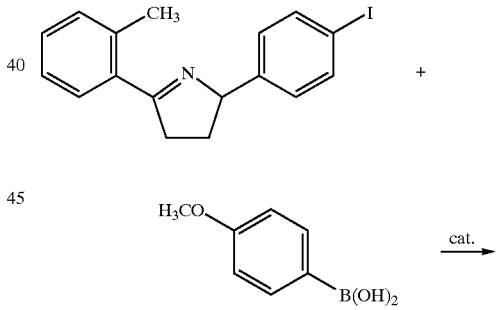

Using, for example, 2-(2-methyl-phenyl)-5-(3'-chloro-4'-hydroxybiphenyl-4-yl)-3,4-dihydro-2H-pyrrole and methyl α-bromovalerate as starting materials, the course of the reaction of the process (D) according to the invention can be represented by the following equation:

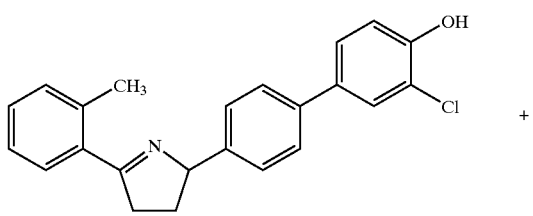

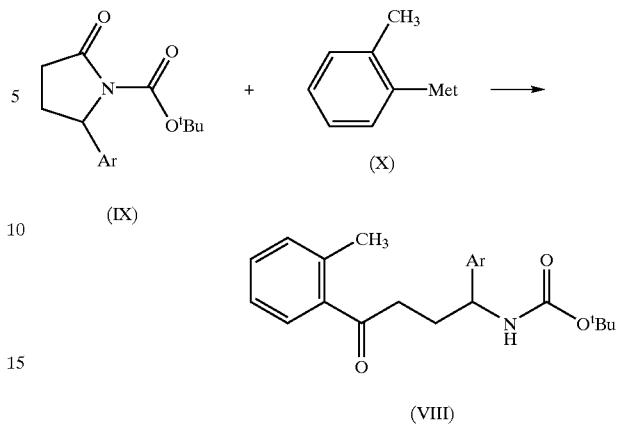

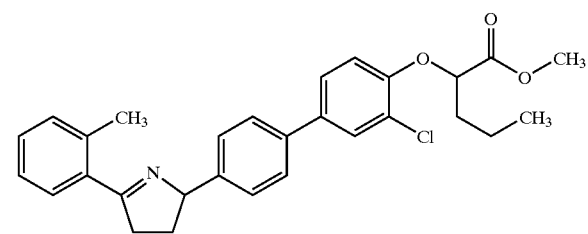

Using, for example, 5-(4'-cyclopropylcarbonylmethoxy-3-trifluoromethoxybiphenyl-4-yl)-2-(2-methylphenyl)-3,4-dihydro-2H-pyrrole and O-methylhydroxylamine as starting materials, the course of the reaction of the process (E) according to the invention can be represented by the following equation:

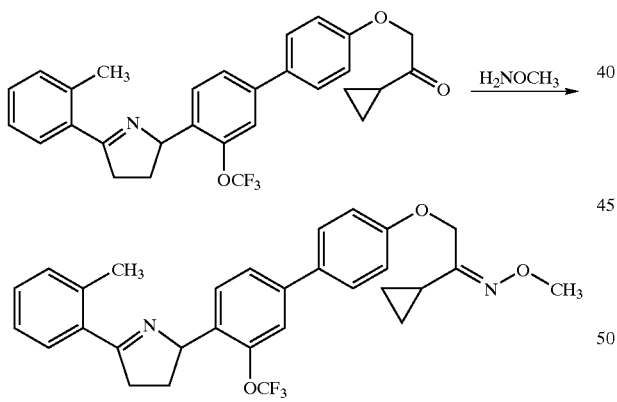

The formula (VIII) provides a general definition of the aminoketone derivatives required for carrying out the process (A) a) according to the invention. In this formula, Ar preferably has those meanings which have already been mentioned in connection with the description of the cyclic imines of the formula (I) as being preferred. The aminoketone derivatives of the formula (VM) are novel.

Aminoketone derivatives of the formula (VIII) can be prepared, for example, by reacting BOC-protected lactams of the formula (IX) with metallated aromatics of the formula (X) at temperatures between 0° C. and 80° C., in accordance with the following equation:

In the formula (X), Met represents a monovalent metal radical such as Li, Mgl, MgBr or MgCl.

Some metallated aromatics of the formula (X) are known, or they can be prepared by known methods, such as, for example, lithiation or Grignard reaction, from the corresponding aromatics or halogeno aromatics.

Protected lactams of the formula (IX) are obtained, for example, by BOC-protecting lactams of the formula (XI) using customary methods, such as, for example, metallation with butyl lithium and reaction with di-tert-butyl dicarbonate (cf., for example, T. W. Greene, P. G. M. Wuts, Protective Groups in Organic Synthesis, 2nd Ed., John Wiley & Sons, New York 1991).

Lactams of the formula (XI) can be prepared starting, for example, with balkoxylactams of the formula (XII), by two methods. The calkoxylactams can be reacted with aromatics of the formula (XII) in the presence of an acidic catalyst, such as, for example, sulphuric acid, acetic acid or aluminum chloride and, if appropriate, in the presence of a diluent, such as, for example, dichloromethane or acetonitrile, in accordance with the following equation:

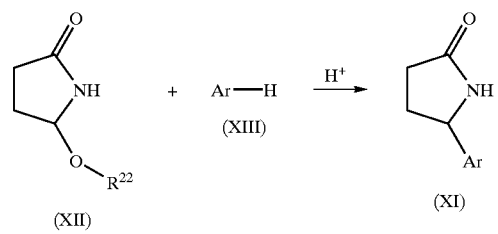

Alternatively, they can be reacted with aryl Grignard compounds of the formula (XIV) in the presence of a diluent, such as, for example, tetrahydrofuran, in accordance with the following equation [cf. Org. Prep. Proced. Int. 25, 255 (1993)]:

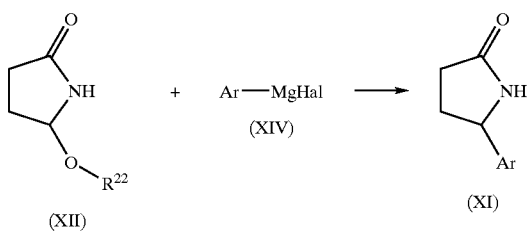

In formula (XII), $R^{22}$ represents methyl or ethyl. In the formula (XIV), Hal represents chlorine, bromine or iodine.

The ω-alkoxylactams of the formula (XII) are known, some of them are commercially available, and they can be prepared, for example, from the corresponding unsubstituted imides by cathodic or sodium borohydrite reduction, or from the unsubstituted lactams by anodic oxidation, in each case in the presence of methanol or ethanol (cf., for example, J. Org. Chem. 56, 1822 (1991); Synthesis 1980, 315).

The aromatics of the formula (XD) are benzene derivatives which are generally known or which can be prepared using a wide choice of generally known methods of organic chemistry.

The aryl Grignard compounds of the formula (XIV) can be prepared in a customary manner from the corresponding aryl halides and magnesium. Aryl halides are generally known compounds of organic chemistry.

Lactams of the formula (XI) can also be prepared, for example, by cyclizing substituted ω-benzoylcarboxylic acids of the formula (XV) with a reagent prepared from ammonium carbonate and formic acid at boiling point, in accordance with the following reaction scheme [cf. Recl. Trav. Chim. Pays-Bas 81, 788 (1962)]:

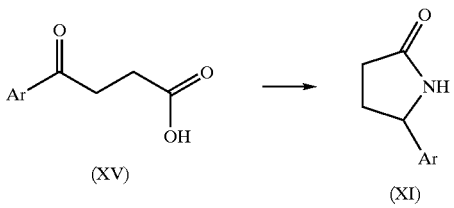

The ω-benzoylcarboxylic acids of the formula (XV) required for this purpose can be prepared, for example, by reacting the dicarboxylic anhydrides of the formula (XVI) with aromatics of the formula (XIII) in the presence of a Lewis acid, such as, for example, aluminium chloride, and, if appropriate, in the presence of a diluent, such as, for example, benzene, in accordance with the following equation [cf. Recl. Trav. Chim. Pays-Bas 81, 788 (1962)]:

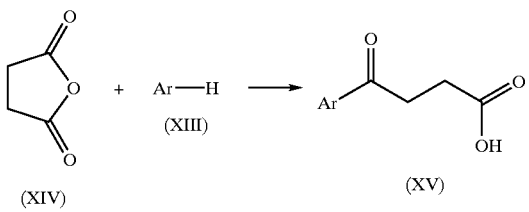

The anhydride (succinic anhydride) required for this purpose is commercially available.

Starting from the lactams of the formula (XI), all process steps up to the preparation of the cyclic imines of the formula (I), including the cyclocondensation according to process A a), can also be carried out as a "one-pot reaction" (see Example I-9 "One-pot variant").

If Ar in the active compound of the formula (I) according to the invention as in the formula (I-b) shown above represents an optionally substituted biphenylyl, the corresponding biphenyl lactams of the formula (XI-a) can be prepared in an advantageous variant of the process described here by reacting, similarly to the process (C) described above and below, certain phenyl lactams of the formula (XVII) with boronic acids of the formula (VI) in accordance with the following equation:

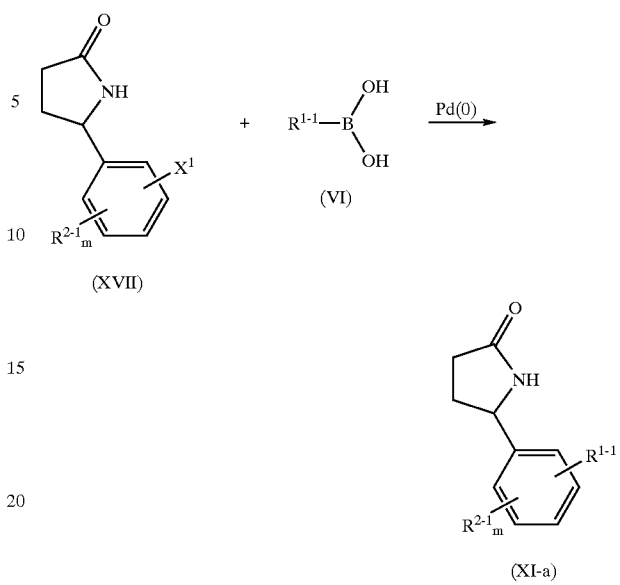

The phenyl lactams of the formula (XVII) in which $X^1$ represents bromine or iodine are a subset of the compounds of the formula (XI) whose preparation is mentioned above. The phenyl lactams of the formula (XVII) in which $X^1$ represents trifluoromethanesulphonyl can be prepared analogously to the route described for process (C) from the corresponding compounds of the formula (XI) in which Ar is substituted by $R^1$=hydroxyl.

The formula (XVIII) provides a general definition of the nitroketones required for carrying out the process A) b). In this formula, Ar preferably has those meanings which have already been mentioned in connection with the description of the cyclic imines of the formula (I) as being preferred. The nitroketones of the formula (XVIII) are novel.

Nitroketones of the formula (XVIII) can be prepared, for example, by condensing the ω-chloroalkyl phenyl ketone of the formula (XXI) in the presence of a diluent, such as, for example, methanol, ethanol, another lower aliphatic alcohol or else tetrahydrofuran, and in the presence of an acid binder, such as, for example, sodium hydride or an alkali metal alkoxide, preferably of the corresponding alcohol which is used as diluent, in accordance with the following equation:

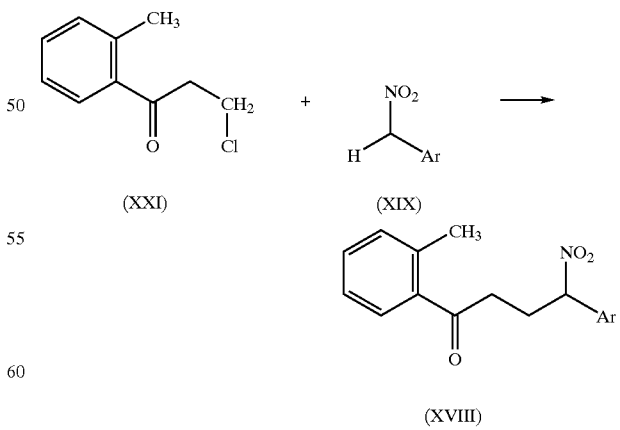

The ω-chloroalkyl phenyl ketone of the formula (XXI) can be prepared in a known manner, such as, for example, by Friedel-Crafts acylation of toluene with 3-chloropropionyl chloride.

The nitromethyl benzenes of the formula (XIX) are known or can be prepared in a known manner, such as, for example, by side-chain nitration of corresponding toluenes, or by reacting corresponding benzyl halides with silver nitrite [cf., for example, J. Am. Chem. Soc. 77, 6269 (1955); J. Am. Chem. Soc 86, 2681 (1964); Houben-Weyl, Methoden der Organischen Chemie, Georg Thieme Verlag Stuttgart, volume 10/1, 46–57 (halogen substitution), volume E16, 145–154 (both methods)]. The toluenes or benzyl halides required for this purpose are generally known compounds of organic chemistry.

The nitroketones of the formula (XVIII) can be prepared, for example, by Michael additions of nitromethylbenzenes of the formula (XIX) to phenyl vinyl ketone of the formula (XX) in the presence of a diluent, such as, for example, methanol, ethanol or another lower aliphatic alcohol, and in the presence of an acid binder, such as, for example, preferably an alkali metal alkoxide of the corresponding alcohol which is used as diluent, in accordance with the following equation (cf., for example, J. Prakt. Chem., Series 4, 1, 57 (1955); Houben-Weyl, Methoden der Organischen Chemie, Georg Thieme Verlag Stuttgan, volume 10/1, 199–206):

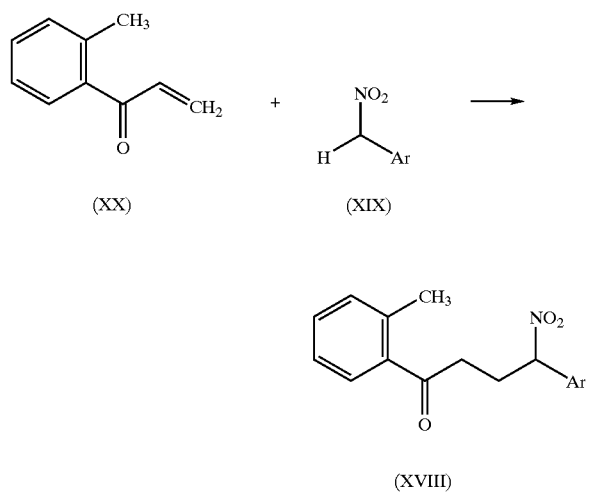

The phenyl vinyl ketone of the formula (XX) can be prepared, for example, by eliminating hydrogen chloride from P-chloropropiophenone of the formula (XXI), which can be obtained, for example, by Friedel-Crafts acylation of toluene (XXII) with 3-chloropropionyl chloride, said elimination being carried out in the presence of an acid binder, such as, for example, potassium acetate, and in the presence of a diluent, such as, for example, methanol, in accordance with the following equation [cf., for example, J. Prakt. Chem., Series 4, 1, 57 (1955)]:

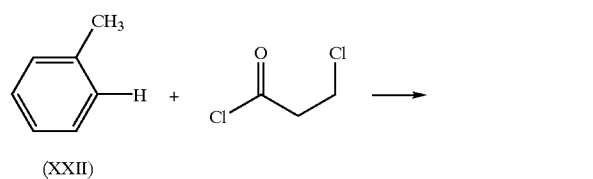

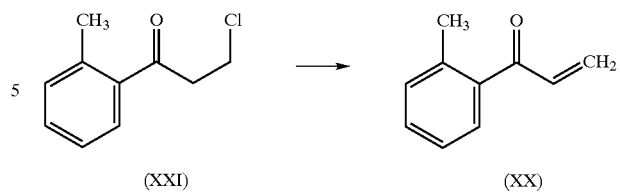

Toluene of the formula (XXII) is commercially available.

The phenyl vinyl ketone of the formula (XX) can also be prepared by reacting O-methyl methyl-2-methyl-benzohydroxamate of the formula (XXIII) with vinyl magnesium bromide, in accordance with the following equation:

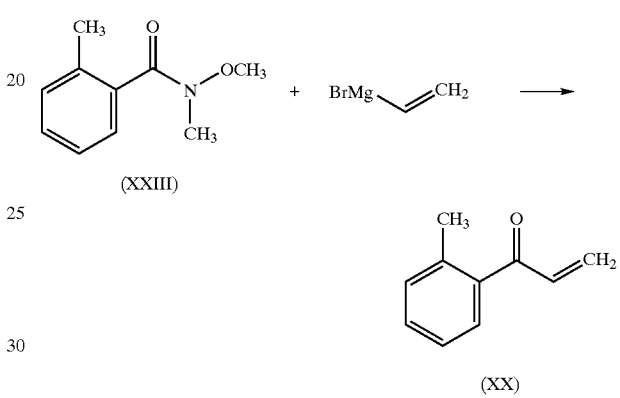

The O-methyl methyl-2-methyl-benzohydroxamate of the formula (XXIII) can be prepared by known methods, for example from the corresponding benzoic acid derivatives [cf., for example, Tetrahedron Lett. 22, 3815 (1981)].

Since the phenyl vinyl ketone of the formula (XX) is sensitive, it is, in a preferred variant for preparing the nitroketones of the formula (XVIII), directly reacted further with nitromethylbenzenes of the formula (XIX).

Nitroketones of the formula (XVIII) can also be prepared by adding, in accordance with the equation below, enamines of methyl phenyl ketones of the formula (XXVI) to α-nitrostyrenes of the formula (XXVII) and subjecting the reaction product to an acidic hydrolysis:

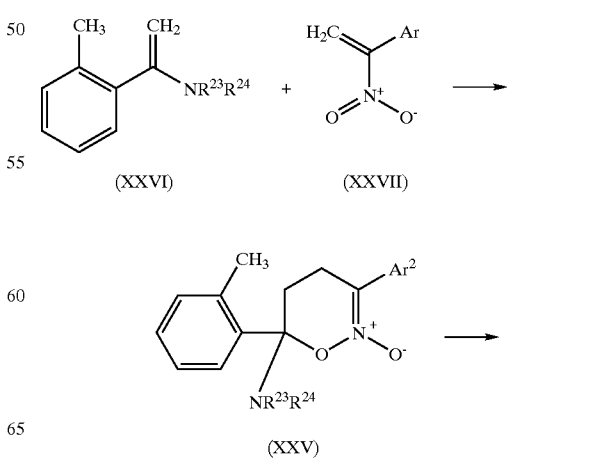

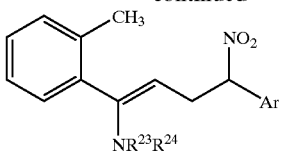

(XXIV)

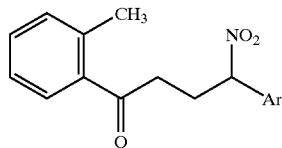

(XVIII)

In the formulae (XXIV), (XXV) and (XXVI), $R^{23}$ and $R^{24}$ together with the linking nitrogen atom represent a cyclic amino radical, such as, for example, 1-pyrrolidino, 1-piperidino or 4-morpholino.

In most cases, the addition proceeds in a [4+2]-cycloaddition to give isolatable 1,2-oxazine —N-oxide derivatives of the formula (XXV), and it is, if appropriate, carried out in the presence of a non-polar diluent, such as, for example, diethyl ether, at, for example, from −80° to +20° C. For the hydrolysis, use is made, for example, of aqueous mineral acids, such as hydrochloric acid, if appropriate in the presence of methanol or ethanol [cf. for example, Helv. Chim. Acta 68, 162 (1985); Tetrahedron 45, 2099 (1989)]. In many cases, it is advantageous to open the ring first to give compounds of the formula (XXIV), by simply dissolving the 1,2-oxazine -N-oxide derivative in methanol or ethanol, since otherwise the undesirable Nef reaction, which gives the corresponding diketo compound, occurs as a competing reaction [cf., for example, Tetrahedron 45, 2099 (1989)].

Some of the enamines of the formula (XXVI) are known, or they can be prepared, for example, from the correspondingly substituted acetophenones and the cyclic amines using standard methods (for example Org. Syntheses Vol. 58, 56, John Wiley & Sons, New York). Some of the acetophenones required for this purpose are commercially available or known, or they can be prepared by known methods of the chemistry of aromatics.

Some of the nitrostyrenes of the formula (XXVII) are known, or they can be prepared, for example, by formylation of the nitromethylbenzenes of the formula (XIX) given above (cf., for example, Houben-Weyl, Methoden der Organischen Chemie, Georg Thieme Verlag, Stuttgart, volume E16, 215).

The formula (XXVIII) provides a general definition of the imines required for carrying out the process A) c). In this formula, Ar preferably has those meanings which have already been mentioned in connection with the description of the cyclic imines of the formula (I) as being preferred.

The imines of the formula (XXVIII) can be prepared, for example, by carrying out Michael additions of N-diphenylmethylenebenzylamines of the formula (XXIX) to the phenyl vinyl ketone of the formula (XX), in accordance with the following equation:

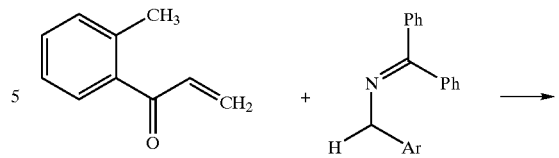

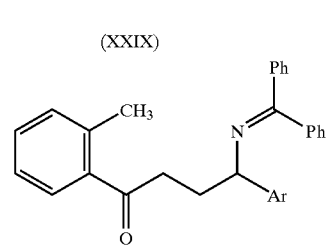

(XXVIII)

The addition is carried out in the presence of an acid binder and in the presence of a diluent, such as, for example, acetonitrile or dichloromethane, and, if appropriate, in the presence of a reaction auxiliary, for example at room temperature. A preferred acid binder is aqueous alkali, such as 50% strength aqueous sodium hydroxide solution in the presence of a phase-transfer catalyst, such as, for example, triethylbenzylammonium chloride as reaction auxiliary [cf., for example, Synth. Commun.17, 211 (1987)].

The preparation of the phenyl vinyl ketone of the formula (XX) is described above. The N-diphenylmethylene benzylamines of the formula (XXIX) are obtained, for example, by reacting the corresponding benzylamines with benzophenone (cf. for example, Tetrahedron. Lett. 1978, 2641). The benzylamines required for this purpose are known, or they can be prepared by known methods, such as, for example, aminolysis of the corresponding benzyl halides (see above).

The formula (m) provides a general definition of the cyclic O-methanesulphonyl oximes required for carrying out the process (B) according to the invention. In this formula, Ar preferably has those meanings which have already been mentioned in connection with the description of the cyclic imines of the formula (I) as being preferred. The O-methanesulphonyl oximes of the formula (III) are novel.

The O-methylsulphonyl oximes of the formula (II) can be prepared by, for example according to the equation below, initially converting cyclic α-aryl ketones of the formula (XXXI) by generally known methods into their oximes of the formula (XXX) and subsequently reacting these with methanesulphonyl chloride, similarly to the mesylation of alcohols:

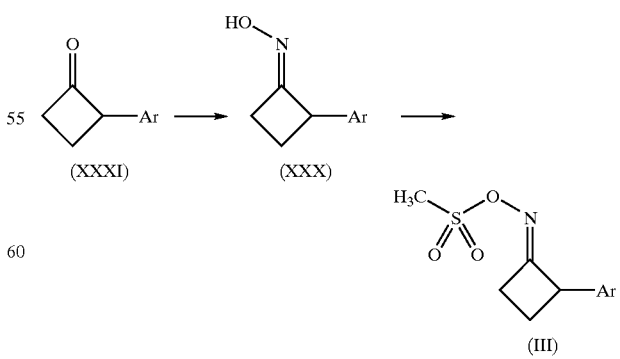

Cyclic α-aryl ketones of the formula (XXXI) can be prepared, for example, by epoxidizing 1-arylcycloalkenes of the formula (XXXEII) according to the equation below by customary methods, such as, for example, with m-chloroperbenzoic acid, to give oxirans of the formula (XXXII) and subsequently isomerizing these by acidic work-up [cf., for example, Tetrahedron 30, 2027 (1974)]:

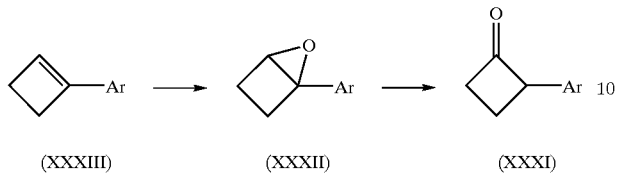

It is, of course, also possible to isomerize oxirans of the formula (XXXII) obtained by other routes to give cyclic α-aryl ketones of the formula (XXXI), for example by shaking a solution in chloroform with 20% strength sulphuric acid.

1-Arylcycloalkenes of the formula (XXXII) can be prepared, for example, by reacting according to the equation below the aryl Grignard compounds of the formula (XIV) described above with cyclobutanone of the formula (XXXV) under customary Grignard conditions and dehydrating the cyclic benzyl alcohols of the formula (XXXIV) which have been obtained, for example, in this manner:

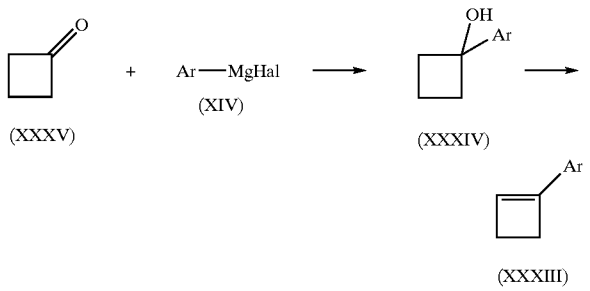

The dehydration can be carried out, for example, by dissolving the alcohol in a solvent of low polarity, such as hexane, and stirring with semi-concentrated sulphuric acid, for example at from 0° C. to 20° C. [cf., for example, Tetrahedron 30, 2027 (1974)].

Cyclobutanone of the formula (XXXV) is commercially available.

The formula (IV) provides a definition of the aryl Grignard compounds furthermore required for carrying out the process (B) according to the invention.

Aryl Grignard compounds of the formula (IV) can be prepared from o-tolyl halides and magnesium by the Grignard reaction. o-Tolyl halides are generally known compounds of organic chemistry.

The cyclic imines of the formula (V) required for carrying out the process (C) according to the invention are, if $X^1$ represents bromine or iodine, a subset of the compounds of the general formula (I) according to the invention, and they can be prepared, for example, by the processes (A) and (B). If $X^1$ represents trifluoromethanesulphonyl, the compounds of the formula (V-a) can be prepared by reacting hydroxyl compounds of the formula (I-f), which can also be prepared by the processes (A) and (B), with trifluoromethanesulphonyl chloride or trifluoro-methanesulphonic anhydride in the presence of an acid binder, such as, for example, pyridine, and, if appropriate, in the presence of a diluent, in accordance with the following equation:

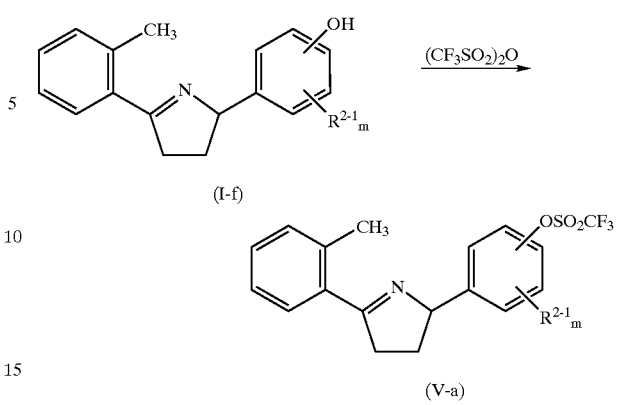

The formula (VI) provides a general definition of the boronic acids likewise required for carrying out the process (C) according to the invention. In this formula, $R^{1-1}$ preferably has those meanings which have already been mentioned in connection with the description of the cyclic imines of the formula (I-b) as being preferred.

Aromatic boronic acids of the formula (VI) are known or can be prepared by known methods [c.f. Chem. Rev. 45, 2457 (1995); Pure Appl. Chem. 66, 213 (1994)].

The cyclic imines of the formula (I-d) required for carrying out the process (D) according to the invention are a subset of the compounds of the general formula (I) according to the invention, and they can be prepared, for example, by processes (A) to (C).

The formula (VH) provides a definition of the compounds furthermore required for carrying out the process (D) according to the invention. In this formula, $R^9$, $R^{10}$, G, p, q and r each preferably have those meanings which have already been mentioned in connection with the description of the cyclic imines of the formula (I) as being preferred. Ab represents a customary leaving group, such as, for example, halogen, in particular chlorine or bromine; alkylsulphonyloxy, in particular methylsulphonyloxy; or optionally substituted arenesulphonyloxy, in particular phenylsulphonyloxy, p-chlorophenylsulphonyloxy or p-tolylsulphonyloxy.

The compounds of the formula (VII) are generally known compounds of organic chemistry.

Suitable acids for carrying out the process A) a) according to the invention are organic or inorganic Bronstedt acids, such as, for example, hydrogen fluoride, hydrogen chloride, sulphuric acid, phosphoric acid, formic acid, acetic acid, benzoic acid, citric acid, trifluoroacetic acid, methanesulphonic acid, trifluoromethane-sulphonic acid or toluenesulphonic acid.

Particularly suitable is the acidolysis with trifluoroacetic acid, which is usually employed for cleaving off the tert-butoxycarbonyl amino protecting group (c.f., for example, T. W. Greene, P. G. M. Wuts, Protective Groups in Organic Synthesis, 2nd Ed., John Wiley & Sons, New York 1991).

The process (A) a) according to the invention is, if appropriate, carried out in the presence of a suitable acid acceptor. Suitable acid acceptors are all customary inorganic or organic bases. These preferably include alkaline earth metal or alkali metal hydroxides, amides, alkoxides, acetates, carbonates or bicarbonates, such as, for example, sodium hydroxide, potassium hydroxide or ammonium hydroxide, sodium amide, lithium diisopropylamide, sodium methoxide, sodium ethoxide, potassium tert-butoxide, sodium acetate, potassium acetate, calcium acetate or ammonium acetate, sodium carbonate, potassium carbonate or ammonium carbonate, sodium bicarbonate or potassium bicarbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethyl-aminopyridine, diazabicyclooctane (DABCO), diazabicyclononene (DBN) or diazabicycloundecene (DBU).

The process (A) a) according to the invention is, if appropriate, carried out in the presence of a diluent. Suitable diluents are water, organic solvents and mixtures of these. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole, ketones, such as acetone, butanone, methyl isobutyl ketone or cyclohexanone; nitriles, such as acetonitrile, propionitrile, n- or i-butyronitrile or benzonitrile; amides, such as formamide, N,N-dimethylformamide, N,N-dimethyl-acetamide, N-methylformanilide, N-methylpyrrolidone or hexamethylphosphoric triamide; N-oxides, such as N-methylmorpholine N-oxide; esters, such as methyl acetate, ethyl acetate or butyl acetate; sulphoxides, such as dimethyl sulphoxide; sulphones, such as sulpholane, alcohols, such as methanol, ethanol, n- or i-propanol, N-, iso-, sec- or tert-butanol, ethanediol, propane-1,2-diol, ethoxyethanol, methoxyethanol, diethylene glycol monomethyl ether, diethylene glycol monoethyl ether.

When carrying out the process A) a), an excess of acid is generally employed.

The process A) b) according to the invention is carried out as a catalytic hydrogenation or using other generally known methods for reducing nitro groups (cf., for example, Houben-Weyl, Methoden der Organischen Chemie, Georg Thieme Verlag Stuttgart, volume 11/1, 394–409 and volume 4/1c, 490–506). The process A) c) according to the invention is carried out as a hydrolysis according to generally known methods, for example using aqueous hydrochloric acid.

Suitable diluents for carrying out the processes A) b) and A) c) are the diluents mentioned above for the process A) a).

Suitable diluents for carrying out the process (B) according to the invention are inert organic solvents and mixtures of these. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole.

Preference is given to using a solution of the Grignard compound of the formula (IV) in an ether and a solution of the O-methylsulphonyloxime of the formula (III) in a hydrocarbon.

The reaction temperature for the process (B) according to the invention can be varied within a relatively wide range. In general, the reaction is carried out at temperatures between −100° C. and +50° C., preferably between −80° C. and +30° C.

When carrying out the process (B) according to the invention, the Grignard compounds of the formula (IV) and the O-methylsulphonyl oxime of the formula (III) are employed in a molar ratio of from 1:1 to 3:1, preferably from 1:1 to 2:1.

Suitable catalysts for carrying out the process (C) according to the invention are palladium (0) complexes. Preference is given, for example, to tetrakis(triphenyl-phosphine) palladium.

Suitable acid acceptors for carrying out the process (C) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, caesium fluoride, and also tertiary amines, such as trimethylamine, triethylamine, tributylamine, N,N-di-methylaniline, N,N-dimethylbenzylamine, pyridine, N-methylpiperidine, N-methyl-morpholine, N,N-dimethylaminopyridine, diazabicyclooctane (DABCO), diazabi-cyclononene (DBN) or diazabicycloundecene (DBU).

Suitable diluents for carrying out the process (C) according to the invention are water, organic solvents and mixtures of these. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether.

The reaction temperature for the process (C) according to the invention can be varied within a relatively wide range. In general, the reaction is carried out at temperatures between 0° C. and +140° C., preferably between 50° C. and +100° C.

When carrying out the process (C) according to the invention, the boronic acids of the formula (VI) and the compounds of the formula (V) are employed in a molar ratio of from 1:1 to 3:1, preferably from 1:1 to 2:1. The catalyst is generally employed in amounts of from 0.005 to 0.5. mol, preferably 0.01 mol to 0.1 mol, per mole of the compound of the formula (V). In general, an excess of base is employed.

The process (D) according to the invention is preferably carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium hydroxide, potassium hydroxide or ammonium hydroxide, sodium amide, lithium diisopropylamide, sodium methoxide, sodium ethoxide, potassium tert-butoxide, sodium acetate, potassium acetate, calcium acetate or ammonium acetate, sodium carbonate, potassium carbonate or ammonium carbonate, sodium bicarbonate or potassium bicarbonate and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process (D) according to the invention can be carried out in the presence of a suitable phase-transfer catalyst. Examples of such catalysts include: tetrabutyl-ammonium iodide, tetrabutylammonium bromide or tetrabutylammonium chloride, tributylmethylphosphonium bromide, trimethyl-$C_{13}/C_{15}$-alkylammonium chloride or trimethyl-$C_{13}/C_{15}$-alkyl ammonium bromide, dibenzyldimethylammonium methyl sulphate, dimethyl-$C_{12}/C_{14}$-alkylbenzylammonium chloride, 15-crown-5, 18-crown-6 or tris-[2-(2-methoxyethoxy)-ethyl]-amine.

The process (D) according to the invention is preferably carried out in the presence of a diluent. Suitable diluents are, for example, all solvents listed for process (A).

The reaction temperature for the process (D) according to the invention can be varied within a relatively wide range. In general, the reaction is carried out at temperatures between −20° C. and +100° C., preferably between 0° C. and 60° C.

When carrying out the process (D) according to the invention, in general approximately equimolar amounts of the starting materials are employed. However, it is also possible to use an excess of the compound of the formula (VII).

The reactions in accordance with the process E) according to the invention are derivatization reactions known to the person skilled in the art, in particular of carboxylic esters and ketones (cf., for example, Houben-Weyl, Methoden der Organischen Chemie, Georg Thieme Verlag, Stuttgart, vol. VII/2b, in particular 1912 ff; vol. VIII about carboxylic esters and their derivatives; vol. E5, in particular p. 812 ff. and the literature quoted therein).

The reactions of the processes according to the invention can be carried out at atmospheric pressure or at elevated pressure; preference is given to working at atmospheric pressure. Work-up is carried out by customary methods of organic chemistry. The end products are preferably purified by crystallization, chromatographic purification or by removing the volatile components, if appropriate under reduced pressure.

The active compounds are suitable for controlling animal pests, in particular insects, arachnids and nematodes, encountered in agriculture, in forestry, in the protection of stored products and of materials, and in the hygiene field, and have good plant tolerance and low toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratornoides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., Dysdercus intermedius, *Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., Monomorium pharaonis and Vespa spp.

From the order of the Diptera, for example, Aedes spp., Anopheles spp., Culex spp., *Drosophila melanogaster,*

Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus*, Oscinella frit, Phorbia spp., *Pegomyla hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, Acarus siro, Argas spp., Ornithodoros spp., *Dermanyssus gallinae, Eriophyes ribis, Phyllocoptruta oleivora*, Boophilus spp., Rhipicephalus spp., Amblyomma spp., Ilyalomma spp., Ixodes spp., Psoroptes spp., Chorioptes spp., Sarcoptes spp., Tarsonemus spp., *Bryobia praetiosa*, Panonychus spp., Tetranychus spp.

The phytoparasitic nematodes include Pratylenchus spp., *Radopholus similis, Ditylenchus dipsaci, Tylenchulus semipenetrans*, Heterodera spp., Meloidogyne spp., Aplelenchoides spp., Longidorus spp., Xiphinema spp., Trichodorus spp.

The active compounds of the formula (I) according to the invention in particular have outstanding activity against mustard beetle larvae (*Phaedon cochleariae*), caterpillars of the owlet moth (*Spodoptera frugiperda*), larvae of the green rice leaf hopper (*Nephotettix cincticeps*), green peach aphids (*Myzus persicae*) and all stages of the common spider mite (*Tetranychus urticae*).

The active compounds can be converted to the customary formulations, such as solutions, emulsions, wettable powders, suspensions, powders, dusting agents, pastes, soluble powders, granules, suspension emulsion concentrates, natural and synthetic materials impregnated with active compound and very fine capsules in polymeric substances.

These formulations are produced in a known manner, for example preferably by mixing the active compounds with extenders, that is liquid solvents and/or solid carriers, if appropriate with the use of surface-active agents, that is emulsifying agents and/or dispersing agents and/or foam-forming agents.

If the extender used is water, it is also possible to employ, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysis products; suitable dispersing agents are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxy-phenyl)-acetamide; 8-hydroxyquinoline sulphate; methyl (E)-2-{2-[6-(2-cyano-phenoxy)-pyrimidin-4-yloxy]-phenyl}-3-methoxyacrylate; methyl (E)-methoximino-[alpha-(o-tolyloxy)-o-tolyl] acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cypro-conazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuramr, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as:

copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclofos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides

Bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides

Abamectin, AC 303 630, acephate, acrinathrin, alanycarb, aldicarb, alphamethrin, amitraz, avermectin, AZ 6054 1, azadirachtin, azinphos A, azinphos M, azocyclotin, Bacillus thuringiensis, bendiocarb, benfuracarb, bensultap, beta-cyluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlonnephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimfos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mevinphos, mesulfenphos, metaldehyde, methacrifos. methamidophos, methidathion, methiocarb, methomyl, metolcarb, milbemectin, monocrotophos, moxidectin, naled, NC 184, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlofos, pyridaphenthion, pyresmethrin, pyrethrum, pyridaben, pyrimidifen, pyriproxyfen, quinalphos, RH 5992, salithion, sebufos, silafluofen, sulfotep, sulprofos, tebufenozide, tebufenpyrad, tebupirimifos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth-regulators is also possible.

The active compound according to the invention can furthermore be present in its commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound has an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopyslla spp. and Ceratophyllus spp.

From the order of the Heteropterida, for example, Cimex spp., Triatoma spp., Rhodnius spp. and Panstrongylus spp. 5 From the order of the Blattarida, for example, *Blatta orientalis, Periplaneta americana, Blattela germanica* and Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Stemostoma spp. and Varroa spp.

From the order of the Actinedida (Prostigmata) and Acaridida (Astigmata), for example, Acarapis spp., Cheyletiella spp., Omithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they have an outstanding activity against all larval stages of the fly *Lucilia cuprina* and all development stages of the tick *Amblyomma variegattin*.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, caged birds, aquarium fish, and so-called experimental animals, such as, for example, hamsters, guinea-pigs, rats and mice. By controlling these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal administration, by dermal administration, for example in the form of dipping or bathing, spraying, pouring-on and spotting-on, washing, dusting, and awith the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials. The following insects may be mentioned by way of preferred examples but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*, Xyleborus spec., Tryptodendron spec., *Apate monachus, Bostrychus capucins, Heterobostrychus brunneus*, Sinoxylon spec. and *Dinoderus minutus*.

Dermapterans, such as *Sirex juvencus, Urocerus gigas, Urocerus gigas taignus* and *Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as *Lepisma saccharina.*

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.000 1 to 95% by weight, in particular 0.00 1 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-like solvents having an evaporation number of above 35 and a flashpoint of above 30° C., preferably above 45° C. Substances which are used as such oily and oil-like solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably monochloronaphthalene, are used.

The organic oily or oil-like solvents of low volatility and having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The artificial resin used as the binder can be employed in the form of an emulsion, dispersion or solution. Up to 10% by weight of bitumen or bituminous substances can also be used as binder. In addition, colorants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone. Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application.

Very particularly preferred components which may be admixed are insecticides, such as chlorpyrifos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention can be seen from the examples which follow.

PREPARATION EXAMPLES

Example I-9

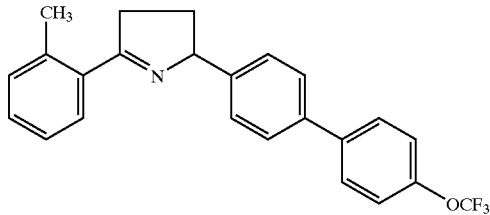

210 mg (0.4 mmol) of 1-tert-butyloxycarbonylamino-1-[4'-trifluoromethoxybiphenyl-4-yl]-3-[O-methylbenzoyl] propane were initially charged in 5 ml $CH_2Cl_2$, and the solution was cooled to 0° C. 1 ml of trifluoroacetic acid was subsequently added, and the mixture was stirred at room temperature for 4 h. The solvent was then removed under reduced pressure.

For work-up, the product mixture was repeatedly mixed with toluene which was subsequently removed under reduced pressure. The residue was finally taken up in ether, washed twice with water, dried and concentrated.

This gave 150 mg (93.1% of theory) of 2-[2-methylphenyl]-5-[4'-trifluoromethoxy-biphenyl-4-yl]-3,4-dihydro-2H-pyrrole as an oil.

$^1$H-NMR (400 MHz, $CDCl_3$, TMS): δ [ppm]=1.88 (m, 1H, CHNCH$\underline{H}$), 2.61 (m, 1H, CHNC$\underline{H}$H), 2.62 (s, 3H, C$\underline{H}_3$), 3.10 (m, 2H, CNC$\underline{H}_2$), 5.38 (t, 1H, CHN), 7.20–7.35 (5H, ArH), 7.46 (m, 2H, ArH), 7.53 (m, JH, ArH), 7.60 (m, 2H, ArH)

HPLC log P* (neutral)=6.05;

LC-MS: 396 M⊕ at 10.53 min.

* log P=negative logarithm to base 10 of the alkane/water partition coefficient, determined by HPLC analysis using water/acetonitrile as mobile phase on 125×4.0 mm Kromasil 120° C. 18 (5 μm); flow rate: 1.5 ml/min.

Example I-9 "One-pot variant"

0.964 g (3 mmol) of XI-a-2 was initially charged in 20 ml of THF and cooled to –78° C. At –78° C., 2.05 ml (3.3 mmol) of n-butyllithium (1.6 N solution in hexane) were then added dropwise, and the mixture was stirred at –78° C. for 30 min. At –78° C., 0.72 g (3.3 mmol) of di-tert-butyl dicarbonate in 6 ml of THF was then added dropwise. The mixture was stirred at –78° C. for a few minutes, then warmed to 0° C. and once more cooled to –78° C. 19.5 ml (3.9 mmol) of o-tolylmagnesium bromide (2.0 M in $Et_2O$) were then added dropwise at –78° C., and the mixture was warmed to 0° C. with stirring. At 0° C., 7.5 ml of trifluoroacetic acid were added, and the mixture was then stirred at room temperature for 4 h. The tetrahydrofuran was removed using a rotary evaporator and the residue was taken up in 25 ml of methylene chloride and admixed with 7.5 ml of trifluoroacetic acid.

The mixture was stirred at room temperature for another 6 h. All volatile components were subsequently removed using a rotary evaporator, and the residue was chromatographed over silica gel using ethyl acetate/cyclohexane 1:2.

Two fractions were isolated. The second fraction contained 434 mg of the desired product I-9.

The first fraction contained the trifluoroacetate of I-9 and was processed further:

The fraction was initially taken up in ethyl acetate and extracted with NaHCO$_3$ solution, then admixed with 100 ml of ethyl acetate and with 20% NaOH and stirred at room temperature overnight.

The solution was washed three times with saturated sodium chloride solution, dried, and the solvent was removed using a rotary evaporator. The residue was admixed three times with toluene which was in each case subsequently removed under reduced pressure.

After all volatile components had been removed under reduced pressure, the mixture was once more chromatographed over silica gel using ethyl acetate/cyclohexane 1:3.

Two fractions were isolated; the first contained another 36 mg of I-9 and the second contained 61 mg of the trifluoroacetate.

This gave a total yield of 470 (434+36) mg (46% of theory) of I-9.

(Physical data see "stepwise variant")

Example I-43

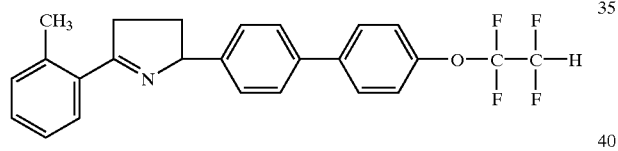

1 g of the compound (VIII-43) was initially charged in 10 ml of CH$_2$Cl$_2$ and cooled to 0° C. 1.39 ml of trifluoroacetic acid were added, and the mixture was subsequently stirred at room temperature overnight. The trifluoroacetic acid was removed under reduced pressure using a rotary evaporator, and the residue was taken up in ethyl acetate. The pH was adjusted to 11 using 1 N NaOH. The organic phase was washed with water, dried over MgSO$_4$, filtered and concentrated.

This gave 0.23 g of a solid.
M.p.: 87° C.;
HPLC: log P (pH 2.3)=3.02.

Preparation of the Starting Materials

γ-ethoxy-γ-butyrolactam

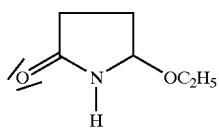

At 0° C., 9.91 g of succinimide were initially charged in 415 ml of ethanol and admixed, a little at a time, with a total of 5.53 g of sodium borohydride. At this temperature, every 15 minutes 2 to 3 drops of 2N ethanolic hydrogen chloride were added dropwise over a period of 4½ hours. The mixture was subsequently acidified to pH 3 using more acid. The mixture was stirred at 0° C. for one hour and then neutralized with 1% strength ethanolic potassium hydroxide solution, stirred for a further 15 minutes and concentrated. The residue was taken up in water and extracted three times with dichloromethane. Drying over sodium sulphate and concentration gave 7.16 g (55% of theory) of γ-ethoxy-γ-butyrolactam.

Example XI-1

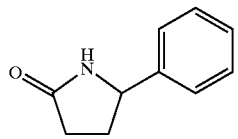

At 0° C., 6.45 g of γ-ethoxy-γ-butyrolactam and 50 ml of conc. sulphuric acid were initially charged, and 18.8 ml of benzene were added. After thawing, the mixture was stirred at room temperature for 4 days. For work-up, the mixture was poured onto ice and extracted three times with ethyl acetate, the combined extracts were washed once each with water and saturated sodium chloride solution, dried and concentrated. This gave 8.1 g (100% of theory) of γ-phenyl-γ-butyrolactam.

$^1$H-NMR (400 MHz, d$_6$-DMSO) δ [ppm]: 1.75 (m, $^1$H): 2.23 (t, 2H); 2.45 (m, $^1$H); 4.67 (t, $^1$H); 7.26–7.39 (m, 5H); 8.08 (brd, $^1$H).

Example XI-2

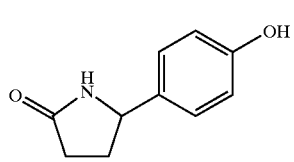 (XI-2a)

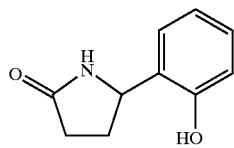 (XI-2b)

At 0° C., 12.9 g of γ-ethoxy-γ-butyrolactam, 10 ml of conc. sulphuric acid and 90 ml of glacial acetic acid were initially charged and admixed, a little at a time, with a total of 18.8 g of phenol. After thawing, the mixture was stirred at room temperature for 2 days. For work-up, the mixture was poured onto ice and extracted three times with ethyl acetate, and the combined extracts were washed once each with water and saturated sodium chloride solution, dried and concentrated. After some time, γ-2-hydroxyphenyl-γ-butyrolactam (XI-2b) of melting point 220° C. (6.4 g, 36% of theory) crystallized from the aqueous phase. The residue obtained after concentration was stirred with a 1:1 mixture of cyclohexane/ethyl acetate and gave, after filtration with suction, 4.65 g of γ-4-hydroxyphenyl-γ-butyrolactam (XI-2a) of melting point 183° C. The filtrate was concentrated. A further 3.35 g (total: 45% of theory) of γ-4-hydroxyphenyl-γ-butyrolactam were obtained by recrystallization from dichloromethane/hexane.

Example XVII-2

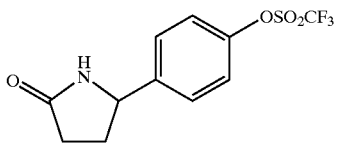

At 0° C., 10 g of trifluoromethanesulphonic anhydride were added dropwise to 5.23 g of γ-4-hydroxyphenyl-γ-butyrolactam (for example from Ex. XI-2) in 60 ml of pyridine. The mixture was stirred at room temperature overnight, then poured onto ice, acidified with 10% strength hydrochloric acid and extracted three times with ethyl acetate. Drying and evaporation of the solvent gave 6.4 g (70% of theory) of γ-4-trifluoromethylsulphonyloxyphenyl-γ-butyrolactam of melting point 127° C.

Example XI-a-2

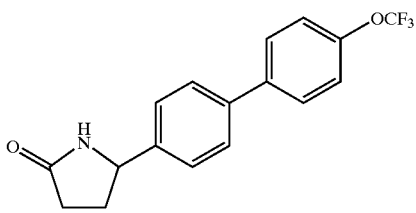

Under argon, 5.4 g of γ-4-trifluoromethylsulphonyloxyphenyl-γ-butyrolactam (for example from Ex. XVII-2) were initially charged in 43 ml of dimethoxyethane. 5.87 g of 4-trifluoromethoxyboronic acid and 1.01 g of tetrakis (triphenylphosphine)-palladium were added successively. After 15 minutes, 28 ml of a 2M solution of sodium carbonate were added and the mixture was heated to 80° C. and stirred overnight. After the reaction had ended, the mixture was taken up in water/ethyl acetate, the phases were separated and the aqueous phase was extracted twice with ethyl acetate. The combined organic phases were washed with saturated sodium chloride solution and dried. Concentration gave 5.5 g (98% of theory) of γ-4'-trifluoromethoxybiphenyl-4-yl-γ-butyrolactam of melting point 128° C.

Example XI-3

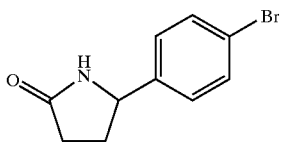

In a 3l three-necked flask fitted with stirrer and distillation bridge, 199.3 g of ammonium formate were initially charged in 127.9g.of formic acid, and 210g of 4-bromobenzoylpropionic acid which had been recrystallized from toluene were added. The flask was then immersed in an oil bath which was at 200° C. At 60° C., the content of the flask starts to dissolve with evolution of gas. Over a period of approximately 2 h, the mixture is distilled, at a bottom temperature which increases from 140 to 167° C. After cooling to below 60° C., 1 l of dichloromethane was added carefully, and salt which had precipitated out was separated off by filtration with suction using a nutsch filter. The organic phase was washed with 1 l of water, dried over magnesium sulphate and concentrated under reduced pressure. For purification, the crude product was filtered through 1 kg of silica gel using dichloromethane/ethanol/triethylamine (95:5:3) and subsequently crystallized from methyl tert-butyl ether. This gave 38 g (19% of theory) of γ-4-bromophenyl-γ-butyrolactam of melting point 142° C.

Example XI-43

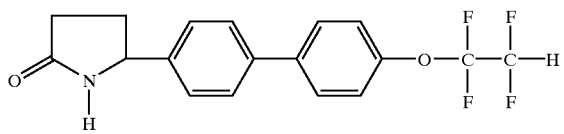

400 ml of HF were condensed into an autoclave. 38.7 g of γ-ethoxy-γ-butyrolactam and 40.6 g of tetrafluoroethoxybiphenyl were then jointly dissolved in 100 ml of $CH_2Cl_2$, and the mixture was added to the autoclave. The reaction mixture was stirred at room temperature overnight. The HF was drawn off and the residue was taken up in $CH_2Cl_2$ and washed with aqueous sodium bicarbonate solution. The organic phase was dried over $MgSO_4$, filtered and concentrated. The crude product was recrystallized from 500 ml of toluene. This gave 20.9 g of a white solid.

HPLC: log P (pH 2–3)=2.79;

Example IX-1

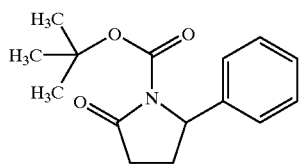

3.4 g of γ-phenyl-γ-butyrolactam (for example from Ex. XI-1) were initially charged in 63 ml of tetrahydrofuran (THF) and, at −78° C., admixed with 9.24 ml of a 2.4N solution of butyllithium in n-hexane. The mixture was stirred at this temperature for half an hour, a solution of 5.04 g of di-tert-butyl dicarbonate in 20 ml of THF was added dropwise with further cooling and the mixture was stirred at −78° C. for a further three hours and then without cooling overnight. The mixture was then hydrolysed using saturated aqueous ammonium chloride solution, diluted with water and extracted three times with ethyl acetate. The combined organic phases were washed with saturated sodium chloride solution and dried over magnesium sulphate. Concentration gave 1.54 g (28% of theory) of N-t-butoxycarbonyl-γ-phenyl-γ-butyrolactam.

$^1$H-NMR (400 MHz, $d_6$-DMSO) δ [ppm]: 1.18 (s, 9H), 1.73 (m, 1H); 2.40–2.60 (m, 3H); 5.10 (m, 1H), 7.24 (m, 2H); 7.30 (m, 1H); 7.38 (m, 2H).

Example IX-2

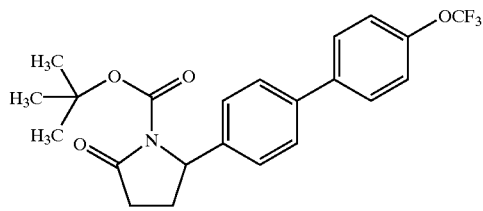

1.7 g of γ-4'-trifluoromethoxybiphenyl-4-yl-γ-butyrolactam (for example from Ex. XI-a-2) were initially charged in 30 ml of tetrahydrofuran (THF) and, at −78° C., admixed with 2.42 ml of a 2.4N solution of butyllithium in n-hexane. The mixture was stirred at this temperature for half an hour, and a solution of 1.27 g of di-tert-butyl dicarbonate in 10 ml of THF was then added dropwise with further cooling. The cooling was then removed and the mixture was stirred at room temperature overnight. The mixture was then hydrolysed using saturated aqueous ammonium chloride solution, acidified with 2N hydrochloric acid and extracted three times with dichloromethane. The extract was dried and concentrated and the product was purified by column chromatography (stationary phase: silica gel; mobile phase: gradient cyclohexane:ethyl acetate=5:1.3 to 1.1:1). This gave 1.14 g (47% of theory) of partially crystalline N-t-butoxycarbonyl-γ-4'-trifluoromethoxybiphenyl-4-yl-γ-butyrolactam.

$^1$H-NMR (400 MHz, CDCl$_3$) δ [ppm]: 1.22 (s, 9H); 1.79 (m, 1H); 2.48–2.60 (m, 3H); 5.17 (m, 1H); 7.36 (d, 2H); 7.46 (d, 2H); 7.71 (d, 2H); 7.80 (d, 2H).

Example IX-3

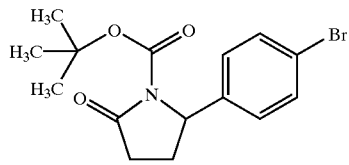

At −78° C., 3.24 ml of diisopropylamine were initially charged in 90 ml of THF and admixed with 9.24 ml of a 2.4 N solution of butyllithium in n-hexane. The mixture was stirred at this temperature for ½ h, and a solution of 5.02 g of γ-4-bromophenyl-γ-butyrolactam (for example from Example XI-3) in 20 ml of THF was then added dropwise. The mixture was stirred at −78° C. for a further ½ h, and 5.04 g of di-tert-butyl dicarbonate in 20 ml of THF were then added dropwise, and the mixture was allowed to thaw and stirred at room temperature overnight. The mixture was then hydrolysed using saturated aqueous ammonium chloride solution, acidified with 2N hydrochloric acid and extracted three times with 150 ml of dichloromethane. The extract was dried over magnesium sulphate and concentrated, and the product was then purified by crystallization from dichloromethane/hexane. This gave a total of 7.61 g (97% of theory) of crystalline N-t-butoxycarbonyl-γ-4-bromophenyl-γ-butyrolactam. The crystal fraction of the highest purity (2.34 g) melted at 122–124° C.

Example IX-43

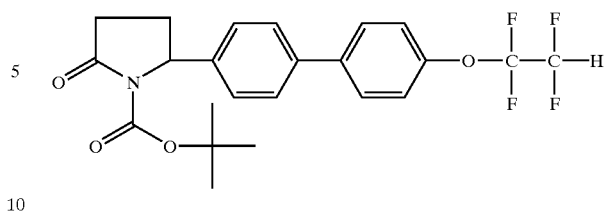

8.8 g of the compound (XI-43) were heated with 8.1 g of tert-butyl pyrocarbonate and 0.2 g of potassium fluoride in 80 ml of toluene at 108° C. for 6 hours, and the mixture was subsequently allowed to stand at room temperature overnight. 6.3 g of a solid precipitate (the solid precipitate also corresponds to the desired product) were filtered off with suction. The toluene solution was washed with water, and the organic phase was dried over MgSO$_4$, filtered and concentrated using a rotary evaporator. This gave 6.1 g of a white solid.

M.p. 134° C.; log P (pH 2.3)=3.96;

Example VIII-2

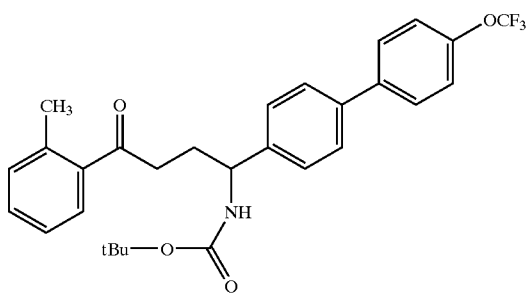

420 mg (1 mmol) of N-tert-butoxycarbonyl-γ-4'-trifluoromethoxybiphenyl-4-yl-γ-butyrolactam (from Example IX-2) were initially charged in 25 ml of THF and cooled to −78° C.

At −78° C., 6.5 ml (13 mmol) of o-tolylmagnesium bromide (2 M in Et$_2$O) were subsequently added dropwise with stirring.

The reaction mixture was then hydrolysed using saturated ammonium chloride solution and extracted with ethyl acetate. The organic phases were combined, dried and concentrated.

The crude product was finally chromatographed over silica gel using ethyl acetate/cyclohexane 1:5.

This gave 0.228 g (44.9% of theory) of 1-tert-butyloxycarbonylamino-1-[4'-trifluoro-methoxybiphenyl-4-yl]-3-[o-methylbenzoyl]propane as an oil.

$^1$H-NMR (400 MHz, CDCl$_3$, TMS): δ [ppm]=1.19 (s, 9H, [CH$_3$]$_3$), 1.79, 2.12, 2.22 2.53 (m, 1H, CH̲H), 2.58 (s, 3H, CH̲$_3$), 5.11 (d, 1H, CHN), 5.49 (s, 1H, NH), 7.15–7.65 (12H, ArH).

Example VIII-43

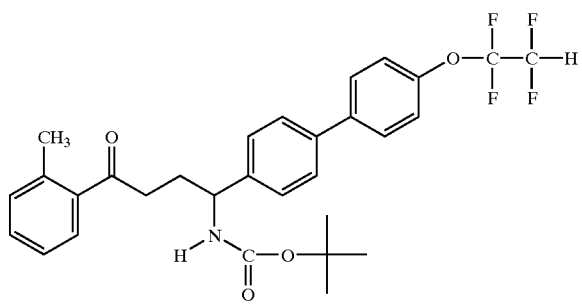

was prepared by the method of Example VIII-2.
log P (pH 2.3)=5.05;
M.p. 134–135° C.

Biological Examples

Example A

Heliothis armigera test

| Solvent: | 7 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emusifier-containing water to the desired concentration.

Soybean shoots (*Glycine max*) are treated by being dipped into the preparation of active compound of the desired concentration and are populated with caterpillars of the cotton bollworm (*Heliothis armigera*) while the leaves are still moist.

After the desired period of time, the kill in % is determined. 100% means that all caterpillars have been killed; 0% means that none of the caterpillars have been killed.

In this test, for example, the compound of Preparation Example I-9 shows, at an exemplary concentration of active compound of 0.004%, a kill of 100% after 6 days.

Example B

Phaedon larvae test

| Solvent: | 7 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emusifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the compound of Preparation Example I-9 shows, at an exemplary concentration of active compound of 0.004%, a kill of 100% after 6 days and the compound of Preparation Example I-43 shows here, at an exemplary concentration of active compound of 0.01%, a kill of 100% after 7 days.

Example C

Plutella test

| Solvent: | 7 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emusifier-containing water to the desired concentration.

Cabbage leaves (*Brassica oleracea*) are treated by being dipped into the preparation of active compound of the desired concentration and are populated with caterpillars of the diamond-back moth (*Plutella xylostella*) while the leaves are still moist.

After the desired period of time, the kill in % is determined. 100% means that all caterpillars have been killed; 0% means that none of the caterpillars have been killed.

In this test, for example, the compound of Preparation Example I-9 shows, at an exemplary concentration of active compound of 0.004%, a kill of 100% after 6 days.

Example D

Spodoptera frugiperda test

| Solvent: | 7 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emusifier-containing water to the desired concentration.

Cabbage leaves (*Brassica oleracea*) are treated by being dipped into the preparation of active compound of the desired concentration and are populated with caterpillars of the army-worm (*Spodoptera frugiperda*) while the leaves are still moist.

After the desired period of time, the kill in % is determined. 100% means that all caterpillars have been killed; 0% means that none of the caterpillars have been killed.

In this test, for example, the compound of Preparation Example I-9 shows, at an exemplary concentration of active compound of 0.004%, a kill of 100% after 6 days and the compound of Preparation Example I-43 shows here, at an exemplary concentration of active compound of 0.01%, a kill of 100% after 7 days.

Example E

Tetranychus test (OP-resistant/dip treatment)

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of the active compound of the desired concentration.

After the desired period of time, the action in % is determined. 100% means that all spider mites have been killed; 0% means that none of the spider mites have been killed.

In this test, for example, the compound of Preparation Example I-9 shows, at a concentration of active compound of 0.004%, a kill of 98% after 7 days and the compound of Preparation Example I-43 shows here, at an exemplary concentration of active compound of 0.01%, a kill of 100% after 7 days.

What is claimed is:

1. Compounds of the formula (I)

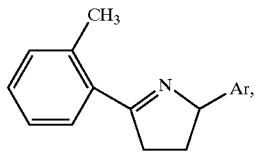

(I)

in which
Ar represents the radical

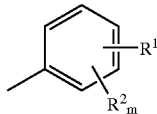

in which
  m represents 0, 1, 2, 3 or 4,
  $R^1$ represents hydrogen, F, Cl, Br, cyano, trialkylsilyl, —CO—$NR^4R^5$, tetrahydropyranyl or represents one of the following groupings
    (l) —X—A
    (m) —B—Z—D or
    (n) —Y—E,
  $R^2$ represents hydrogen, halogen, cyano, nitro, alkyl, alkoxy, halogenoalkyl, halogenoalkoxy, alkoxyalkoxy or —$S(O)_OR^3$,
  with the proviso that $R^1$ does not represent hydrogen if m=1 and $R^2$=iodine,
  o represents 0, 1 or 2,
  $R^3$ represents alkyl or halogenoalkyl,
  $R^4$ and $R^5$ independently of one another each represent hydrogen, alkyl, halogenoalkyl or represent phenyl or phenylalkyl, each of which is unsubstituted or mono- or polysubstituted by radicals from the list $W^1$,
  X represents a direct bond, oxygen, sulphur, carbonyl, carbonyloxy, oxycarbonyl, alkylene, alkenylene, alkinylene, alkyleneoxy, oxyalkylene, thioalkylene, alkylenedioxy or dialkylsilylene,
  A represents phenyl, naphthyl or tetrahydronaphthyl, each of which is unsubstituted or mono- or polysubstituted by radicals from the list $W^1$, or represents 5- to 10-membered heterocyclyl containing one or two aromatic rings and having one or more heteroatoms from the group consisting of nitrogen, oxygen and sulphur and being in each case unsubstituted or mono- or polysubstituted by radicals from the list $W^2$,
  B represents p-phenylene which is unsubstituted or mono- or disubstituted by radicals from the list $W^1$,
  Z represents oxygen or sulphur,
  D represents hydrogen, alkyl, alkenyl, alkinyl, halogenoalkyl, halogeno-alkenyl, represents in each case unsubstituted or halogen-, alkyl-, alkenyl-, halogenoalkenyl, phenyl-, styryl-, halogenophenyl- or halogenostyryl-substituted cycloalkyl or cycloalkylalkyl; represents in each case unsubstituted or halogen- or alkyl-substituted cycloalkenyl or cycloalkenyl-alkyl; represents in each case unsubstituted or nitro-, halogen-, alkyl-, alkoxy-, halogenoalkyl- or halogenoalkoxy-substituted phenylalkyl, naphthylalkyl, tetrahydronaphthylalkyl or hetarylalkyl having 5 or 6 ring members and one or two heteroatoms from the group consisting of nitrogen, oxygen and sulphur; represents —CO—$R^6$, —CO—$NR^7R^8$ or represents the grouping
    —$(CH_2)_p$—$(CR^9R^{10})_q$—$(CH_2)_rG$
  or
  Z and D together represent unsubstituted or nitro-, halogen-, alkyl-, alkoxy-, halo-genoalkyl- or halogenoalkoxy-substituted phenoxyalkyl,
  Y represents a direct bond, oxygen, sulphur, carbonyl, carbonyloxy, oxycarbonyl, alkylene, alkenylene, alkinylene, alkyleneoxy, oxyalkylene, thioalkylene, alkylenedioxy or represents p-phenylene which is unsubstituted or mono- or disubstituted by radicals from the list $W^1$,
  E represents hydrogen, alkyl, alkenyl, alkinyl, halogenoalkyl, halogeno-alkenyl, represents in each case unsubstituted or halogen-, alkyl-, alkenyl-, halogenoalkenyl-, phenyl-, styryl-, halogenophenyl- or halogeno-styryl-substituted cycloalkyl; represents in each case unsubstituted or halogen- or alkyl-substituted cycloalkenyl; represents phenyl which is unsubstituted or mono- to tetrasubstituted by radicals from the list $W^1$ or represents 5- or 6-membered hetaryl having one or two heteroatoms from the group consisting of nitrogen, oxygen and sulphur and being in each case unsubstituted or mono- to tetrasubstituted by radicals from the list $W^2$; or represents the grouping
    —$(CH_2)_p$—$(CR^9R^{10})_q$—$(CH_2)_rG$
  $R^6$ represents alkyl, alkoxy, alkenyl, alkenyloxy, in each case optionally halogen-, alkyl-, alkenyl-, halogenoalkyl- or halogenoalkenyl-substituted cycloalkyl, cycloalkyloxy or cycloalkylalkyloxy or represents in each case optionally nitro-, halogen-, alkyl-, alkoxy-, halogenoalkyl- or halogenoalkoxy-substituted phenyl or naphthyl,
  $R^7$ represents hydrogen or alkyl,
  $R^8$ represents alkyl, halogenoalkyl; represents in each case unsubstituted or halogen-, alkyl-, alkenyl-, halogenoalkyl- or halogenoalkenyl-substituted cycloalkyl or cycloalkylalkyl; or represents in each case unsubstituted or halogen-, alkyl-, alkoxy-, halogenoalkyl- or halogenoalkoxy-substituted phenyl or phenylalkyl, p, q and r independently of one another each represent 0, 1, 2 or 3, their sum being smaller than 6 and greater than 1, $R^9$ and $R^{10}$ independently of one another each represent hydrogen or alkyl, G represents cyano, represents an unsubstituted or halogen-, alkyl- or halogenoalkyl- and, at the point of linkage, optionally $R^{11}$-substituted 5- or 6-membered heterocycle having 1 to 3 identical or different heteroatoms from the group consisting of nitrogen, oxygen and sulphur or one of the following groups (a) —CO—$RL^{11}$
(b) —CO—$OR^{12}$
(c) —CO—$NR^{13}R^{14}$
(d) —CS—$NR^{13}R^{14}$ (e)
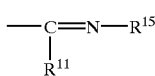

(f)
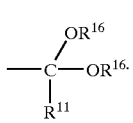

(g)
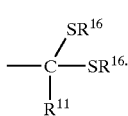

(h)
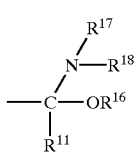

(i)
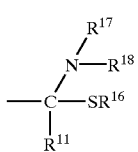

(j)
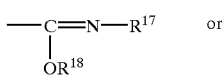 or (k)
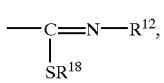

$R^{11}$ represents hydrogen, alkyl, alkenyl, halogenoalkyl, halogenoalkenyl, represents unsubstituted or halogen-, alkyl- or halogenoalkyl-substituted cycloalkyl; or represents phenyl which is unsubstituted or mono- to pentasubstituted by alkylcarbonylamino, alkylcarbonylalkylamino and/or radicals from the list $W^3$, $R^{12}$ represents hydrogen, alkyl, alkenyl, halogenoalkyl, halogenoalkenyl; represents in each case unsubstituted or halogen-, alkyl- or halogeno-alkyl-substituted cycloalkyl or cycloalkylalkyl or represents arylalkyl which is unsubstituted or mono- to pentasubstituted by radicals from the list $W^3$, $R^{13}$ and $R^{14}$ independently of one another each represent hydrogen, alkyl, alkenyl, halogenoalkyl, halogenoalkenyl, alkoxy, represent in each case unsubstituted or halogen-, alkyl- or halogenoalkyl-substituted cycloalkyl or cycloalkylalkyl, represent aryl or arylalkyl, each of which is unsubstituted or mono- to pentasubstituted by radicals from the list $W^3$, represent —$OR^{12}$ or —$NR^{11}R^{12}$ or together represent an alkylene chain having 2 to 6 members in which optionally one methylene group is replaced by oxygen, $R^{15}$ represents —$OR^12$, —$NR^{11}R^{12}$ or —$N(R^{11})$—$COOR^{12}$, $R^{16}$, $R^{17}$ and $R^{18}$ independently of one another each represent alkyl, $W^1$ represents hydrogen, halogen, cyano, formyl, nitro, alkyl, trialkylsilyl, alkoxy, halogenoalkyl, halogenoalkoxy, halogenoalkenyloxy, alkyl carbonyl, alkoxycarbonyl, pentafluorothio or —$S(O)_OR^3$, $W^2$ represents halogen, cyano, formyl, nitro, alkyl, trialkylsilyl, alkoxy, halogenoalkyl, halogenoalkoxy, alkylcarbonyl, alkoxycarbonyl, penta-fluorothio, —$S(O)_OR^3$ or —$C(R^{11})=N-R^{15}$, $W^3$ represents halogen, cyano, nitro, alkyl, alkoxy, halogenoalkyl, halogeno-alkoxy, dialkylamino, —$S(O)_O R^3$, —$COOR^{19}$ or —$CONR^{20}R^{21}$, $R^{19}$ represents hydrogen, alkyl, halogenoalkyl, represents unsubstituted or halogen-, alkyl or halogenoalkyl-substituted cycloalkyl; or represents phenyl which is unsubstituted or mono- to pentasubstituted by radicals from the list $W^4$, $R^{20}$ and $R^{21}$ independently of one another each represent hydrogen, alkyl, alkenyl, halogenoalkyl, halogenoalkenyl, alkoxy, represent in each case unsubstituted or halogen-, alkyl- or halogenoalkyl-substituted cycloalkyl or cycloalkylalkyl; or represent aryl or arylalkyl, each of which is unsubstituted or mono- to pentasubstituted by radicals from the list $W^4$, represent —$OR^{16}$ or —$NR^{17}R^{18}$ or together represent an alkylene chain having 2 to 6 members in which optionally one methylene group is replaced by oxygen, and $W^4$ represents halogen, cyano, nitro, alkyl, alkoxy, halogenoalkyl, haiogeno-alkoxy, dialkylamino, alkoxycarbonyl, dialkylaminocarbonyl or —$S(O)_OR^3$.

2. Compounds of the formula (I) according to claim 1, in which

Ar represents the radical

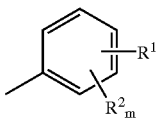

where m represents 0, 1, 2 or 3, $R^1$ represents a substituent in the meta or para position from the group consisting of hydrogen, F, Cl, Br, cyano, tri-($C_1$–$C_6$-alkyl)-silyl, —CO—$NR^4R^5$, tetrahydropyranyl or one of the following groupings (l) —X—A (m) —B—Z—D or (n) —Y—E, $R^2$ represents hydrogen, halogen, cyano, nitro, $C_1$–$C_{16}$-alkyl, $C_1$–$C_{16}$-alkoxy, $C_1$–$C_6$-halogenoalkyl, $C_1$–$C_6$-halogenoalkoxy, $C_1$–$C_8$-alkoxy-$C_1$–$C_8$-alkoxy or —S(O)$_o$R$^3$, with the proviso that $R^1$ does not represent hydrogen if m=1 and $R^2$=iodine, o represents 0, 1 or 2, $R^3$ represents $C_1$–$C_6$-alkyl or represents fluorine- or chlorine-substituted $C_1$–$C_6$-alkyl, $R^4$ and $R^5$ independently of one another each represent hydrogen, $C_1$–$C_6$-alkyl, $C_1$–$C_6$-halogenoalkyl; or represent phenyl or phenyl-$C_1$–$C_4$-alkyl, each of which is unsubstituted or mono- to trisubstituted by radicals from the list $W^1$, X represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylene-dioxy or di-$C_1$–$C_4$-alkylsilylene, A represents phenyl, naphthyl or tetrahydronaphthyl, each of which is unsubstituted or mono- to tetrasubstituted by radicals from the list $W^1$, or represents 5- to 10-membered heterocyclyl containing 1 or 2 aromatic rings and having 1 to 4 heteroatoms, which contains 0 to 4 nitrogen atoms, 0 to 2 oxygen atoms and 0 to 2 sulphur atoms, and is in each case unsubstituted or mono- to tetrasubstituted by radicals from the list $W^2$, B represents p-phenylene which is unsubstituted or mono- or disubstituted by radicals from the list $W^1$, Z represents oxygen or sulphur, D represents hydrogen, $C_1$–$C_{16}$-alkyl, $C_2$–$C_{16}$-alkenyl, $C_2$–$C_6$-alkinyl, $C_1$–$C_{16}$-halogenoalkyl, $C_2$–$C_{16}$-halogenoalkenyl, represents in each case unsubstituted or halogen-, $C_1$–$C_4$-alkyl-, $C_2$–$C_4$-alkenyl-, $C_2$–$C_4$-halogenoalkenyl-, phenyl-, styryl-, halogenophenyl- or halogenostyryl-substituted $C_3$–$C_8$-cycloalkyl or $C_3$–$C_8$-cycloalkyl-$C_1$–$C_6$-alkyl, represents in each case unsubstituted or halogen- or $C_1$–$C_4$-alkyl-substituted $C_5$–$C_8$-cycloalkenyl or $C_5$–$C_8$-cycloalkenyl-$C_1$–$C_4$-alkyl, represents in each case unsubstituted or nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, naphthyl-$C_1$–$C_6$-alkyl, tetrahydronaphthyl-$C_1$–$C_6$-alkyl or hetaryl-$C_1$–$C_6$-alkyl having 5 or 6 ring members and 1 or 2 heteroatoms from the group consisting of nitrogen, oxygen and sulphur; represents —CO—R$^6$, —CO—NR$^7$R$^8$ or represents the grouping —(CH$_2$)$_p$—(CR$^9$R$^{10}$)$_q$—(CH$_2$)$_r$G, Z and D together may also represent in each case unsubstituted or nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenoxy-$C_1$–$C_4$-alkyl, Y represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylene-dioxy or represents p-phenylene which is unsubstituted or mono- or disubstituted by radicals from the list $W^1$, E represents hydrogen, $C_1$–$C_{16}$-alkyl, $C_2$–$C_{16}$-alkenyl, $C_2$–$C_6$-alkinyl, $C_1$–$C_{16}$-halogenoalkyl, $C_2$–$C_{16}$-halogenoalkenyl, represents unsubstituted or halogen-, $C_1$–$C_4$-alkyl-, $C_2$–$C_4$-alkenyl-, $C_2$–$C_4$-halogenoalkenyl-, phenyl-, styryl-, halogenophenyl- or halogenostyryl-substituted $C_3$–$C_8$-cycloalkyl, represents unsubstituted or halogen- or $C_1$–$C_4$-alkyl-substituted $C_5$–$C_8$-cycloalkenyl, represents phenyl which is unsubstituted or mono- to tetrasubstituted by radicals from the list $W^1$ or represents 5- or 6-membered hetaryl having 1 or 2 heteroatoms from the group consisting of nitrogen, oxygen and sulphur, which is in each case unsubstituted or mono- to tetrasubstituted by radicals from the list $W^2$ or represents the grouping —(CH$_2$)$_p$—(CR$^9$R$^{10}$)$_q$—(CH$_2$)$_r$G, $R^6$ represents $C_1$–$C_{12}$-alkyl, $C_1$–$C_{12}$-alkoxy, $C_2$–$C_{12}$-alkenyl, $C_2$–$C_{12}$-alkenyloxy, represents in each case unsubstituted or halogen-, $C_1$–$C_4$-alkyl-, $C_2$–$C_4$-alkenyl-, $C_1$–$C_4$-halogenoalkyl- or $C_2$–$C_4$-halogenoalkenyl-substituted $C_3$–$C_8$-cycloalkyl, $C_3$–$C_8$-cycloalkyloxy or $C_3$–$C_8$-cycloalkyl-$C_1$–$C_6$-alkyloxy; or represents phenyl or naphthyl which is in each case unsubstituted or mono- to tetrasubstituted by nitro, halogen, $C_1$–$C_{12}$-alkyl, $C_1$–$C_{12}$-alkoxy, $C_1$–$C_{12}$-halogenoalkyl or $C_1$–$C_{12}$-halogenoalkoxy, $R^7$ represents hydrogen or $C_1$–$C_{12}$-alkyl, $R^8$ represents $C_1$–$C_{12}$-alkyl, $C_1$–$C_{12}$-halogenoalkyl, represents in each case unsubstituted or halogen-, $C_1$–$C_4$-alkyl-, $C_2$–$C_4$-alkenyl-, $C_1$–$C_4$-halogeno-alkyl- or $C_2$–$C_4$-halogenoalkenyl-substituted $C_3$–$C_8$-cycloalkyl or $C_3$–$C_8$-cycloalkyl-$C_1$–$C_6$-alkyl; or represents phenyl or phenyl-$C_1$–$C_6$-alkyl, each of which is unsubstituted or mono- to tetrasubstituted by halogen, $C_1$–$C_{12}$-alkyl, $C_1$–$C_{12}$-alkoxy, $C_1$–$C_{12}$-halogenoalkyl or $C_1$–$C_{12}$-halogenoalkoxy, p, q and r independently of one another each represent 0, 1, 2 or 3, their sum being smaller than 6 and greater than 1, $R^9$ and $R^{10}$ independently of one another each represent hydrogen or $C_1$–$C_4$-alkyl, G represents cyano, represents a 5- or 6-membered heterocycle having 1 to 3 identical or different heteroatoms from the group consisting of nitrogen, oxygen and sulphur and being unsubstituted or mono- to trisubstituted by halogen, $C_1$–$C_4$-alkyl or $C_1$–$C_4$-halogenoalkyl and optionally, at the point of linkage, by the radical $R^{11}$, or represents one of the following groupings:

(a) —CO—R$^{11}$ (b) —CO—OR$^{12}$ (c) —CO—NR$^{13}$R$^{14}$ (d) —CS—NR$^{13}$R$^{14}$ (e) 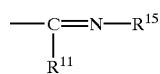

(f) 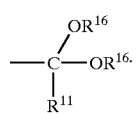

-continued (g) 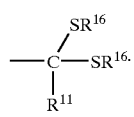

(h) 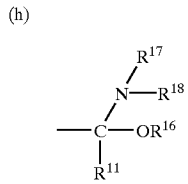

(i) 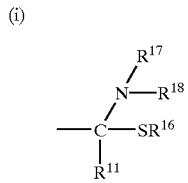

(j) 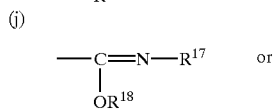

(k) 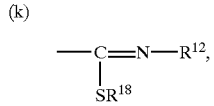

$R^{11}$ represents hydrogen, $C_1$–$C_6$-alkyl, $C_2$–$C_6$-alkenyl, $C_1$–$C_4$-halogenoalkyl, $C_2$–$C_6$-halogenoalkenyl, represents unsubstituted or halogen-, $C_1$–$C_4$-alkyl- or $C_1$–$C_4$-halogenoalkyl-substituted $C_3$–$C_6$-cycloalkyl or represents phenyl which is unsubstituted or mono- to pentasubstituted by $C_1$–$C_4$-alkylcarbonylamino, $C_1$–$C_4$-alkylcarbonyl-$C_1$–$C_4$-alkylamino and/or radicals from the list $W^3$, $R^{12}$ represents hydrogen, $C_1$–$C_4$-alkyl, $C_2$–$C_6$-alkenyl, $C_1$–$C_4$-halogenoalkyl, $C_2$–$C_6$-halogenoalkenyl, represents in each case unsubstituted or halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl; or represents $C_6$–$C_{10}$-aryl-$C_1$–$C_4$-alkyl, which is unsubstituted or mono- to tetrasubstituted by radicals from the list $W^3$, $R^{13}$ and $R^{14}$ independently of one another each represent hydrogen, $C_1$–$C_4$-alkyl, $C_3$–$C_6$-alkenyl, $C_1$–$C_4$-halogenoalkyl, $C_3$–$C_6$-halogenoalkenyl, $C_1$–$C_4$-alkoxy, represent in each case unsubstituted or halogen-, $C_1$–$C_4$-alkyl-or $C_1$–$C_4$-halogenoalkyl-substituted $C_3$–$C_6$-cycloalkyl or $C_3$–$C_6$-cycloalkyl-$C_1$–$C_4$-alkyl; represent phenyl or phenyl-$C_1$–$C_4$-alkyl, each of which is unsubstituted or mono- to pentasubstituted by radicals from the list $W^3$, represent —$OR^{12}$ or —$NR^{11}R^{12}$ or together represent an alkylene chain having 4 to 6 members in which optionally one methylene group is replaced by oxygen, $R^{15}$ represents —$OR^{12}$, —$NR^{11}R^{12}$ or —$N(R^{11})$—$COOR^{12}$, $R^{16}$, $R^{17}$ and $R^{18}$ independently of one another each represent $C_1$–$C_6$-alkyl, $W^1$ represents hydrogen, halogen, cyano, formyl, nitro, $C_1$–$C_6$-alkyl, tri-$C_1$–$C_4$-alkylsilyl, $C_1$–$C_{16}$-alkoxy, $C_1$–$C_6$-halogenoalkyl, $C_1$–$C_6$-halo-genoalkoxy, $C_2$–$C_6$-halogenoalkenyloxy, $C_1$–$C_6$-alkylcarbonyl, $C_1$–$C_{16}$-alkoxycarbonyl, pentafluorothio or —$S(O)_OR^3$, $W^2$ represents halogen, cyano, formyl, nitro, $C_1$–$C_6$-alkyl, tri $C_1$–$C_4$-alkylsilyl, $C_1$–$C_{16}$-alkoxy, $C_1$–$C_6$-halogenoalkyl, $C_1$–$C_6$-halogenoalkoxy, $C_1$–$C_6$-alkylcarbonyl, $C_1$–$C_{16}$-alkoxycarbonyl, pentafluorothio, —$S(O)_OR^3$ or —$C(R^{11})$=N—$R^{15}$, $W^3$ represents halogen, cyano, nitro, $C_1$–$C_4$-alkyl, $C_1$–$C_4$-alkoxy, $C_1$–$C_4$-halogenoalkyl, $C_1$–$C_4$-halogenoalkoxy, di-$C_1$–$C_4$-alkylamino, —$S(O)_OR^3$, —$COOR^{19}$ or —$CONR^{20}R^{21}$, $R^{19}$ represents hydrogen, $C_1$–$C_4$-alkyl, $C_1$–$C_4$-halogenoalkyl, represents unsubstituted or halogen-, $C_1$–$C_4$-alkyl- or $C_1$–$C_4$-halogenoalkyl-substituted $C_3$–$C_7$-cycloalkyl or represents phenyl which is unsubstituted or mono- to pentasubstituted by radicals from the list $W^4$, $R^{20}$ and $R^{21}$ independently of one another each represent hydrogen, $C_1$–$C_4$-alkyl, $C_3$–$C_6$-alkenyl, $C_1$–$C_4$-halogenoalkyl, $C_3$–$C_6$-halogenoalkenyl, $C_1$–$C_4$-alkoxy, represent in each case unsubstituted or halogen-, $C_1$–$C_4$-alkyl or $C_1$–$C_4$-halogenoalkyl-substituted $C_3$–$C_6$-cycloalkyl or $C_3$–$C_6$-cycloalkyl-$C_1$–$C_4$-alkyl; or represent phenyl or phenyl-$C_1$–$C_4$-alkyl, each of which is unsubstituted or mono- to pentasubstituted by radicals from the list $W^4$; represent —$OR^{16}$ or —$NR^{17}R^{18}$ or together represent an alkylene chain having 4 to 6 members in which optionally one methylene group is replaced by oxygen, and $W^4$ represents halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, di-$C_1$–$C_4$-alkylamino, $C_1$–$C_6$-alkoxycarbonyl, di-$C_1$–$C_6$-alkylaminocarbonyl or —$S(O)_OR^3$.

3. Compounds of the formula (I) according to claim 1, in which

Ar represents the radical

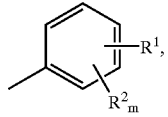

m represents 0, 1 or 2, $R^1$ represents a substituent in the meta or para position from the group consisting of hydrogen, fluorine, chlorine, bromine, cyano, tri-($C_1$–$C_4$-alkyl)-silyl, —CO—$NR^4R^5$, tetrahydropyranyl or one of the following groupings
(l) —X—A
(m) —B—Z—D or
(n) —Y—E, $R^2$ represents hydrogen, fluorine, chlorine, bromine, iodine, cyano, nitro, $C_1$–$C_{16}$-alkyl, $C_1$–$C_{16}$-alkoxy, represents in each case fluorine- or chlorine-substituted $C_1$–$C_6$-alkyl or $C_1$–$C_6$-alkoxy, represents $C_1$–$C_8$-alkoxy-$C_1$–$C_8$-alkoxy or —$S(O)_OR^3$, with the proviso that $R^1$ does not represent hydrogen if m=1 and $R^2$=iodine, o represents 0, 1 or 2, $R^3$ represents $C_1$–$C_4$-alkyl or in each case fluorine- or chlorine-substituted methyl or ethyl, $R^4$ and $R^5$ independently of one another each represent hydrogen, $C_1$–$C_6$-alkyl, fluorine- or chlorine-substituted $C_1$–$C_6$-alkyl or represent phenyl or benzyl, each of which is unsubstituted or mono- or disubstituted by radicals from the list $W^1$, X represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylene-dioxy or di-$C_1$–$C_4$-alkylsilylene, A represents phenyl, naphthyl or tetrahydronaphthyl, each of which is unsubstituted or mono- to tetrasubstituted by radicals from the list $W^1$, or represents 5- to 10-membered heterocyclyl containing one or two aromatic rings and having 1 to 4 heteroatoms, which contains 0 to 4 nitrogen atoms, 0 to 2 oxygen atoms and 0 to 2 sulphur atoms, and is in each case unsubstituted or mono- to trisubstituted by radicals from the list $W^2$, B represents p-phenylene which is unsubstituted or mono- or disubstituted by radicals from the list $W^1$, Z represents oxygen or sulphur, D represents hydrogen, $C_1$–$C_{16}$-alkyl, $C_2$–$C_{16}$-alkenyl, $C_2$–$C_6$-alkinyl, represents in each case fluorine- or chlorine-substituted $C_1$–$C_4$-alkyl or $C_2$–$C_4$-alkenyl, represents $C_3$–$C_6$-cycloalkyl or $C_3$–$C_6$-cycloalkyl-$C_1$–$C_4$-alkyl, each of which is unsubstituted or substituted by fluorine, chlorine, bromine, $C_1$–$C_4$-alkyl, $C_2$–$C_4$-alkenyl, by fluorine- or chlorine-substituted $C_2$–$C_4$-alkenyl, by phenyl, styryl, represents in each case fluorine-, chlorine- or bromine-substituted phenyl or styryl, represents in each case unsubstituted or fluorine-, chlorine-, bromine- or $C_1$–$C_4$-alkyl-substituted $C_5$–$C_6$-cycloalkenyl or $C_5$–$C_6$-cycloalkenyl-$C_1$–$C_4$-alkyl, represents phenyl-$C_1$–$C_4$-alkyl, naphthyl-$C_1$–$C_4$-alkyl, tetrahydronaphthyl-$C_1$–$C_6$-alkyl or hetaryl-$C_1$–$C_4$-alkyl having 5 or 6 ring members and one or two heteroatoms from the group consisting of nitrogen, oxygen and sulphur, each of which is unsubstituted or substituted by nitro, fluorine, chlorine, bromine, $C_1$–$C_6$-alkyl, $C_1$–$C_6$-alkoxy or by in each case fluorine- or chlorine-substituted $C_1$–$C_4$-alkyl- or $C_1$–$C_4$-alkoxy; represents —CO—$R^6$, —CO—$NR^7R^8$ or the grouping —$(CH_2)_p$—$(CR^9R^{10})_q$—$(CH_2)_r$G, Z and D together may also represent substituted phenoxy-$C_1$–$C_3$-alkyl which is unsubstituted or substituted by nitro, fluorine, chlorine, bromine, $C_1$–$C_4$-alkyl, $C_1$–$C_4$-alkoxy or by in each case fluorine- or chlorine-substituted $C_1$–$C_4$-alkyl or $C_1$–$C_4$-alkoxy, Y represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylene-dioxy or represents p-phenylene which is unsubstituted or mono- or disubstituted by radicals from the list $W^1$, E represents hydrogen, $C_1$–$C_{16}$-alkyl, $C_2$–$C_{16}$-alkenyl, $C_2$–$C_6$-alkinyl, represents in each case fluorine- or chlorine-substituted $C_1$–$C_4$-alkyl or $C_2$–$C_4$-alkenyl, represents $C_3$–$C_6$-cycloalkyl which is unsubstituted or substituted by fluorine, chlorine, bromine, $C_1$–$C_4$-alkyl, $C_2$–$C_4$-alkenyl, by fluorine- or chlorine-substituted $C_2$–$C_4$-alkenyl, by phenyl, styryl, or by in each case fluorine-, chlorine- or bromine substituted phenyl or styryl, represents unsubstituted or fluorine-, chlorine-, bromine- or $C_1$–$C_4$-alkyl-substituted $C_1$–$C_6$-cycloalkenyl, represents phenyl which is unsubstituted or mono- to tri-substituted by radicals from the list $W^1$ or represents 5- or 6-membered hetaryl having 1 or 2 heteroatoms from the group consisting of nitrogen, oxygen and sulphur, each of which is unsubstituted or mono- or disubstituted by radicals from the list $W^2$, or represents the grouping —$(CH_2)_p$—$(CR^9R^{10})_q$—$(CH_2)_r$—G, $R^6$ represents $C_1$–$C_6$-alkyl, $C_1$–$C_6$-alkoxy, $C_2$–$C_6$-alkenyl, $C_2$–$C_6$-alkenyloxy, represents $C_3$–$C_6$-cycloalkyl, $C_3$–$C_6$-cycloalkyloxy or $C_3$–$C_6$-cycloalkyl-$C_1$–$C_2$-alkyloxy, each of which is unsubstituted or substituted by fluorine, chlorine, $C_1$–$C_3$-alkyl-, or by in each case fluorine- or chlorine-substituted $C_1$–$C_2$-alkyl- or $C_2$–$C_3$-alkenyl, or represents phenyl which is unsubstituted or mono- or disubstituted by fluorine, chlorine, bromine, iodine, $C_1$–$C_4$-alkyl, $C_1$–$C_4$-alkoxy or by in each case fluorine- or chlorine-substituted $C_1$–$C_3$-alkyl or $C_1$–$C_4$-alkoxy, $R^7$ represents hydrogen or $C_1$–$C_4$-alkyl, $R^8$ represents $C_1$–$C_4$-alkyl or represents phenyl or benzyl, each of which is unsubstituted or mono- or disubstituted by fluorine, chlorine, bromine, $C_1$–$C_4$-alkyl or by in each case fluorine-, or chlorine-substituted $C_1$–$C_4$-alkyl or $C_1$–$C_4$-alkoxy, p, q and r independently of one another each represent 0, 1, 2 or 3, their sum being smaller than 6 and greater than 1, $R^9$ and $R^{10}$ independently of one another each represent hydrogen or $C_1$–$C_4$-alkyl, G represents cyano, represents a 5- or 6-membered heterocycle having 1 to 3 identical or different heteroatoms from the group consisting of nitrogen, oxygen and sulphur and being unsubstituted or mono- to trisubstituted by fluorine, chlorine, bromine, $C_1$–$C_4$-alkyl or by fluorine- or chlorine-substituted $C_1$–$C_4$-alkyl and optionally, at the point of linkage, by the radical $R^{11}$, or represents one of the following groupings:

(a) —CO—$R^{11}$ (b) —CO—$OR^{12}$ (c) —CO—$NR^{13}R^{14}$ (d) —CS—$NR^{13}R^{14}$ (e) 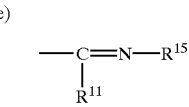

(f) 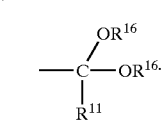

(g) 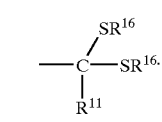

(h) 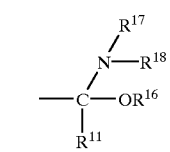

-continued (i) 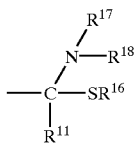

(j) 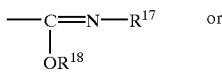 or (k) 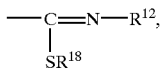

$R^{11}$ represents hydrogen, $C_1$–$C_6$-alkyl, $C_2$–$C_6$-alkenyl, represents in each case fluorine- or chlorine-substituted $C_1$–$C_4$-alkyl, $C_2$–$C_6$-alkenyl, represents $C_3$–$C_6$-cycloalkyl which is unsubstituted or substituted by fluorine, chlorine, $C_1$–$C_4$-alkyl or by fluorine- or chlorine-substituted $C_1$–$C_4$-alkyl, or represents phenyl which is unsubstituted or mono- to trisubstituted by $C_1$–$C_4$-alkylcarbonylamino, $C_1$–$C_4$-alkylcarbonyl-$C_1$–$C_4$-alkylamino and/or radicals from the list $W^3$, $R^{12}$ represents hydrogen, $C_1$–$C_4$-alkyl, $C_3$–$C_6$-alkenyl, represents in each case fluorine- or chlorine-substituted $C_1$–$C_4$-alkyl or $C_3$–$C_6$-alkenyl, represents $C_3$–$C_6$-cycloalkyl or $C_3$–$C_6$-cycloalkyl-$C_1$–$C_4$-alkyl, each of which is unsubstituted or substituted by fluorine, chlorine, $C_1$–$C_4$-alkyl or by fluorine- or chlorine-substituted $C_1$–$C_4$-alkyl, or represents phenyl-$C_1$–$C_4$-alkyl or naphthyl-$C_1$–$C_4$-alkyl, each of which is unsubstituted or mono- to trisubstituted by radicals from the list $W^3$, $R^{13}$ and $R^{14}$ independently of one another each represent hydrogen, $C_1$–$C_4$-alkyl, $C_3$–$C_6$-alkenyl, represent in each case fluorine- or chlorine substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is unsubstituted or substituted by fluorine, chlorine, $C_1$–$C_4$-alkyl or by fluorine- or chlorine-substituted $C_1$–$C_4$-alkyl, represent phenyl or phenyl-$C_1$–$C_4$-alkyl, each of which is unsubstituted or mono- to trisubstituted by radicals from the list $W^3$, represent —$OR^{12}$ or —$NR^{11}R^{12}$ or together represent —$(CH_2)_5$—, —$(CH_2)_6$— or —$(CH_2)_2$—O—$(CH_2)_2$—, $R^{15}$ represents —$OR^{12}$, —$NR^{11}R^{12}$ or —$N(R^{11})$—$COOR^{12}$, $R^{16}$, $R^{17}$ and $R^{18}$ independently of one another each represent $C_1$–$C_4$-alkyl, $W^1$ represents hydrogen, fluorine, chlorine, bromine, iodine, cyano, formyl, nitro, $C_1$–$C_4$-alkyl, $C_1$–$C_4$-alkoxy, represents in each case fluorine- or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl or —$S(O)_oR^3$, $W^2$ represents fluorine, chlorine, bromine, cyano, formyl, nitro, $C_1$–$C_4$-alkyl, $C_1$–$C_4$-alkoxy, represents in each case fluorine- or chlorine substituted $C_1$–$C_4$-alkyl or $C_1$–$C_4$-alkoxy, represents $C_1$–$C_4$-alkylcarbonyl, $C_1$–$C_4$-alkoxycarbonyl, —$S(O)_oR^3$ or -$C(R^{11})$=N—$R^{15}$, $W^3$ represents fluorine, chlorine, bromine, cyano, nitro, $C_1$–$C_4$-alkyl, $C_1$–$C_4$-alkoxy, represents in each case fluorine- or chlorine-substituted $C_1$–$C_4$-alkyl or $C_1$–$C_4$-alkoxy, represents di-$C_1$–$C_4$-alkylamino, —$S(O)_oR^3$, —$COOR^{19}$ or —$CONR^{20}R^{21}$, $R^{19}$ represents hydrogen, $C_1$–$C_4$-alkyl, fluorine- or chlorine-substituted $C_1$–$C_4$-alkyl, represents $C_3$–$C_6$-cycloalkyl which is unsubstituted or substituted by fluorine, chlorine, $C_1$–$C_4$-alkyl or by fluorine- or chlorine-substituted $C_1$–$C_4$-alkyl, or represents phenyl, which is unsubstituted or mono- to tri-substituted by radicals from the list $W^4$, $R^{20}$ and $R^{21}$ independently of one another each represent hydrogen, $C_1$–$C_4$-alkyl, $C_3$–$C_6$-alkenyl, represent in each case fluorine- or chlorine substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is unsubstituted or substituted by fluorine, chlorine, $C_1$–$C_4$-alkyl or by fluorine- or chlorine-substituted $C_1$–$C_4$-alkyl, or represent phenyl or phenyl-$C_1$–$C_4$-alkyl, each of which is unsubstituted or mono- to trisubstituted by radicals from the list $W^4$, represent —$OR^{16}$ or —$NR^{17}R^{18}$ or together represent —$(CH_2)_5$—, —$(CH_2)_6$— or —$(CH_2)_2$—O—$(CH_2)_2$—, and $W^4$ represents fluorine, chlorine, bromine, cyano, nitro, $C_1$–$C_4$-alkyl, $C_1$–$C_4$-alkoxy, represents in each case fluorine- or chlorine-substituted $C_1$–$C_4$-alkyl or $C_1$–$C_4$-alkoxy, di-$C_1$–$C_4$-alkylamino, $C_1$–$C_4$-alkoxycarbonyl, di-$C_1$–$C_6$-alkylaminocarbonyl or —$S(O)_oR^3$.

4. Compounds of the formula (I) according to claim 1, in which

Ar represents the radical

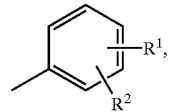

$R^1$ represents a substituent in the meta or para position from the group consisting of hydrogen, fluorine, chlorine, bromine, cyano, —CO—$NR^4R^5$, tetrahydropyranyl or one of the groupings below (l) —X—A (m-a) 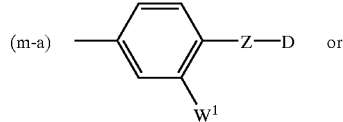 or (n) —Y—E, $R^2$ represents hydrogen, fluorine, chlorine, bromine, iodine, methyl, ethyl, methoxy, ethoxy, methylthio, ethylthio, trifluoromethyl, difluoromethoxy, trifluoromethoxy or trifluoromethylthio, o represents 0 or 2, with the proviso that $R^1$ does not represent hydrogen if m=1 and $R^2$=iodine, $R^3$ represents methyl, ethyl, n-propyl, isopropyl, difluoromethyl or tri-fluoromethyl, $R^4$ and $R^5$ independently of one another each represent hydrogen, methyl, ethyl, n-propyl, isopropyl, n-butyl, isobutyl, sec-butyl, tert-butyl or represent phenyl or benzyl, each of which is unsubstituted or monosubstituted by a radical from the list $W^1$, X represents a direct bond, oxygen, sulphur, carbonyl, —$CH_2$—, —$(CH_2)_2$—, —CH=CH— (E or Z), —C≡C—, —CH₂O—, —(CH₂)₂O—, —CH(CH₃)O—, —OCH₂—, —O(CH₂)₂—, —SCH₂—, —S(CH₂)₂—, —SCH(CH₃)—, $C_1$-$C_4$-alkylenedioxy, A represents phenyl which is unsubstituted or mono- or disubstituted by radicals from the list $W^1$ or represents furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl, each of which is unsubstituted or mono- or disubstituted by radicals from the list $W^2$, Z represents oxygen or sulphur, D represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, ₂-propenyl, butenyl, pentenyl, hexenyl, propargyl, butinyl, pentinyl, —CF₃, —CHF₂, —CClF₂, —CF₂CHFCl, —CF₂CH₂F, —CF₂CHF₂, —CF₂CCl₃, —CH₂CF₃, —CF₂CHFCF₃, —CH₂CF₂CHF₂, —CH₂CF₂CF₃, represents cyclopropyl, cyclobutyl, cyclopentyl, cyclohexyl, cyclopropylmethyl, cyclobutylmethyl, cyclopentylmethyl or cyclohexylmethyl, each of which is unsubstituted or mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH═CCl₂, phenyl, styryl or by in each case fluorine-, chlorine- or bromine-substituted phenyl or 4-chlorostyryl, represents cyclopentenyl, cyclohexenyl, cyclohexenylmethyl or cyclopentenylmethyl, each of which is unsubstituted or substituted by fluorine, chlorine, methyl, ethyl, n-propyl, isopropyl, n-butyl, isobutyl, sec-butyl or tert-butyl, represents benzyl, phenethyl, naphthylmethyl, tetrahydronaphthylmethyl, furylmethyl, thienylmethyl, pyrrolylmethyl, oxazolylmethyl, isoxazolylmethyl, thiazolylmethyl or pyridylmethyl, each of which is unsubstituted or mono- or disubstituted by nitro, fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, trifluoromethyl, trifluoromethoxy, difluoromethoxy or chlorodifluoromethoxy, represents —CO—$R^6$, —CO—$NR^7R^8$ or the grouping
—(CH₂)$_p$—($CR^9R^{10}$)$_q$—(CH₂)$_r$—G, Z and D together may also represent phenoxymethyl which is unsubstituted or mono- or disubstituted by nitro, fluorine, chlorine, bromine, methyl, ethyl, n-propyl, i-propyl, methoxy, ethoxy, n-propoxy, i-propoxy, trifluoromethyl, trifluoromethoxy, difluoromethoxy or chlorodifluoromethoxy, Y represents a direct bond, oxygen, sulphur, carbonyl, —CH₂—, —(CH₂)₂—, —CH═CH— (E or Z), —C≡C—, —CH₂O—, —(CH₂)₂O—, —CH(CH₃)O—, —OCH₂—, —O(CH₂)₂—, —SCH₂—, —S(CH₂)₂—, —SCH(CH₃)—, $C_1$-$C_4$-alkylenedioxy, or represents p-phenylene which is unsubstituted or monosubstituted by a radical from the list $W^1$, E represents hydrogen, methyl, ethyl, npropyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butinyl, pentinyl, —CF₃, —CHF₂, —CClF₂, —CF₂CHFCl, —CF₂CH₂F, —CF₂CHF₂, —CF₂CCl₃, —CH₂CF₃, —CF₂CHFCF₃, —CH₂CF₂CHF₂, —CH₂CF₂CF₃, represents cyclopropyl, cyclobutyl, cyclopentyl or cyclohexyl, each of which is unsubstituted or mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH═CCl₂, phenyl, styryl, or by in each case fluorine-, chlorine- or bromine-substituted phenyl or by 4-chlorostyryl, represents cyclopentenyl or cyclohexenyl, each of which is optionally substituted by fluorine, chlorine, methyl, ethyl, n-propyl, isopropyl, n-butyl, isobutyl, sec-butyl or tert-butyl, represents phenyl which is optionally mono- or disubstituted by radicals from the list $W^1$, represents furyl, thienyl, pyrrolyl, oxazolyl, isoxazolyl, thiazolyl or pyridyl, each of which is unsubstituted or mono- or disubstituted by radicals from the list $W^2$, or represents the grouping
—(CH₂)$_p$—($CR^9R^{10}$)$_q$—(CH₂)$_r$—G, $R^6$ represents methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, cyclopropyl, cyclohexyl, cyclohexyloxy, cyclohexylmethyloxy, phenyl, 2-chlorophenyl, 3-chlorophenyl, 2,6-difluorophenyl, 2,4-dichlorophenyl, 3,4-dichlorophenyl, 2-trifluoromethoxyphenyl or 4-trifluoromethoxyphenyl, $R^7$ represents hydrogen, $R^8$ represents methyl, ethyl or phenyl which is unsubstituted or monosubstituted by chlorine, p, q and r independently of one another each represent 0, 1, 2 or 3, their sum being smaller than 4 and greater than 1, $R^9$ and $R^{10}$ independently of one another each represent hydrogen, methyl, ethyl, n-propyl, isopropyl, n-butyl, isobutyl, sec-butyl, tert-butyl, G represents cyano, represents 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl, each of which is unsubstituted or mono- to trisubstituted by fluorine, chlorine, bromine, methyl, ethyl, n-propyl, isopropyl or trifluoromethyl and optionally, at the point of linkage, by the radical $R^{11}$, or represents one of the groupings below:

(a) —CO—$R^{11}$ (b) —CO—$OR^{12}$ (c) —CO—$NR^{13}R^{14}$ (d) —CS—$NR^{13}R^{14}$ (e) 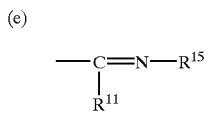

(f) 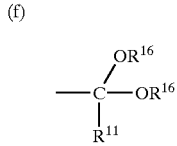

(g) 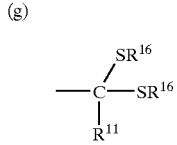

(h) 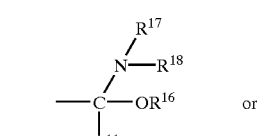 or (i) 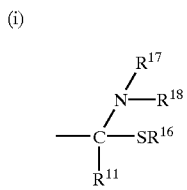

$R^{11}$ represents hydrogen, methyl, ethyl, n-propyl, isopropyl, n-butyl, isobutyl, sec-butyl, tert-butyl, the isomeric pentyls, the isomeric hexyls, —$CF_3$, —$CHF_2$, —$CClF_2$, —$CF_2CHFCl$, —$CF_2CH_2F$, —$CF_2CHF_2$, —$CF_2CCl_3$, —$CH_2CF_3$, $C_3$–$C_6$-alkenyl, $C_3$–$C_6$-alkenyl which is mono- to trisubstituted by fluorine or chlorine, represents cyclopropyl, cyclopentyl or cyclohexyl, each of which is unsubstituted or mono- or disubstituted by fluorine, chlorine, methyl, ethyl, n-propyl, isopropyl, —$CF_3$, —$CHF_2$, —$CClF_2$, —$CF_2CHFCl$, —$CF_2CH_2F$, —$CF_2CHF_2$, —$CF_2CCl_3$ or —$CH_2CF_3$, or represents phenyl which is unsubstituted or mono- or disubstituted by methylcarbonylamino, ethylcarbonylamino, methylcarbonyl-methylamino and/or radicals from the list $W^3$, $R^{12}$ represents hydrogen, methyl, ethyl, n-propyl, isopropyl, n-butyl, isobutyl, sec-butyl, tert-butyl, —$CH_2CF_3$, allyl, represents cyclopropyl, cyclopentyl, cyclohexyl, cyclopropylmethyl, cyclopentylmethyl, cyclohexylmethyl, cyclopropylethyl, cyclopentylethyl or cyclohexylethyl, each of which is optionally mono- or disubstituted by fluorine, chlorine, methyl, ethyl, n-propyl, isopropyl, —$CF_3$, —$CHF_2$, —$CClF_2$, —$CF_2CHFCl$, —$CF_2CH_2F$, —$CF_2CHF_2$, —$CF_2CCl_3$ or —$CH_2CF_3$, or represents benzyl or phenethyl, each of which is unsubstituted or mono- or disubstituted by radicals from the list $W^3$, $R^{13}$ and $R^{14}$ independently of one another each represent hydrogen, methyl, ethyl, n-propyl, isopropyl, n-butyl, isobutyl, sec-butyl, tert-butyl, —$CH_2CF_3$, methoxy, ethoxy, allyl, represent cyclopropyl, cyclopentyl, cyclohexyl, cyclopropylmethyl, cyclopentylmethyl or cyclohexylmethyl, each of which is unsubstituted or mono- or disubstituted by fluorine, chlorine, methyl, ethyl, n-propyl, isopropyl or trifluoromethyl, represent phenyl, benzyl or phenethyl, each of which is unsubstituted or mono- or disubstituted by radicals from the list $W^3$, represent —$OR^{12}$ or —$NR^{11}R^{12}$, $R^{15}$ represents —$OR^{12}$, —$NR^{11}R^{12}$ or —$N(R^{11})$—$COOR^{12}$, $R^{16}$, $R^{17}$ and $R^{18}$ independently of one another each represent methyl, ethyl, n-propyl or isopropyl, $W^1$ represents hydrogen, fluorine, chlorine, bromine, cyano, formyl, nitro, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, —$CF_3$, —$CHF_2$, —$CClF_2$, —$CF_2CHFCl$, —$CF_2CH_2F$, —$CF_2CHF_2$, —$CF_2CCl_3$, —$CH_2CF_3$, —$CF_2CHFCF_3$, —$CH_2CF_2CHF_2$, —$CH_2CF_2CF_3$, trifluoromethoxy, difluoromethoxy, chlorodifluoromethoxy, acetyl, propionyl, butyryl, isobutyryl, methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl or —$S(O)_OR^3$, $W^2$ represents fluorine, chlorine, bromine, cyano, methyl, ethyl, n-propyl, isopropyl, trifluoromethyl, trifluoromethoxy, difluoromethoxy, chlorodifluoromethoxy, acetyl, trifluoromethylthio, —$CH=N$—$OCH_3$, —$CH=N$—$OC_2H_5$, —$CH=N$—$OC_3H_7$, —$C(CH_3)=N$—$OCH_3$, —$C(CH_3)=N$—$OC_2H_5$, —$C(CH_3)=N$—$OC_3H_7$, —$C(C_2H_5)=N$—$OCH_3$, —$C(C_2H_5)=N$—$OC_2H_5$ or —$C(C_2H_5)=N$—$OC_3H_7$, $W^3$ represents fluorine, chlorine, cyano, nitro, methyl, ethyl, methoxy, ethoxy, methylthio, trifluoromethyl, trifluoromethoxy, trifluoromethylthio, dimethylamino, diethylamino, —$COOR^{19}$ or —$CONR^{20}R^{21}$, $R^{19}$ represents hydrogen, methyl, ethyl, n-propyl, isopropyl, tert-butyl, —$CH_2CF_3$, represents cyclopropyl, cyclopentyl or cyclohexyl, each of which is unsubstituted or mono- or disubstituted by fluorine, chlorine, methyl, ethyl, n-propyl, isopropyl or —$CF_3$, or represents phenyl which is unsubstituted or mono- or disubstituted by radicals from the list $W^4$, $R^{20}$ and $R^{21}$ independently of one another each represent hydrogen, methyl, ethyl, n-propyl, isopropyl, n-butyl, isobutyl, sec-butyl, tert-butyl, —$CH_2CF_3$, methoxy, ethoxy, allyl, represent cyclopropyl, cyclopentyl, cyclohexyl, cyclopropylmethyl, cyclopentylmethyl or cyclohexyl methyl, each of which is unsubstituted or mono- or disubstituted by fluorine or chlorine, represent phenyl, benzyl or phenethyl, each of which is unsubstituted or mono- or disubstituted by the radicals from the list $W^4$, represent —$OR^{16}$ or —$NR^{17}R^{18}$, and $W^4$ represents fluorine, chlorine, bromine, cyano, nitro, methyl, ethyl, tert-butyl, methoxy, ethoxy, methylthio, trifluoromethyl, trifluoromethoxy or trifluoromethylthio.

5. A process for preparing a compound of the formula (I) according to claim 1, wherein A) cyclic imines of the formula (I)

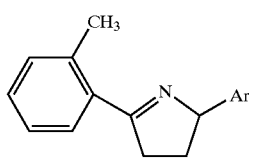
(I)

in which

Ar is as defined in claim 1 are obtained by
  a) reacting aminoketone derivatives of the formula (VIII)

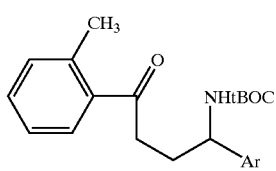
(VIII)

in which

Ar is as defined in claim 1 with an acid, followed by cyclocondensation, optionally in the presence of an acid binder, or
  b) reducing the nitro group of nitroketones of the formula (XVIII)

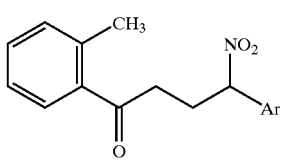
(XVIII)

in which

Ar is as defined in claim 1, where

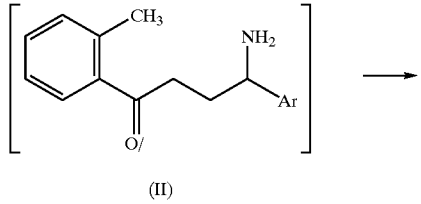
(II)

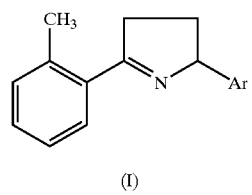
(I)

an aminoketone intermediate of the formula (II) is formed which, however, is cyclocondensed in situ to (I), optionally in an acidic medium, or c) hydrolyzing imines of the formula (XXVII)

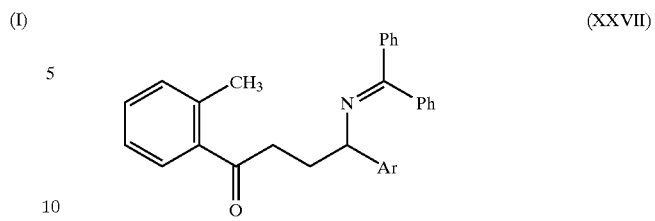
(XXVII)

in which

Ar is as defined in claim 1 with aqueous acids

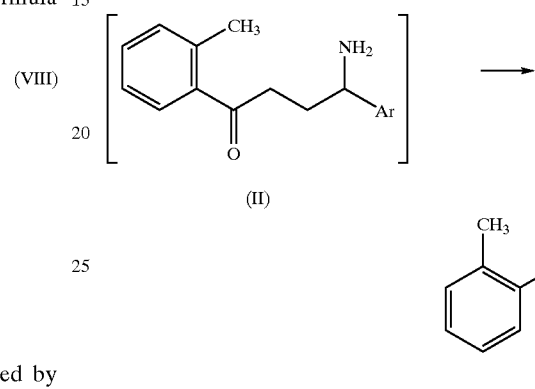

where an aminoketone intermediate of the formula (II) is formed which, however, is cyclocondensed in situ to (I), or
B) reacting compounds of the formula (III)

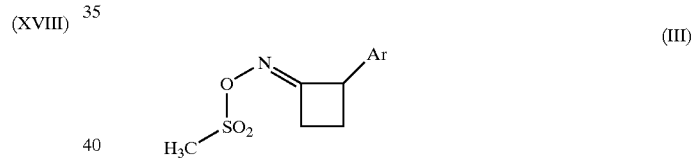
(III)

in which

Ar is as defined in claim 1 with aryl Grignard compounds of the formula (IV)

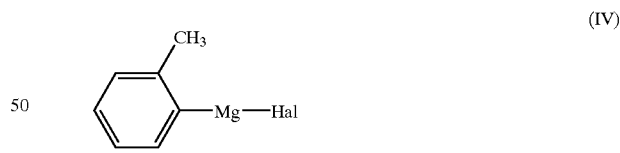
(IV)

in which

Hal represents chlorine, bromine or iodine in the presence of a diluent, or
C) compounds of the formula (I-b)

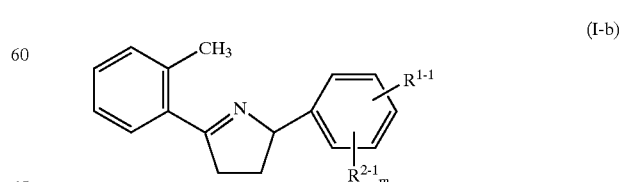
(I-b)

in which m is as defined in claim 1 $R^{1-1}$ represents A or one of the groupings below
(m) —B—Z—D

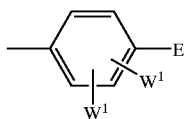
(n-a)

where A, B, D, E, W 1 and Z are each as defined in claim 1 and $R^{2-1}$ represents hydrogen, fluorine, cyano, nitro, alkyl, alkoxy, halo-genoalkyl, halogenoalkoxy, alkoxyalkoxy or —$SR^3$ where $R^3$ is as defined in claim 1 are obtained by coupling compounds of the formula (V)

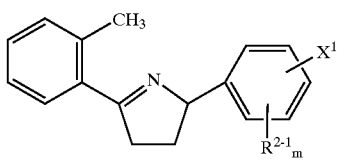
(V)

in which $R^{2-1}$ and m are each as defined above and $X^1$ represents bromine, iodine or —$OSO_2CF_3$ with boronic acids of the formula (VI)

$R^{1-1}$—$B(OH)_2$ (VI)

in which $R^{1-1}$ is as defined above in the presence of a catalyst and in the presence of an acid binder and in the presence of a solvent, or D) cyclic imines of the formula (!-c)

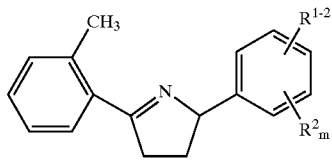
(I-c)

in which $R^2$ and m are each as defined in claim 1, $R^{l-2}$ represents one of the groupings below
(m-b) —B—Z—$D^1$
(n-b) —$Y^l$—$E^1$ in which B and Z are each as defined in claim 1, $Y^l$ represents oxygen or sulphur and $D_l$ and $E_l$ represent the grouping —$(CH_2)_p$—$(CR^9R^{10})_q$—$(CH_2)_r$G in which $R^9$, $R^{10}$, G, p, q and r are each as defined in claim 1 are obtained by condensing cyclic imines of the formula (I-d)

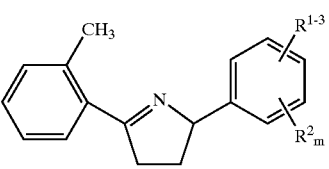
(I-d)

in which $R^2$ and m are each as defined in claim 1 and $R^{1-3}$ represents one of the groupings below
(m-c) —B—Z—H
(n-c) —$Y^1$—H in which B, $Y^1$ and Z are each as defined in claim 1 with compounds of the formula (VII)

Ab—$(CH_2)_p$—$(CR^9R^{10})_q$—$(CH_2)_r$G (VII)

in which $R^9$, $R^{10}$, G, p, q and r are each as defined in claim 1 and

Ab represents a leaving group, or

E) cyclic lines of the formula (I-e)

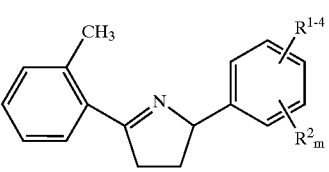
(I-e)

in which $R^2$ and m are each as defined in claim 1 and $R^{1-4}$ represents a grouping from the description of the compounds of the formula (I) according to the invention which contains the radical G, where G represents one of the groupings (e) to (k) mentioned in claim 1, are obtained by generally customary and known derivatizations of compounds of the formula (I) in which G represents cyano or one of the groupings (a) to (d).

6. Pesticides, characterized in that they contain at least one compound of the formula (I) according to claim 1 and extenders and/or surfactants.

7. Compounds of the formula (I) according to claim 1, in which

Ar represents the radical

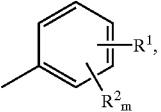

m represents 0, 1 or 2, $R^1$ represents a substituent in the meta or para position from the group consisting of hydrogen, fluorine, chlorine, bromine, cyano, tri-($C_1$–$C_4$-alkyl)-silyl, —CO—$NR^4R^5$, tetrahydropyranyl or one of the following groupings
(l) —X—A
(m) —B—Z—D or
(n) —Y—E, $R^2$ represents hydrogen, fluorine, chlorine, bromine, iodine, cyano, nitro, $C_1$–$C_{16}$-alkyl, $C_1$–$C_{16}$-alkoxy, represents in each case fluorine- or chlorine-substituted $C_1$–$C_6$-alkyl or $C_1$–$C_6$-alkoxy, represents $C_1$–$C_8$-alkoxy-$C_1$–$C_8$-alkoxy or —S(O)$_O$R$^3$, with the proviso that R$^1$ does not represent hydrogen if m=1 and R$^2$=iodine, o represents 0, 1 or 2, R$^3$ represents $C_1$–$C_4$-alkyl or in each case fluorine- or chlorine-substituted methyl or ethyl, R$^4$ and R$^5$ independently of one another each represent hydrogen, $C_1$–$C_6$-alkyl, fluorine- or chlorine-substituted $C_1$–$C_6$-alkyl or represent phenyl or benzyl, each of which is unsubstituted or mono- or disubstituted by radicals from the list W$^1$, X represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1C_4$-alkyleneoxy, $C_1$–$C_4$-oxyalkylene, $C_1$–$C_4$-thioalkylene, $C_1$–$C_4$-alkylene-dioxy or di-$C_1$–$C_4$-alkylsilylene, A represents phenyl, naphthyl or tetrahydronaphthyl, each of which is unsubstituted or mono- to tetrasubstituted by radicals from the list W$^1$, or represents furyl, benzofuryl, thienyl, benzothienyl, oxazolyl, benzoxazolyl, thiazolyl, benzothiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl, which is in each case unsubstituted or mono- to trisubstituted by radicals from the list W$^2$, B represents p-phenylene which is unsubstituted or mono- or disubstituted by radicals from the list W$^1$, Z represents oxygen or sulphur, D represents hydrogen, $C_1$–$C_{16}$-alkyl, $C_2$–$C_{16}$-alkenyl, $C_2$–$C_6$-alkinyl, represents in each case fluorine- or chlorine-substituted $C_1$–$C_4$-alkyl or $C_2$–$C_4$-alkenyl, represents $C_3$–$C_6$-cycloalkyl or $C_3$–$C_6$-cycloalkyl-$C_1$–$C_4$-alkyl, each of which is unsubstituted or substituted by fluorine, chlorine, bromine, $C_1$–$C_4$-alkyl, $C_2$–$C_4$-alkenyl, by fluorine- or chlorine-substituted $C_2$–$C_4$-alkenyl, by phenyl, styryl, represents in each case fluorine-, chlorine- or bromine-substituted phenyl or styryl, represents in each case unsubstituted or fluorine-, chlorine-, bromine- or $C_1$–$C_4$-alkyl-substituted $C_5$–$C_6$-cycloalkenyl or $C_5$–$C_6$-cycloalkenyl-$C_1$–$C_4$-alkyl, represents phenyl-$C_1$–$C_4$-alkyl, naphthyl-$C_1$–$C_4$-alkyl, tetrahydronaphthyl-$C_1$–$C_6$-alkyl or furylmethyl, thienylmethyl, pyrrolylmethyl, oxazolylmethyl, isoxazolylmethyl, thiazolylmethyl or pyridylmethyl, each of which is unsubstituted or substituted by nitro, fluorine, chlorine, bromine, $C_1$–$C_6$-alkyl, $C_1$–$C_6$-alkoxy or by in each case fluorine- or chlorine-substituted $C_1$–$C_4$-alkyl- or $C_1$–$C_4$-alkoxy; represents —CO—R$^6$, —CO—NR$^7$R$^8$ or the grouping —(CH$_2$)$_p$—(CR$^9$R$^{10}$)$_q$—(CH$_2$)$_r$G, Z and D together may also represent substituted phenoxy-$C_1$–$C_3$-alkyl which is unsubstituted or substituted by nitro, fluorine, chlorine, bromine, $C_1$–$C_4$-alkyl, $C_1$–$C_4$-alkoxy or by in each case fluorine- or chlorine-substituted $C_1$–$C_4$-alkyl or $C_1$–$C_4$-alkoxy, Y represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkinylene, $C_1$–$C_4$-alkyleneoxy, $C_1$–$C_4$-oxyalkylene, $C_1$–$C_4$-thioalkylene, $C_1$–$C_4$-alkylene-dioxy or represents p-phenylene which is unsubstituted or mono- or disubstituted by radicals from the list W$^1$, E represents hydrogen, $C_1$–$C_{16}$-alkyl, $C_2$–$C_{16}$-alkenyl, $C_2$–$C_6$-alkinyl, represents in each case fluorine- or chlorine-substituted $C_1$–$C_4$-alkyl or $C_2$–$C_4$-alkenyl, represents $C_3$–$C_6$-cycloalkyl which is unsubstituted or substituted by fluorine, chlorine, bromine, $C_1$–$C_4$-alkyl, $C_2$–$C_4$-alkenyl, by fluorine- or chlorine-substituted $C_2$–$C_4$-alkenyl, by phenyl, styryl, or by in each case fluorine-, chlorine- or bromine substituted phenyl or styryl, represents unsubstituted or fluorine-, chlorine-, bromine- or $C_1$–$C_4$-alkyl-substituted $C_5$–$C_6$-cycloalkenyl, represents phenyl which is unsubstituted or mono- to tri-substituted by radicals from the list W$^1$ or represents furyl, thienyl, pyrrolyl, oxazolyl, isoxazolyl, thiazolyl or pyridyl, each of which is unsubstituted or mono- or disubstituted by radicals from the list W$^2$, or represents the grouping —(CH$_2$)$_p$—(CR$^9$R$^{10}$)$_q$—(CH$_2$)$_r$G, R$^6$ represents $C_1$–$C_6$-alkyl, $C_1$–$C_6$-alkoxy, $C_2$–$C_6$-alkyl, $C_2$–$C_6$-alkenyloxy, represents $C_3$–$C_6$-cycloalkyl, $C_3$–$C_6$-cycloalkyloxy or $C_3$–$C_6$-cycloalkyl-$C_1$–$C_2$-alkyloxy, each of which is unsubstituted or substituted by fluorine, chlorine, $C_1$–$C_3$-alkyl-, or by in each case fluorine- or chlorine-substituted $C_1$–$C_2$-alkyl- or $C_2$–$C_3$-alkenyl, or represents phenyl which is unsubstituted or mono- or disubstituted by fluorine, chlorine, bromine, iodine, $C_1$–$C_4$-alkyl, $C_1$–$C_4$-alkoxy or by in each case fluorine- or chlorine-substituted $C_1$–$C_3$-alkyl or $C_1$–$C_4$-alkoxy, R$^7$ represents hydrogen or $C_1$–$C_4$-alkyl, R$^8$ represents $C_1$–$C_4$-alkyl or represents phenyl or benzyl, each of which is unsubstituted or mono- or disubstituted by fluorine, chlorine, bromine, $C_1$–$C_4$-alkyl or by in each case fluorine-, or chlorine-substituted $C_1$–$C_4$-alkyl or $C_1$–$C_4$-alkoxy, p, q and r independently of one another each represent 0, 1, 2 or 3, their sum being smaller than 6 and greater than 1, R$^9$ and R$^{10}$ independently of one another each represent hydrogen or $C_1$–$C_4$-alkyl, G represents cyano, represents 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl, each of which is unsubstituted or mono- to trisubstituted by fluorine, chlorine, bromine, $C_1$–$C_4$-alkyl or by fluorine- or chlorine-substituted $C_1$–$C_4$-alkyl and optionally, at the point of linkage, by the radical R$^{11}$, or represents one of the following groupings:

(a) —CO—R$^{11}$ (b) —CO—OR$^{12}$ (c) —CO—NR$^{13}$R$^{14}$ (d) —CS—NR$^{13}$R$^{14}$ (e)

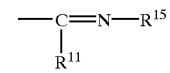

(f)
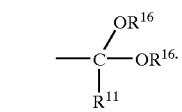

(g)
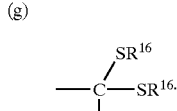

(h)
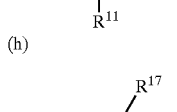

(i)
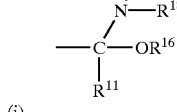

(j)
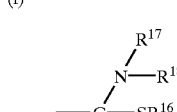

(k)
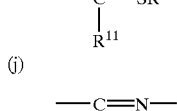

$R^{11}$ represents hydrogen, $C_1$–$C_6$-alkyl, $C_2$–$C_6$-alkenyl, represents in each case fluorine- or chlorine-substituted $C_1$–$C_4$-alkyl, $C_2$–$C_6$-alkenyl, represents $C_3$–$C_6$-cycloalkyl which is unsubstituted or substituted by fluorine, chlorine, $C_1$–$C_4$-alkyl or by fluorine- or chlorine-substituted $C_1$–$C_4$-alkyl, or represents phenyl which is unsubstituted or mono- to trisubstituted by $C_1$–$C_4$-alkylcarbonylamino, $C_1$–$C_4$-alkylcarbonyl-$C_1$–$C_4$-alkylamino and/or radicals from the list $W^3$, $R^{12}$ represents hydrogen, $C_1$–$C_4$-alkyl, $C_3$–$C_6$-alkenyl, represents in each case fluorine- or chlorine-substituted $C_1$–$C_4$-alkyl or $C_3$–$C_6$-alkenyl, represents $C_3$–$C_6$-cycloalkyl or $C_3$–$C_6$-cycloalkyl-$C_1$–$C_4$-alkyl, each of which is unsubstituted or substituted by fluorine, chlorine, $C_1$–$C_4$-alkyl or by fluorine- or chlorine-substituted $C_1$–$C_4$-alkyl, or represents phenyl-$C_1$–$C_4$-alkyl or naphthyl-$C_1$–$C_4$-alkyl, each of which is unsubstituted or mono- to trisubstituted by radicals from the list $W^3$, $R^{13}$ and $R^{14}$ independently of one another each represent hydrogen, $C_1$–$C_4$-alkyl, $C_3$–$C_6$-alkenyl, represent in each case fluorine- or chlorine substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is unsubstituted or substituted by fluorine, chlorine, $C_1$–$C_4$-alkyl or by fluorine- or chlorine-substituted $C_1$–$C_4$-alkyl, represent phenyl or phenyl-$C_1$–$C_4$-alkyl, each of which is unsubstituted or mono- to trisubstituted by radicals from the list $W^3$, represent —$OR^{12}$ or —$NR^{11}R^{12}$ or together represent —$(CH_2)_5$—, —$(CH_2)_6$— or —$(CH_2)_2$—O—$(CH_2)_2$—, $R^{15}$ represents —$OR^{12}$, —$NR^{11}R^{12}$ or —$N(R^{11})$—$COOR^{12}$, $R^{16}$, $R^{17}$ and $R^{18}$ independently of one another each represent $C_1$–$C_4$-alkyl, $W^1$ represents hydrogen, fluorine, chlorine, bromine, iodine, cyano, formyl, nitro, $C_1$–$C_4$-alkyl, $C_1$–$C_4$-alkoxy, represents in each case fluorine- or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl or —$S(O)_OR^3$, $W^2$ represents fluorine, chlorine, bromine, cyano, formyl, nitro, $C_1$–$C_4$-alkyl, $C_1$–$C_4$-alkoxy, represents in each case fluorine- or chlorine substituted $C_1$–$C_4$-alkyl or $C_1$–$C_4$-alkoxy, represents $C_1$–$C_4$-alkylcarbonyl, $C_1$–$C_4$-alkoxycarbonyl, —$S(O)_OR^3$ or —$C(R^{11})$=N—$R^{15}$, $W^3$ represents fluorine, chlorine, bromine, cyano, nitro, $C_1$–$C_4$-alkyl, $C_1$–$C_4$-alkoxy, represents in each case fluorine- or chlorine-substituted $C_1$–$C_4$-alkyl or $C_1$–$C_4$-alkoxy, represents di-$C_1$–$C_4$-alkylamino, —$S(O)_OR^3$, —$COOR^{19}$ or —$CONR^{20}R^{21}$, $R^{19}$ represents hydrogen, $C_1$–$C_4$-alkyl, fluorine- or chlorine-substituted $C_1$–$C_4$-alkyl, represents $C_3$–$C_6$-cycloalkyl which is unsubstituted or substituted by fluorine, chlorine, $C_1$–$C_4$-alkyl or by fluorine- or chlorine-substituted $C_1C_4$-alkyl, or represents phenyl, which is unsubstituted or mono- to tri-substituted by radicals from the list $W^4$, $R^{20}$ and $R^{21}$ independently of one another each represent hydrogen, $C_1$–$C_4$-alkyl, $C_3$–$C_6$-alkenyl, represent in each case fluorine- or chlorine substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is unsubstituted or substituted by fluorine, chlorine, $C_1$–$C_4$-alkyl or by fluorine- or chlorine-substituted $C_1$–$C_4$-alkyl, or represent phenyl or phenyl-$C_1$–$C_4$-alkyl, each of which is unsubstituted or mono- to trisubstituted by radicals from the list $W^4$, represent —$OR^{16}$ or —$NR^{17}R^{18}$ or together represent —$(CH_2)_5$—, —$(CH_2)_6$— or —$(CH_2)_2$—O—$(CH_2)_2$—, and $W^4$ represents fluorine, chlorine, bromine, cyano, nitro, $C_1$–$C_4$-alkyl, $C_1$–$C_4$-alkoxy, represents in each case fluorine- or chlorine-substituted $C_1$–$C_4$-alkyl or $C_1$–$C_4$-alkoxy, di-$C_1$–$C_4$-alkylamino, $C_1$–$C_4$-alkoxycarbonyl, di-$C_1$–$C_6$-alkylaminocarbonyl or —$S(O)_OR^3$.

8. Compounds of formula (I-a)

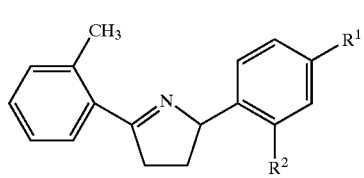

in which
$R^1$ represents hydrogen or phenyl which is mono- or disubstituted by radicals from the list $W^1$ or represents one of the groupings below
(m-b) —B—O—D or
(l) —Y—E,
B represents p-phenylene which is unsubstituted or monosubstituted by a radical from the list $W^1$,
Y represents a direct bond or represents p-phenylene which is unsubstituted or mono- or disubstituted by radicals from the list $W^1$ and D and E each have the meanings defined in claim 4 where G represents cyano or one of the groupings below (a) —CO—$R^{11}$ or (e)

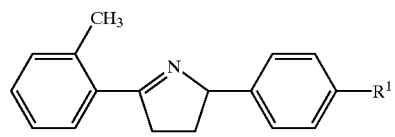

and $R^2$, $R^{11}$, $R^{15}$ and $W^1$ each have the meanings defined in any of claims 1 to 4.

9. Compounds of formula (I-f)

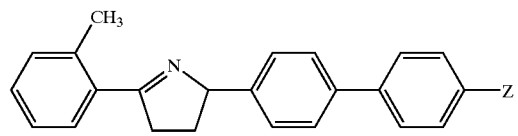

in which $R^1$ represents hydrogen or
- a) phenyl which is mono- or disubstituted by radicals from the list $W^2$ or
- b) furyl, thienyl, pyrrolyl, oxazolyl, isoxazolyl, thiazolyl or pyridyl, each of which is mono- or disubstituted by radicals from the list $W^2$, and $W^2$ has the meanings as defined in any of claims 1 to 4.

10. Compounds of formula (I-g)

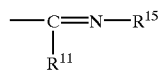

in which

Z represents hydrogen, fluorine, bromine, cyano, methyl, ethyl, n-propyl, isopropyl, trifluoromethyl, trifluoromethoxy, difluoromethoxy, chlorodifluoromethoxy, acetyl, trifluoromethylthio, —CH=N—OCH$_3$, —CH=N—OC$_2$H$_5$, —CH=N—OC$_3$H$_7$, —C(CH$_3$)=N—OCH$_3$, —C(CH$_3$)=N—OC$_2$H$_5$, —C(CH$_3$)=—OC$_3$H$_7$, —C(C$_2$H$_5$)=N—OC$_2$H$_5$ or —C(C$_2$H$_5$)=N—OC$_3$H$_7$.

11. Compounds of formula (V)

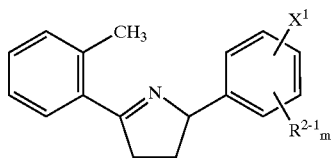

in which $R^{2-1}$ represents hydrogen, fluorine, cyano, nitro alkyl, alkoxy, halogenoalkyl, halogenoalkoxy, alkoxyalkoxy or —SR$^3$, $X^1$ represents bromine, iodine or —OSO$_2$ CF$_3$, m represents 0, 1, 2, 3 or 4, and $R^3$ represents alkyl or halogenalkyl.

12. Compounds of formula (V) according to claim 11, in which $R^{2-1}$ represents hydrogen, fluorine, cyano, nitro, $C_1$–$C_{16}$-alkyl, $C_1$–$C_{16}$-alkoxy, $C_1$–$C_6$-halogenoalkyl, $C_1$–$C_6$-halogenoalkoxy, $C_1$–$C_8$-alkoxy —$C_1$–$C_8$-alkoxy or —SR$_3$, $X^1$ represents bromine, iodine or —OSO$_2$ CF$_3$, m represents 0, 1, 2 or 3, and $R^3$ represents optionally fluorine- or chlorine-substituted $C_1$–$C_6$-alkyl.

13. Compounds of formula (V-a)

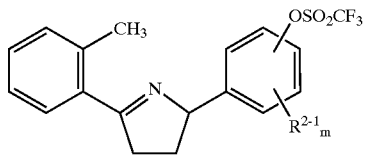

in which $R^{2-1}$ and m are each as defined in claim 11 or 12.

14. Method of controlling pests, characterized in that compounds of the formula (I) according to claim 1 are allowed to act on pests and/or their habitat.

15. Process for preparing pesticides, characterized in that compounds of the formula (I) according to claim 1 are mixed with extenders and/or surfactants.

* * * * *